United States Patent
Sui et al.

(10) Patent No.: US 6,818,646 B2
(45) Date of Patent: Nov. 16, 2004

(54) SUBSTITUTED PYRROLOPYRIDINONE DERIVATIVES USEFUL AS PHOSPHODIESTERASE INHIBITORS

(76) Inventors: Zhihua Sui, One Johnson & Johnson Plaza, New Brunswick, NJ (US) 08933; Mark J. Macielag, One Johnson & Johnson Plaza, New Brunswick, NJ (US) 08933; Jihua Guan, One Johnson & Johnson Plaza, New Brunswick, NJ (US) 08933; Weigin Jiang, One Johnson & Johnson Plaza, New Brunswick, NJ (US) 08933; James C. Lanter, One Johnson & Johnson Plaza, New Brunswick, NJ (US) 08933

( * ) Notice: Subject to any disclaimer, the term of this patent is extended or adjusted under 35 U.S.C. 154(b) by 0 days.

(21) Appl. No.: 10/638,901

(22) Filed: Aug. 11, 2003

(65) Prior Publication Data

US 2004/0044021 A1 Mar. 4, 2004

Related U.S. Application Data

(63) Continuation of application No. 09/847,749, filed on May 2, 2001, now Pat. No. 6,635,638.
(60) Provisional application No. 60/204,646, filed on May 17, 2000.

(51) Int. Cl.[7] .................. A61K 31/4965; C07D 239/02; C07D 515/00
(52) U.S. Cl. .................. 514/256; 514/292; 544/242; 546/81
(58) Field of Search ............................. 546/81; 514/292, 514/256; 544/242

(56) References Cited

U.S. PATENT DOCUMENTS

| | | | | |
|---|---|---|---|---|
| 4,235,907 A | * | 11/1980 | Pfenninger | 514/292 |
| 5,126,352 A | * | 6/1992 | Ganguly et al. | 514/293 |
| 6,043,252 A | * | 3/2000 | Bombrun | 514/292 |
| 6,335,346 B1 | * | 1/2002 | Fourtillan et al. | 514/285 |
| 6,635,638 B2 | * | 10/2003 | Sui et al. | 514/232.8 |

FOREIGN PATENT DOCUMENTS

| | | | |
|---|---|---|---|
| DE | 2035514 | * | 12/1971 |
| EP | 481429 | * | 1/2001 |
| WO | WO 95/29900 | * | 11/1995 |
| WO | WO 96/38438 | * | 12/1996 |
| WO | WO 00/40561 | * | 7/2000 |
| WO | WO 00/64897 | * | 11/2000 |
| WO | WO 01/87882 | * | 5/2001 |

OTHER PUBLICATIONS

Carniaux, J.F. et al, "Synthesis of a Novel Fused Tricyclic Quinolone system via Oxidation of 1,2,3, 4–Tetrahydro–β–Carbolines." Tetrahedron Letters (1997), 38(17) 2997–3000.

* cited by examiner

Primary Examiner—Rita Desai

(57) ABSTRACT

The invention relates to novel pyrrolopyridinone derivatives of the formula (I) or (II):

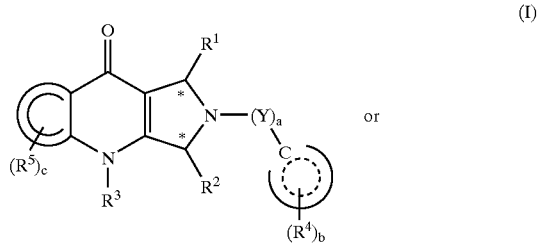

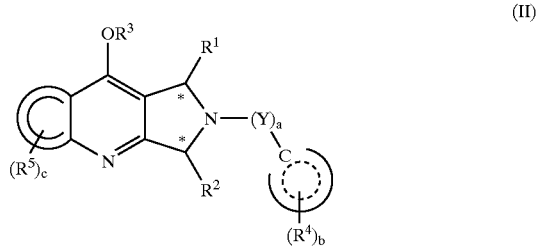

pharmaceutical compositions containing the compounds and their use for the treatment of sexual dysfunction.

2 Claims, No Drawings

SUBSTITUTED PYRROLOPYRIDINONE DERIVATIVES USEFUL AS PHOSPHODIESTERASE INHIBITORS

CROSS REFERENCE TO RELATED APPLICATION

This application is a continuation of parent application Ser. No. 09/847,749, filed May 2, 2001, now U.S. Pat. No. 6,635,638 which claims the benefit of U.S. provisional application Ser. No. 60/204,646 filed May 17, 2000, the contents of which are hereby incorporated by reference.

FIELD OF THE INVENTION

The invention relates to novel pyrrolopyridinone derivatives, intermediates used in, synthesis of and pharmaceutical compositions containing the compounds and their use for the treatment of sexual dysfunction. The compounds of the present invention are phosphodiesterase inhibitors useful for the treatment of sexual dysfunction, more particularly male erectile dysfunction.

BACKGROUND OF THE INVENTION

Erectile dysfunction (ED) is defined as the inability to achieve or maintain an erection sufficiently rigid for satisfactory sexual intercourse. Currently it is estimated that approximately 7–8% of the male population suffer from some degree of ED, the equivalent of at least 20 million men in the United States alone. Since the likelihood of ED increases with age, it is projected that the incidence of this condition will rise in the future as the average age of the population increases.

Male erectile dysfunction may be the consequence of psychogenic and/or organic factors. Although ED is multifactorial, certain sub-groups within the male population are more likely to present with the symptoms of the disorder. In particular, patients with diabetes, hypertension, heart disease, and multiple sclerosis have a particularly high prevalence of ED. In addition, patients who take certain classes of drugs such as antihypertensives, antidepressants, sedatives, and anxiolytics are more prone to suffer from ED.

Treatments for ED include a variety of pharmacologic agents, vacuum devices, and penile prostheses. Among the pharmacologic agents, papaverine, phentolamine, and alprostadil are currently used in practice. These agents are only effective after direct intracavernosal or intraurethral injection, and are associated with side effects such as priapism, fibrosis, penile pain and hematoma at the injection site. Vacuum devices are a noninasive alternative treatment for ED. These devices produce an erection by creating a negative pressure around the shaft of the penis resulting in an increased blood flow into the corpus cavernosum via passive arterial dilation. Although this form of therapy is frequently successful in ED of organic origin, complaints include the lack of spontaneity and the time involved in using a mechanical device, and difficulty and discomfort with ejaculation. A variety of semi-rigid or inflatable penile prostheses have been used with some success, particularly in diabetic men. These devices are generally considered when other treatment options have failed, and are associated with an increased risk of infection and ischemia.

Recently, the phosphodiesterase V (PDEV) inhibitor, sildenafil (Viagra®) was approved by the FDA as an orally effective medication for the treatment of ED. Sildenafil, 5-[2-ethoxy-5-(4-methylpiperazin-1-ylsulphonyl)phenyl]-1-methyl-3n-propyl-6,7-dihydro-1H-pyrazolo[4,3-d] pyrimidin-7-one and a number of related analogs and their use as antianginal agents are described in U.S. Pat. Nos. 5,250,534 and 5,346,901. The use of sildenafil and related analogs for treating male erectile dysfunction is described in PCT International Application Publication No. WO 94/28902, published Dec. 22, 1994. In clinical studies, the drug improved sexual function in about 70% of the men who suffer from ED of psychogenic or organic etiology. However, the drug showed less dramatic efficacy in patients who had undergone a radical prostatectomy, with improved erections in 43% of patients who took sildenafil versus 15% on placebo. In addition, the use of sildenafil is associated with several undesirable side effects including headache, flushing and disrupted color vision which result from non-selective effects on a variety of tissues. In spite of these shortcomings, the drug is viewed by patients as preferable to other treatments which involve the introduction of medication directly into the penis via injection, the use of an external device or a surgical procedure.

Daugan et. al, in U.S. Pat. No. 5,859,009 and EP 0740668 B1 describe the synthesis of a series of tetracyclic derivatives as inhibitors of cyclic guanosine 3',5' monophosphate specifically phosphodiesterase, and their use in treating cardiovascular disorders. Daugan et. al., in WO97/03675 teach the use of the tetracyclic derivatives for the treatment of impotence.

Garinaux, J.-F. et al., in *Tetrahedron Letters* 38(17), (1997), pp 2997–3000 disclose the synthesis of tricyclic quinolone derivatives via oxidation of 1,2,3,4-tetrahydro-β-carbolines.

Pfenninger, E. in DE 2803541 and U.S. Pat. No. 4,235,907 discloses substituted 9H-pyrrolo-[3,4-b]quinolin-9-ones and their use in the treatment of allergic asthma.

Sexually stimulated penile erection results from a complex interplay of physiological processes involving the central nervous system, the peripheral nervous system, and the smooth muscle. Specifically, release of nitric oxide from the non-adrenergic, non-cholinergic nerves and endothelium activates guanylyl cyclase and increases intracellular cGMP levels within the corpus cavernosum. The increase in intracellular cGMP reduces intracellular calcium levels, resulting in trabecular smooth muscle relaxation, which, in turn, results in corporal volume expansion and compression of the sub-tunical venules leading to penile erection.

PDEV has been found in human platelets and vascular smooth muscle, suggesting a role for this enzyme in the regulation of intracellular concentrations of cGMP in cardiovascular tissue. In fact, inhibitors of PDEV have been shown to produce endothelial-dependent vasorelaxation by potentiating the increases in intracellular cGMP induced by nitric oxide. Moreover, PDEV inhibitors selectively lower the pulmonary arterial pressure in animal models of congestive heart failure and pulmonary hypertension. Hence in addition to their utility in ED, PDEV inhibitors would likely be of therapeutic benefit in conditions like heart failure, pulmonary hypertension, and angina.

Agents that increase the concentration of cGMP in penile tissue, either through enhanced release or reduced breakdown of cGMP, are expected to be effective treatments for ED. The intracellular levels of cGMP are regulated by the enzymes involved in its formation and degradation, namely the guanylate cyclases and the cyclic nucleotide phosphodiesterases (PDEs). To date, at least nine families of mammalian PDEs have been described, five of which are capable of hydrolyzing the active, cGMP, to the inactive, GMP, under physiological conditions (PDEs I, II, V, VI, and IX). PDE V is the predominant isoform in human corpus cavernosum. Inhibitors of PDEV, therefore, would be expected to increase the concentration of cGMP in the corpus cavernosum and enhance the duration and frequency of penile erection.

Additionally, selective PDE inhibitors are known to be useful in the treatment of various disorders and conditions including male erectile dysfunction (ED), female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications.

Accordingly, it is an object of the invention to identify compounds which increase the concentration of cGMP in penile tissue through the inhibition of phosphodiesterases, specifically PDEV. It is another object of the invention to identify compounds which are useful for the treatment of sexual dysfunction, particularly erectile dysfunction and/or impotence in male animals and sexual dysfunction in female animals. Still another object of the invention is to identify methods for treating sexual dysfunction, especially erectile dysfunction, using the compounds of the present invention.

It is another object of the invention to identify compounds which are useful for the treatment of conditions of disorders mediated by PDEV, such as male erectile dysfunction, female sexual dysfunction, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication or diabetic complications.

We now describe a series of pyrrolopyridinone derivatives with the ability to inhibit phosphodiesterase type V in enzyme assays.

SUMMARY OF THE INVENTION

The present invention provides novel pyrrolopyridinone derivative compounds useful as phosphodiesterase inhibitors. More particularly, the present invention is directed to compounds of the general formula (I) or (II):

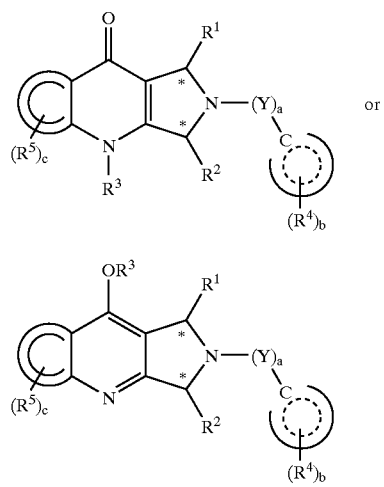

wherein
$R^1$ is selected from the group consisting of hydrogen, carboxy, —C(O)—$C_1$–$C_6$alkyl, —C(O)—$C_1$–$C_6$alkoxy, —C(O)—NH—$C_1$–$C_6$alkyl-$NH_2$, —C(O)—NH—$C_1$–$C_6$alkyl-$NHR^A$, —C(O)—NH—$C_1$–$C_6$alkyl-$N(R^A)_2$, —C(O)—$NH_2$, —C(O)—$NHR^A$, —C(O)—$N(R^A)_2$, —$C_1$–$C_6$alkyl-$NH_2$, —$C_1$–$C_6$alkyl-$NHR^A$, —$C_1$–$C_6$alkyl-$N(R^A)_2$, —NH—$C_1$–$C_6$alkyl-$N(R^A)_2$;

where each $R^A$ is independently selected from the group consisting of $C_1$–$C_6$alkyl, aryl, $C_1$–$C_6$aralkyl and heteroaryl, where the aryl, aralkyl or heteroaryl may be optionally substituted with one to three $R^B$;

where each $R^B$ is independently selected from the group consisting of halogen, nitro, cyano, $C_1$–$C_6$alkyl, $C_1$–$C_6$alkoxy, $C_1$–$C_6$alkylcarbonyl, carboxy$C_1$–$C_6$alkyl, $C_1$–$C_6$alkylsulfonyl, trifluoromethyl, amino, di($C_1$–$C_6$alkyl)amino, acetylamino, carboxy$C_1$–$C_6$alkylcarbonylamino, hydroxy$C_1$–$C_6$alkylamino, $NHR^A$ and $N(R^A)_2$;

$R^2$ is selected from the group consisting of $C_5$–$C_{10}$alkyl (optionally substituted with one to three substituents independently selected from halogen, hydroxy, nitro, amino, $NHR^A$ or $N(R^A)_2$), aryl (optionally substituted with one to three substituents independently selected from $R^C$), cycloalkyl (optionally substituted with one to three substituents independently selected from $R^A$), heteroaryl (optionally substituted with one to three substituents independently selected from $R^C$), and heterocycloalkyl (optionally substituted with one to three substituents independently selected from $R^C$);

where $R^C$ is selected from the group consisting of halogen, nitro, cyano, $C_1$–$C_6$alkyl, $C_1$–$C_6$alkoxy, trifluoromethyl, trifluoromethoxy, $NH_2$, $NH(C_1$–$C_6$alkyl) and $N(C_1$–$C_6$alkyl)$_2$;

$R^3$ is selected from the group consisting of hydrogen, $C_1$–$C_6$alkyl, $C_1$–$C_6$alkylcarbonyl, $C_2$–$C_6$alkenylcarbonyl and $C_2$–$C_6$alkynylcarbonyl;

b is an integer from 0 to 4;

$R^4$ is independently selected from the group consisting of halogen, hydroxy, carboxy, oxo, nitro, $C_1$–$C_6$alkyl, $C_1$–$C_6$alkoxy, $C_1$–$C_6$alkoxycarbonyl, trifluoromethyl, phenyl (wherein the phenyl group may be optionally substituted with one to three substituents independently selected from $R^D$), phenylsulfonyl, naphthyl, $C_1$–$C_6$aralkyl, —O-aralkyl, (wherein the aralkyl group may be optionally substituted with one to three substituents independently selected from $R^D$), heteroaryl (wherein the heteroaryl may be optionally substituted with one to three substituents independently selected from $R^D$), heterocycloalkyl, $NH_2$,

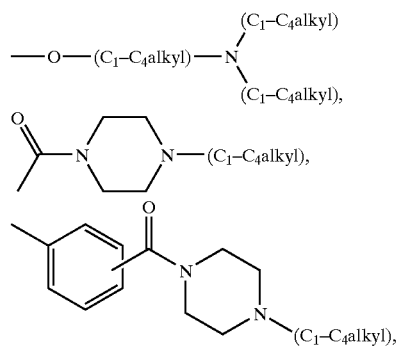

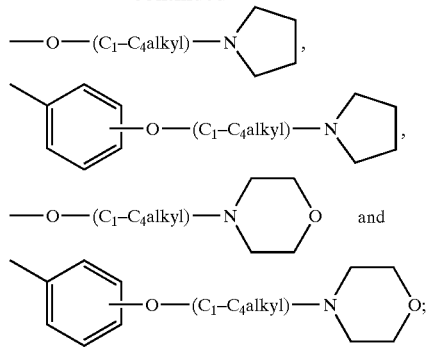

where each $R^D$ is independently selected from halogen, hydroxy, carboxy, oxo, $C_1$–$C_4$alkyl, $C_{1-4}$alkylthio, hydroxy$C_{1-4}$alkyl, $C_1$–$C_4$alkoxy, $C_1$–$C_4$alkyoxycarbonyl, $C_1$–$C_4$alkylcarbonyl, trifluoromethyl, trifluoromethoxy, $NH_2$, $NHR^A$, $N(R^A)_2$, $C(O)N(R^A)_2$, acetylamino, nitro, cyano, formyl, $C_1$–$C_6$alkylsulfonyl, carboxy$C_1$–$C_6$alkyl and aralkyl;

c is an integer from 0 to 4;

$R^5$ is independently selected from the group consisting of halogen, nitro, hydroxy, $C_1$–$C_6$alkyl, $C_1$–$C_6$alkoxy, —$NH_2$, —$NHR^A$, —$N(R^A)_2$, —$OR^A$, —$C(O)NH_2$, —$C(O)NHR^A$, —$C(O)N(R^A)_2$, —$NHC(O)R^A$, —$SO_2NHR^A$, —$SO_2N(R^A)_2$, where $R^A$ is as defined above, phenyl (optionally substituted with one to three substituents independently selected from $R^B$), heteroaryl (optionally substituted with one to three substituents independently selected from $R^B$) and heterocycloalkyl (optionally substituted with one to three substituents independently selected from $R^B$);

a is an integer from 0 to 1;

Y selected from the group consisting of —$C_1$–$C_6$alkyl-, —C(O)—, —($C_1$–$C_6$alkyl)carbonyl-, —($C_2$–$C_6$alkenyl)carbonyl-, —($C_2$–$C_6$alkynyl)carbonyl-, -carbonyl($C_1$–$C_6$alkyl)-, -carbonyl($C_2$–$C_6$alkenyl)-, —C(O)O—($C_1$–$C_6$alkyl)-, —C(S)—, —$SO_2$—, —($C_1$–$C_6$alkyl)sulfonyl-, -sulfonyl($C_1$–$C_6$alkyl)-, —C(O)NH—, —C(O)NH—($C_1$–$C_6$alkyl)-, —C(O)($C_3$–$C_7$cycloalkyl)- and —($C_3$–$C_7$cycloalkyl)-C(O)—;

is selected from the group consisting phenyl, furyl, thienyl and pyrrolyl;

is selected from the group consisting of aryl, heteroaryl, cycloalkyl and heterocycloalkyl;

provided that when $R^1$ is hydrogen, $R^3$ is hydrogen, b is 0, c is 0, a is 1, Y is —$CH_2$—,

is phenyl and is phenyl, then $R^2$ is not trimethoxyphenyl, (i.e. the compound is not 1,2,3,4-tetrahydro-2-(phenylmethyl)-3-(3,4,5-trimethoxyphenyl)-9H-pyrrolo[3,4-b]quinolin-9-one);

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating a condition selected from the group consisting of male erectile dysfunction (ED), impotence, female sexual dysfunction, female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of any of the compounds or pharmaceutical compositions described above.

An example of the invention is a method for increasing the concentration of cGMP in penile tissue through the inhibition of phosphodiesterases, specifically PDEV, in a male subject in need thereof comprising administering to the subject an effective amount of any of the compounds or pharmaceutical compositions described above.

Further exemplifying the invention is a method of producing endothelial-dependent vasorelaxation by potentiating the increases in intracellular cGMP induced by nitric oxide in a subject in need thereof comprising administering to the subject an effective amount of any of the compounds or pharmaceutical compositions described above.

An example of the invention is the use of any of the compounds described above in the preparation of a medicament for: (a) treating sexual dysfunction, especially male erectile dysfunction, (b) treating impotence, (c) increasing the concentration of cGMP in penile tissue through inhibition of phosphodiesterase, especially PDEV and/or (d) treating a condition selected from the group consisting of premature labor, dysmenorrhea, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication and diabetic complications in a subject in need thereof.

DETAILED DESCRIPTION OF THE INVENTION

The present invention provides novel pyrrolopyridinone derivatives useful for the treatment of sexual dysfunction, particularly male erectile dysfunction (ED). Although the compounds of the present invention are useful primarily for the treatment of male sexual dysfunction or erectile dysfunction, they may also be useful for the treatment of female sexual dysfunction, for example female sexual arousal dysfunction, female sexual dysfunction related to blood flow and nitric oxide production in the tissue of the vagina and clitoris, and of premature labor and dysmenorrhea.

More particularly, the compounds of the present invention are of the formula (I) or (II):

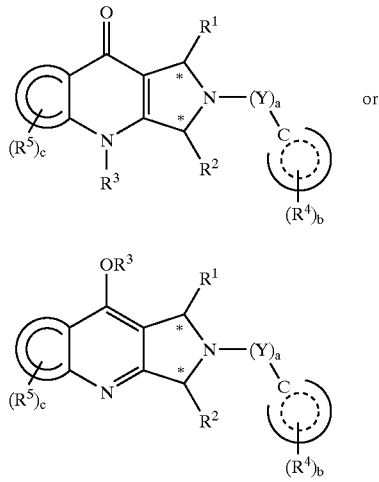

wherein all variables are as defined above, and pharmaceutically acceptable salts thereof.

Preferably, $R^1$ is hydrogen.

In an embodiment of the present invention $R^2$ is selected from the group consisting of phenyl (optionally substituted with one to two substituent selected from halogen, nitro, cyano, $C_1$–$C_3$alkyl, $C_1$–$C_3$alkoxy, trifluoromethyl, trifluoromethoxy, $NH_2$, $NH(C_1$–$C_3$alkyl) or $N(C_1$–$C_3$alkyl)$_2$), heteroaryl and heterocycloalkyl. Preferably, $R^2$ is selected from the group consisting of 3,4-methylenedioxyphenyl, 3,4-dimethoxyphenyl, 5-(2,3-dihydrobenzofuryl), 3,4-dihydrobenzo-[1,4]-dioxin-6-yl, 5-benxofuryl, 5-indanyl and 3-thienyl. More preferably, $R^2$ is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl. More preferably still, $R^2$ is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl. Most preferably, $R^2$ is selected from the group consisting of 3,4-methylenedioxyphenyl, and 5-(2,3-dihydrobenzofuryl).

Preferably, $R^3$ is selected from the group consisting of hydrogen and $C_1$–$C_4$alkyl. More preferably, $R^3$ is selected from the group consisting of hydrogen and methyl. Most preferably, $R^3$ is hydrogen.

Preferably, b is an integer from 0 to 4. More preferably b is in integer from 0 to 1.

In an embodiment of the present invention, $R^4$ is selected from the group consisting of halogen, hydroxy, carboxy, oxo, $C_1$–$C_3$alkyl, $C_1$–$C_3$alkoxy, $C_1$–$C_3$alkoxycarbonyl, phenyl (wherein the phenyl may be optionally substituted with one to two substituents selected from hydroxy, carboxy, $C_1$–$C_4$alkyl, $C_1$-$C_4$alkylthio, hydroxy$C_{1-4}$alkyl, $C_1$–$C_4$alkoxy, $C_1$–$C_4$alkyoxycarbonyl, $C(O)N(R^A)_2$, trifluoromethyl, trifluoromethoxy, amino, $(C_{1-4}$alkyl)amino, di$(C_{1-4}$alkyl)amino, nitro, cyano or formyl), O-aralkyl, heteroaryl (wherein the heteroaryl may be optionally substituted with one to two substituents selected from hydroxy, carboxy, oxo, $C_1$–$C_3$alkyl, $C_1$–$C_3$alkoxy, $C_1$–$C_3$alkyoxycarbonyl, $C(O)N(R^A)_2$, trifluoromethyl, trifluoromethoxy, amino, nitro, $C_1$–$C_3$alkylcarbonyl or $C_{1-4}$aralkyl), heterocycloalkyl,

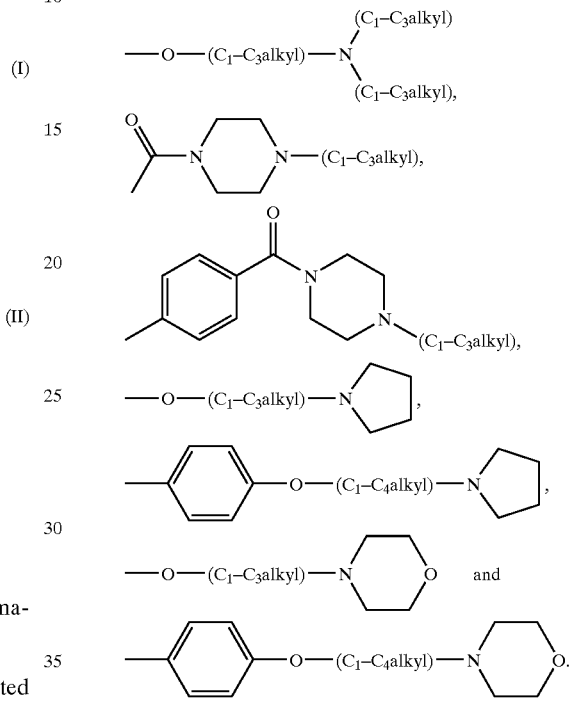

Preferably, $R^4$ is selected from the group consisting of bromo, hydroxy, carboxy, oxo, methyl, phenyl, 4-hydroxyphenyl, 3-hydroxymethylphenyl, 4-hydroxymethylphenyl, 4-carboxyphenyl, 4-methylphenyl, 4-methoxyphenyl, 3,4-dimethoxyphenyl, 4-methoxycarbonyl, 4-methoxycarbonylphenyl, 3-trifluoromethylphenyl, 4-cyanophenyl, 4-aminophenyl, 4-dimethylaminophenyl, 3-nitrophenyl, 4-nitrophenyl, 4-formylphenyl, 4-methylthiophenyl, benzyloxy, 2-pyridinyl, 3-pyridinyl, 4-pyridinyl, N-oxy-2-pyridinyl, 3-thienyl, 2-furyl, 1-imidazolyl, 5-(1-benzyl-2-methylimidazolyl), 5-(1,2-dimethylimidazolyl), 5-(1-methylimidazoly), 5-(1-benzylimidazolyl), 3,4-methylenedioxyphenyl,

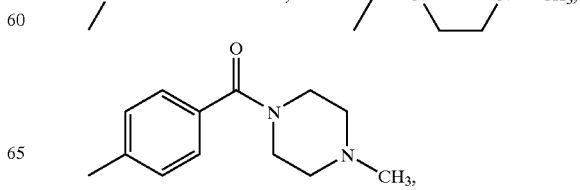

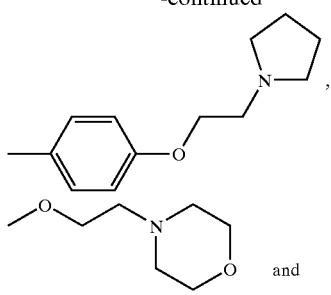

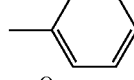

and

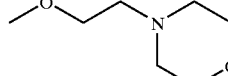

More preferably, $R^4$ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, 2-furyl, 3-thienyl, N-oxo-2-pyridinyl, 1-imidazolyl, 5-(1-benzyl-2-methylimidazolyl), 5-1,2-dimethylimidazolyl), 3,4-methylenedioxyphenyl,

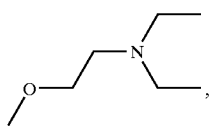

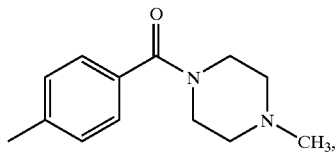

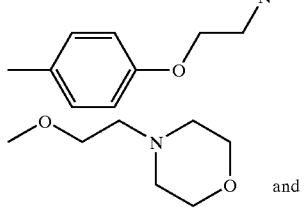

and

More preferably still, $R^4$ is selected from the group consisting of 5-bromo, 2-hydroxy, 6-hydroxy, 4-carboxy, phenyl, 4-hydroxyphenyl, 3-hydroxymethylphenyl, 4-hydroxymethyphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, N-oxo-2-pyridinyl, 3-thienyl, 2-furyl, 1-imidazolyl, 5-(1-benzyl-2-methylimidazolyl), 5-(1,2-dimethylimidazolyl), 3,4-methylenedioxyphenyl,

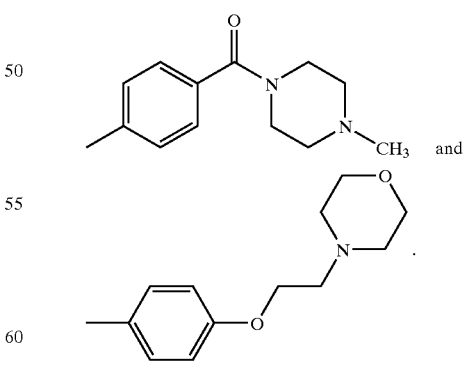

More preferably still, $R^4$ is selected from the group consisting of 6-hydroxy, 4-carboxy, phenyl, 4-hydroxyphenyl, 3-hydroxymethylphenyl, 4-methylphenyl, 4-methylthiophenyl, 4-methoxyphenyl, 3,4-dimethoxyphenyl, 4-methoxycarbonyl, 3-trifluoromethylphenyl, 3-nitrophenyl, 4-nitrophenyl, 2-pyridinyl, 3-pyridinyl, 4-pyridinyl, N-oxo-2-pyridinyl, 3-thienyl, 5-(1-benzyl-2-methylimidazolyl), 5-(1,2-dimethylimidazolyl),

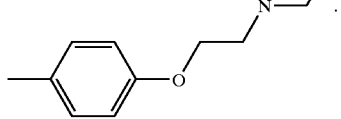

Most preferably, $R^4$ is selected from the group consisting of hydroxy, 4-methylphenyl, 4-methoxyphenyl, 3,4-dimethoxyphenyl, 4-methoxycarbonyl, 3-trifluoromethylphenyl, 4-nitrophenyl, 2-pyridinyl, 3-pyridinyl,

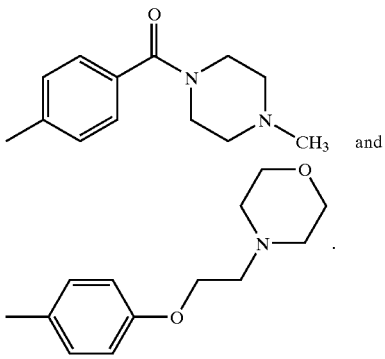

In a preferred embodiment c is 0. In another preferred embodiment a is an integer from 0 to 1.

In an embodiment of the present invention, Y is selected from the group consisting of —$C_1$-$C_4$alkyl-, —C(S)—, —C(O)—, —C(O)O—($C_1$-$C_4$alkyl)-, —C(O)—($C_1$-$C_4$alkyl)-, —C(O)—($C_2$-$C_4$alkenyl)-, C(O)—($C_3$-$C_7$cycloalkyl)- and —C(O)NH—($C_1$-$C_3$alkyl)-. Preferably, Y is selected from the group consisting of —$CH_2$—, —C(S)—, —C(O)—, —C(O)O—$CH_2$—, —C(O)—$CH_2CH_2$—, —C(O)—CH=CH—, —C(O)NH—$CH_2$—, —C(O)-cyclopropyl and —C(O)$CH_2$—. More preferably, Y is selected from the group consisting of —C(O)—, —C(O)O—$CH_2$—, —C(O)—$CH_2CH_2$—, —C(O)—CH=CH—, and —C(O)-cyclopropyl. More preferably still, Y is selected from the group consisting of —C(O)—, —C(O)O—$CH_2$— and —C(O)—CH=CH—. Most preferably, Y is selected from the group consisting of —C(O)— and —C(O)O—$CH_2$—;

Preferably,

is phenyl;

In an embodiment of the present invention,

is selected from the group consisting of phenyl, heteroaryl and heterocycloalkyl. Preferably,

is selected from the group consisting of phenyl, 2-furyl, 2-benzo(b)furyl, 2-pyrimidinyl, 2-pyridinyl, 3-pyridinyl, 4-pyridinyl, 1-imidazolyl, 2-imidazolyl, 2-thiazolyl, and 2-oxa-bicyclo[2,2,1]heptanyl. More preferably,

is selected from the group consisting of phenyl, 2-furyl, 2-benzo(b)furyl, 2-pyrimidinyl, 2-pyridinyl, 3-pyridinyl, 4-pyridinyl and 2-thiazolyl. Most preferably,

is selected from the group consisting of 2-furyl, 2-benzo(b)furyl, 4-pyridinyl, 2-pyrimidinyl and 2-thiazolyl.

The term "halogen" shall include iodine, bromine, chlorine and fluorine.

The term "alkyl", whether used alone or as part of a substituent group, shall mean straight or branched chain alkanes of one to ten carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl and 2-methylpentyl. Similarly, alkenyl and alkynyl groups include straight and branched chain alkenes and alkynes having two to ten carbon atoms, or any number within this range.

The term "alkoxy" shall denote an oxygen ether radical of the above described straight or branched chain alkyl group. For example, alkoxy radicals include methoxy, ethoxy, n-propoxy, n-butoxy, sec-butoxy, tert-butoxy, and the like.

The term "aryl" indicates an aromatic group such as phenyl, naphthyl, and the like.

The term "aralkyl" denotes an alkyl group substituted with an aryl group For example, benzyl, phenylethyl, and the like. Similarly, the term "aralkenyl" denotes an alkenyl group substituted with an aryl group, for example phenylethylenyl, and the like.

The term "heteroaryl" as used herein represents a stable five or six membered monocyclic aromatic ring system containing one to three heteroatoms independently selected from N, O or S; and any nine or ten membered bicyclic aromatic ring system containing carbon atoms and one to four heteroatoms independently selected from N, O or S. The heteroaryl group may be attached at any heteroatom or carbon atom which results in the creation of a stable structure. Examples of heteroaryl groups include, but are not limited to pyridinyl, pyrimidinyl, thienyl, furyl, imidazolyl, isoxazolyl, oxazolyl, pyrazolyl, pyrazinyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl, isoquinolinyl, purinyl. Preferred heteroaryl groups include pyrimidinyl, pyridinyl, furyl, imidazolyl, benzofuryl and thiazolyl.

The term "cycloalkyl" as used herein represents a stable three to eight membered monocyclic ring structure consisting of saturated carbon atoms. Suitable examples include cyclopropyl, cyclobutyl, cyclopentyl, cyclohexyl, cycloheptyl and cyclooctyl.

The term "heterocycloalkyl" represents a stable saturated or partially unsaturated, three to eight membered monocyclic ring structure containing carbon atoms and one to four, preferably one to two, heteroatoms independently selected from N, O or S; and any stable saturated, partially unsaturated or partially aromatic, nine to ten membered bicyclic ring system containing carbon atoms and one to four heteroatoms independently selected from N, O or S. The heterocycloalkyl may be attached at any carbon atom or heteroatom which results in the creation of a stable structure. Suitable examples of heterocycloalkyl groups include pyrrolidinyl, pyrazolidinyl, piperidinyl, piperazinyl, morpholinyl, dithianyl, trithianyl, dioxolanyl, dioxanyl, thiomorpholinyl, 3,4-methylenedioxyphenyl, 2,3-dihydrobenzofuryl, 2,3-dihydrobenzo-[1,4]-dioxin-6-yl, 2,3-dihydro-furo[2,3-b]pyridinyl, 1,2-(methylenedioxy) cyclohexane, indanyl, 2-oxa-bicyclo[2,2,1]heptanyl, and the like. Preferred heterocycloalkyl groups include piperidinyl, pyrrolidinyl, morpholinyl, indanyl, 2-oxa-bicyclo[2,2,1] heptanyl, 3,4-methylenedioxyphenyl, 2,3-dihydrobenzofuryl and 2,3-dihydrobenzo-[1,4]-dioxin-6-yl.

As used herein, the notation "*" shall denote the presence of a stereogenic center.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. It is further intended that when b or c is >1, the corresponding $R^4$ or $R^5$ substituents may be the same or different.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$–$C_6$alkylaminocarbonyl$C_1$–$C_6$alkyl" substituent refers to a group of the formula

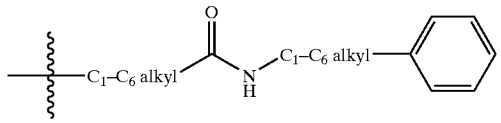

The term "sexual dysfunction" as used herein, includes male sexual dysfunction, male erectile dysfunction, impotence, female sexual dysfunction, female sexual arousal dysfunction and female sexual dysfunction related to blood flow and nitric oxide production in the tissues of the vagina and clitoris.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Abbreviations used in the specification, particularly the Schemes and Examples, are as follows:

| | |
|---|---|
| BINAP = | (R)-(+)-2,2'-Bis(diphenylphosphino)-1,1'-binaphthyl |
| Cmpd = | Compound |
| DBU = | 2,3,4,6,7,8,9,10-octahydro-pyrimido[1,2-a]azepine |
| DCC = | 1,3-Dicyclohexylcarbodiimide |
| DCM = | Dichloromethane |
| DEAD = | Diethyl diazenedicarboxylate |
| DIPEA = | Diisopropylethylamine |
| DMAP = | N,N'-Dimethyl-4-pyridinamine |
| DMF = | N,N'-Dimethylformamide |
| DMSO = | Dimethyl sulfoxide |
| dppp = | 1,3-Bis(diphenylphosphino)propane |
| EDTA = | Ethylenedinitrilotetracetic acid |
| EtOAc = | Ethyl Acetate |
| EtOH = | Ethanol |
| $Et_3N$ = | Triethylamine |
| Fmoc-NCS = | [(9H-fluoren-9-ylmethoxy)carbonyl]-thiocyanate |
| HEPES = | 2-[4-(2-hydroxyethyl)-piperazinyl]-ethanesulfonic acid |

-continued

| | |
|---|---|
| HPLC = | High Pressure Liquid Chromatography |
| ID # = | Compound Identification Number |
| KOt-Bu = | Potassium t-butoxide |
| MeOH = | Methanol |
| mCPBA = | 3-Chloroperoxybenzoic Acid |
| NaOt-Bu = | Sodium t-butoxide |
| n-Bu = | n-Butyl |
| NMP = | N-methyl-2-pyrrolidinone |
| $Pd_2dba_3$ = | Tris(dibenzylidene acetone) dipalladium(0) |
| $Pd(dppf)(OAc)_2$ = | 1,1'-bis(diphenylphosphino) ferrocene palladium diacetate |
| $Pd(OAc)_2$ = | Palladium (II) Acetate |
| $Pd(dppf)Cl_2$ = | 1,1'-Bid(diphenylphosphino) ferrocene palladium (II) dichloride |
| $Pd(PPh_3)_4$ or $Pd(Ph_3P)_4$ = | Palladium tetrakis(triphenyl phosphine) |
| Ph = | Phenyl |
| PMSF = | Phenylmethanesulfonyl fluoride |
| $PPh_3$ = | Triphenyl phosphine |
| PyBrOP = | Bromo-tris-pyrrolidino-phosphonium hexafluorophosphate |
| TEA = | Triethylamine |
| TFA = | Trifluoroacetic Acid |
| THF = | Tetrahydrofuran |
| TLC = | Thin Layer Chromatography |
| TsOH = | p-Toluenesulfonic acid |
| SNP = | Sodium Nitroprusside |

Compounds of formula (I) wherein $R^3$ is hydrogen, may be prepared according to two alternative processes from a suitably substituted compound of formula (III):

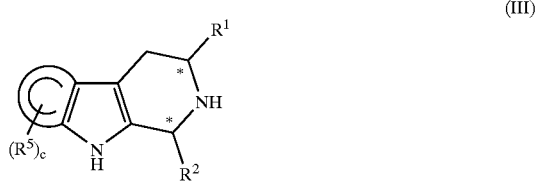

wherein $R^1$, $R^2$, $R^5$ and c are as previously defined, which is selected and used as a starting reagent.

The compound of formula (III) is a known compound or compound prepared by known methods, for example according to the process outlined in Scheme 1 below:

Scheme 1

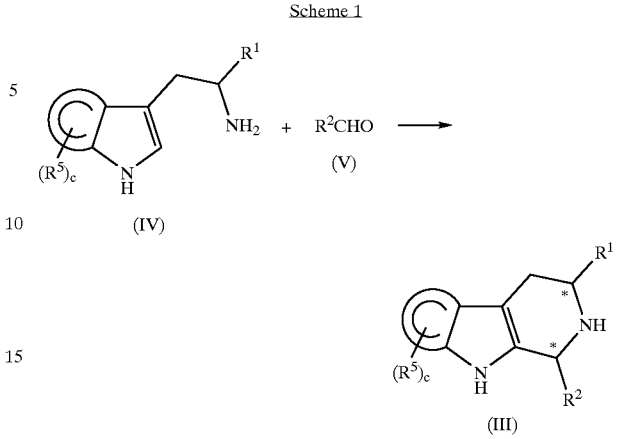

Accordingly, a compound of formula (IV), a known compound or compound produced by known methods, is reacted with a suitably substituted aldehyde of formula (V), in an organic solvent such as DCM, THF, toluene, and the like, in the presence of an acid catalyst such as TFA, tosic acid, and the like, to produce the corresponding compound of formula (III).

Generally, in the first of two alternative processes, the compounds of formula (I) may be prepared by reacting a suitably substituted compound of formula (III) to produce the corresponding substituted pyrrolopyridinone derivative. In the second process of two alternative processes, the compounds of formula (I) may be prepared by initially reacting a suitably substituted compound of formula (III) to form a tricyclic pyrrolopyridinone moiety, followed by introduction of additional substituents. This second process is particularly preferred for preparation of compounds of formula (I) wherein Y is —C(S), —C(O)O—$R^A$ or —C(O)$R^A$.

More specifically, compounds of formula (I) wherein $R^3$ is hydrogen, may be prepared from a suitably substituted compound of formula (III) according to the processes outlined in Scheme 2.

Scheme 2

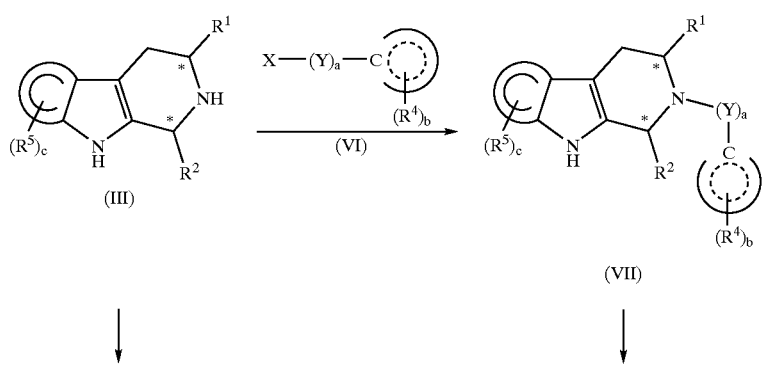

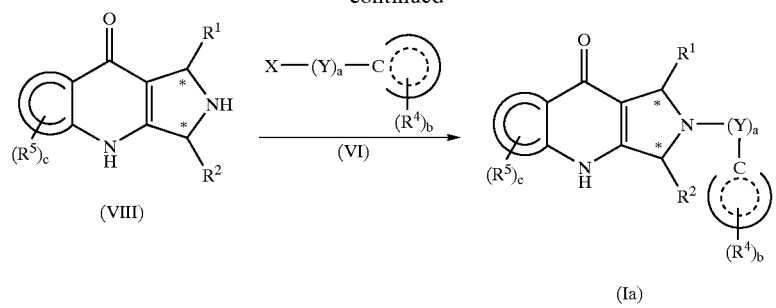

In the first process, a suitably substituted compound of formula (III) is reacted with a suitably substituted compound of formula (VI), wherein X is halogen, hydroxy, tosylate, mesylate, p-nitrophenoxide or the like, preferably X is halogen, hydroxy or p-nitrophenoxide, in an organic solvent, such as DMF, THF, DCM, toluene, and the like, to produce the corresponding compound of formula (VII). For compounds of formula (I) wherein $(Y)_a$ is $(Y)_0$ (i.e. where a is 0 such that Y is absent), the reaction mixture is preferably heated to a temperature of greater than or equal to about 100° C. For compounds of formula (I) wherein $(Y)_a$ is $(Y)_0$ (i.e. where a is 0 such that Y is absent) and

is pyridinyl, the reaction mixture is preferably catalyzed at a temperature in the range of about 30–120° C. with a catalyst such as $Pd(OAc)_2$, $Pd_2dba_3$, $Pd(dppf)Cl_2$, and the like, in an organic solvent such as 1,4-dioxane, THF, DMF, DCM, toluene, and the like, to yield the corresponding compound of formula (VII).

The compound of formula (VII) is next reacted with an oxidizing agent such as $NaIO_4$, $KO_2$, singlet oxygen, oxygen gas, ozone, and the like, preferably oxygen gas applied at about atmospheric pressure, to produce the corresponding pyrrolopyridinone derivative of formula (Ia). When the oxidizing agent is oxygen gas, the reaction is carried out in the presence of a base such as sodium hydride, potassium-t-butoxide, and the like.

In the alternative process outlined in Scheme 2, a suitably substituted compound of formula (III) is first reacted with an oxidizing agent such as $NaIO_4$, $KO_2$, singlet oxygen, oxygen gas, ozone, and the like, preferably oxygen gas applied at about atmospheric pressure, to produce the corresponding compound of formula (VIII). When the oxidizing agent is oxygen gas, the reaction is carried out in the presence of a base such as sodium hydride, potassium-t-butoxide, and the like.

The compound of formula (VIII) is next reacted with a suitably substituted compound of formula (VI), where X is halogen, hydroxy, tosylate, mesylate, p-nitrophenoxide or the like, preferably X is halogen, hydroxy or p-nitrophenoxide, in an organic solvent such as DMF, THF, DCM, toluene, and the like, optionally in the presence of a catalyst such as DMAP, to produce the corresponding substituted pyrrolopyridinone of formula (Ia). For compounds of formula (I) wherein $(Y)_a$ is $(Y)_0$ (i.e. where a is 0 such that Y is absent), the reaction mixture is preferably heated to a temperature of great than or equal to about 50° C. For compounds of formula (VIII) wherein $(Y)_a$ is $(Y)_0$ (i.e. where a is 0 such that Y is absent) and

is pyridinyl, the reaction mixture is preferably catalyzed at a temperature in the range of about 30–120° C. with catalyst such as $Pd(OAc)_2$, $Pd_2dba_3$, $Pd(dppf)Cl_2$, and the like, in an organic solvent such as 1,4-dioxane, THF, DMF, DCM, toluene, and the like, to yield the corresponding compound of formula (Ia).

Alternatively, for compounds of formula (I) wherein $(Y)_a$ is $CH_2$ and

is unsubstituted or substituted aryl or unsubstituted or substituted heteroaryl, the compound of formula (VIII) may be prepared by reacting a compound of formula (Ia) with hydrogen gas, where the hydrogen gas is applied at a pressure in the range of about atmospheric pressure to about 80 p.s.i., in the presence of a catalyst such as Pd, Pt, palladium on carbon, and the like, in an organic solvent such as methanol, ethanol, ethyl acetate, and the like. The compound of formula (VIII) may then be further functionalized as described above.

Compounds of formula (I) wherein b is 1 (i.e. wherein the group represented by

is substituted with one $R^4$ substituent) may be prepared from a suitably substituted compound of formula (III) according to three alternative processes.

In the first process, a suitably substituted compound of formula (III) is initially converted to the corresponding pyrrolopyridinone according to the process outlined in Scheme 2, followed by two step substitution at the pyrrole nitrogen, as outlined in Scheme 3.

Scheme 3

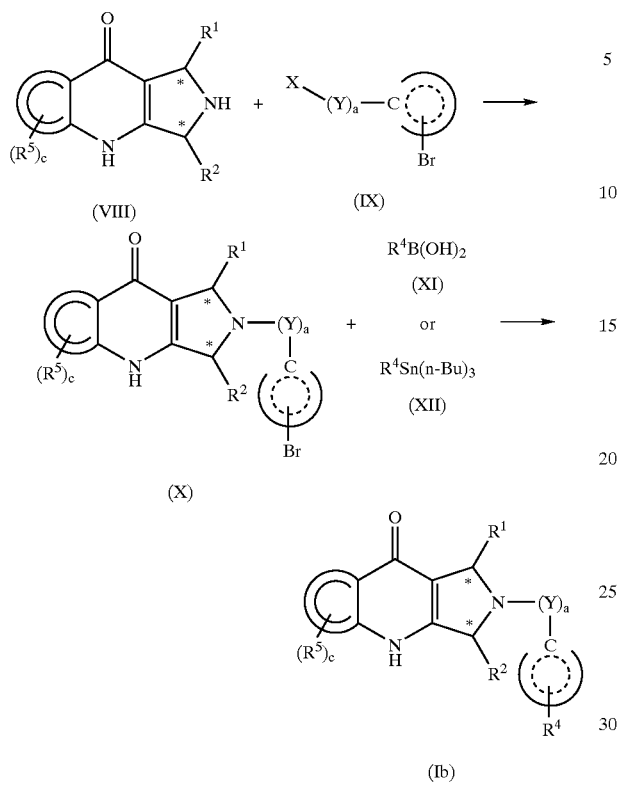

Specifically, the compound of formula (VIII) is reacted with a suitably substituted compound of formula (IX), wherein X is a halogen, in the presence of a base such as TEA, DIPEA, and the like, in an organic solvent such as DMF, DCM, THF, and the like, preferably at a temperature in the range of about 20 to about 150° C., to yield the corresponding compound of formula (X).

The compound of formula (X) is reacted with a suitably substituted boronic acid of formula (XI) or a suitably substituted tributyl-stannane of formula (XII), to yield the corresponding compound of formula (Ib). When selected reagent is a boronic acid of formula (XI), the compound of formula (X) is reacted in an organic solvent such as DMF, THF, dioxane, and the like, in the presence of a catalyst such as $Pd(Ph_3P)_4$, $Pd(dppf)(OAc)_2$, and the like, preferably at a temperature in the range of about 80–150° C. When the selected reagent is a tributyl-stannane of formula (XII), the compound of formula (X) is reacted in a solvent such as DMF, in the presence of a catalyst such as $Pd(dppf)(OAc)_2$.

In the second process, the compound of formula (III) is initially substituted with a bromo-substituted then converted to the corresponding pyrrolopyridinone, and then further substituted at the as shown in Scheme 4.

Scheme 4

More particularly, a suitably substituted compound of formula (III) is reacted with a suitably substituted compound of formula (XIII), wherein X is a halogen, in the presence of a base such as TEA, DIPEA, and the like, in an organic solvent such as DMF, toluene, and the like, preferably at a temperature in the range of about 100 to about 150° C., to yield the corresponding compound of formula (XIV).

The compound of formula (XIV) is reacted with an oxidizing agent such as $NaIO_4$, $KO_2$, singlet oxygen, oxygen gas, ozone, and the like, preferably oxygen gas applied at atmospheric pressure, to produce the corresponding compound of formula (XV).

The compound of formula (XV) is reacted with a suitably substituted boronic acid of formula (XI) or a suitably substituted tributyl-stannane of formula (XII), to yield the corresponding compound of formula (Ic). When selected reagent is a boronic acid of formula (XI), the compound of formula (XV) is reacted in an organic solvent such as DMF, dioxane, water, and the like, in the presence of a catalyst such as $Pd(Ph_3P)_4$, $Pd(dppf)(OAc)_2$, and the like, preferably at a temperature in the range of about 80 to about 160° C. When the selected reagent is a tributyl-stannane of formula (XII), the compound of formula (XV) is reacted in a solvent such as DMF, TEA, and the like, in the presence of a catalyst such as $Pd(dppf)(OAc)_2$.

In the third process, the compound of formula (III) is initially substituted with a bromo-substituted

, further substituted at the

with the $R^4$ substituent, and then converted to the corresponding pyrrolopyridinone, as shown in Scheme 5.

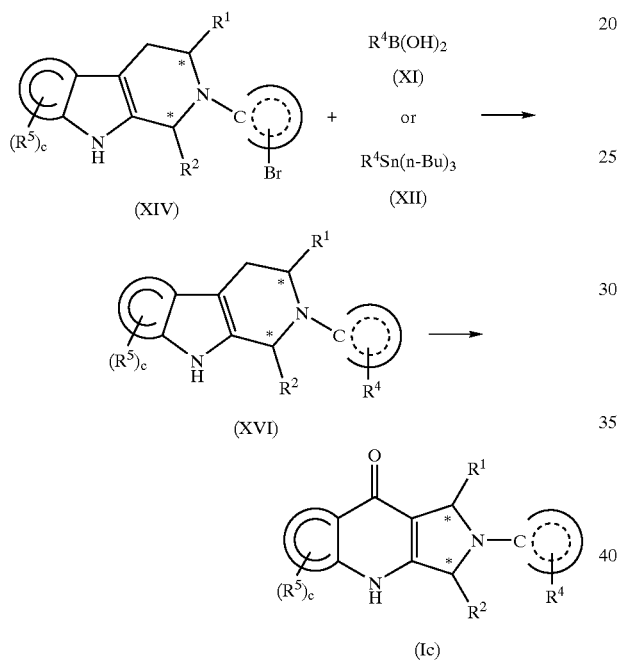

More particularly, the compound of formula (XIV) is reacted with a suitably substituted boronic acid of formula (XI) or a suitably substituted tributyl-stannane of formula (XII), to yield the corresponding compound of formula (XVI). When selected reagent is a boronic acid of formula (XI), the compound of formula (XIV) is reacted in an organic solvent such as DMF, dioxane, water, and the like, in the presence of a catalyst such as $Pd(Ph_3P)_4$, $Pd(dppf)(OAc)_2$, and the like, preferably at a temperature in the range of about 80 and about 120° C. When the selected reagent is a tributyl-stannane of formula (XII), the compound of formula (XIV) is reacted in a solvent such as DMF, dioxane, and the like, in the presence of a catalyst such as $Pd(dppf)(OAc)_2$.

The compound of formula (XVI) is reacted with an oxidizing agent such as $NaIO_4$, $KO_2$, singlet oxygen, oxygen gas, ozone, and the like, preferably oxygen gas applied at atmospheric pressure, to produce the corresponding compound of formula (Ic).

Compounds of formula (I) wherein b is an integer selected from 2, 3 and 4, (i.e. wherein the

is substituted with 2, 3 or 4 $R^4$ groups) may similarly be prepared according to the processes outlined in Schemes 3, 4 and 5, with appropriate substitution of the

containing reagent with the corresponding reagent wherein the

is substituted with 2, 3 or 4 bromine groups, which bromine groups are sequentially reacted to incorporate the desired $R^4$ groups.

Compounds of formula (I) wherein $(Y)_a$ is C(O) may be prepared according to two alternative processes. In the first process, a pyrrolopyridinone compound of formula (VIII) is initially substituted with a suitably selected carboxylic acid or acid chloride, followed by further substitution of the

with the $R^4$ substituent, as outlined in Scheme 6.

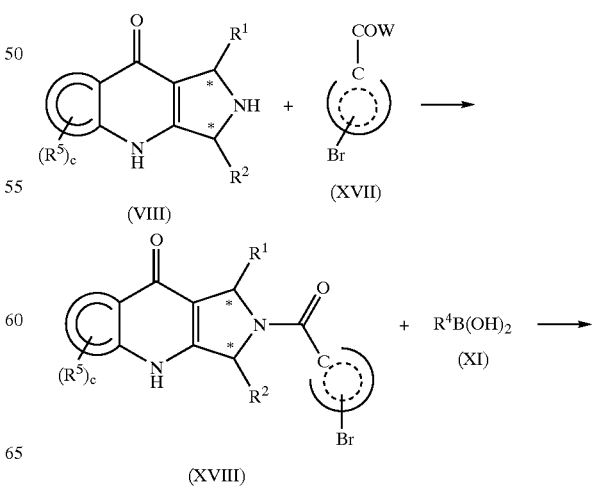

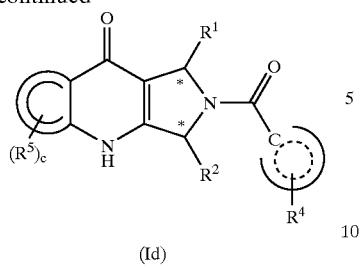

(Id)

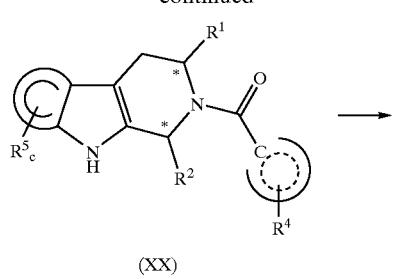

(XX)

More particularly, a suitably substituted pyrrolopyridinone compound of formula (VIII) is reacted with a suitably substituted carboxylic acid or acid chloride of formula (XVIII), wherein W is OH or Cl, in an organic solvent such as DMF, THF, dioxane, and the like, and when W is OH in the presence of a catalyst such as PyBrop, DCC, and the like, and when W is Cl in the presence of a base such as TEA, DIPEA, and the like, preferably at a temperature in the range of about 0 to about 30° C., to yield the corresponding compound of formula (XVIII).

The compound of formula (XVIII) is reacted with a suitably substituted boronic acid of formula (XI), in an organic solvent such as DMF, dioxane, water, and the like, in the presence of a catalyst such as Pd(Ph$_3$P)$_4$, and the like, preferably at a temperature in the range of about 80 to about 120° C., to yield the corresponding compound of formula (Id).

In the second process, a suitably substituted compound of formula (III) is initially converted to the corresponding pyrrolopyridinone, followed by two step substitution using a suitable selected carboxylic acid, followed by boronic acid or stannane, as outlined in Scheme 7.

Scheme 7

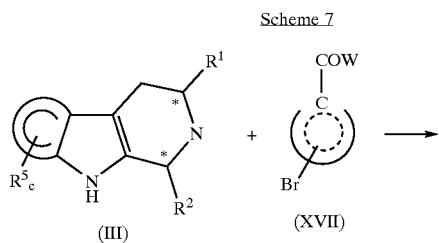

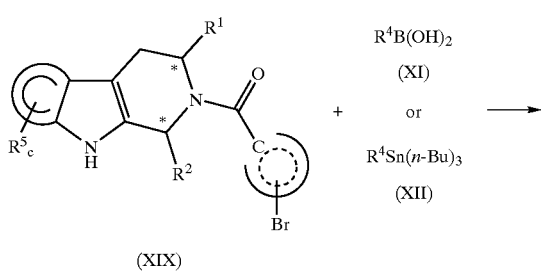

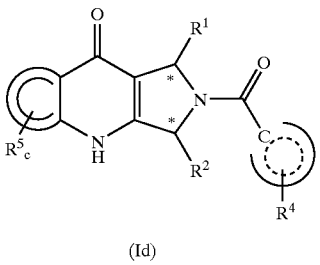

(Id)

More particularly, a suitably substituted compound of formula (III) is reacted with a suitably substituted carboxylic acid of formula (XVII), wherein W is halogen or hydroxy, in an organic solvent such as TEA, DIPEA, and the like, preferably at a temperature in the range of about 80 to about 130° C., to yield the corresponding compound of formula (XIX).

The compound of formula (XIX) is reacted with a suitably substituted boronic acid of formula (XI) or a suitably substituted tributyl-stannane of formula (XII), to yield the corresponding compound of formula (XX). When selected reagent is a boronic acid of formula (XI), the compound of formula (XIX) is reacted in an organic solvent such as DMF, dioxane, water, and the like, in the presence of a catalyst such as Pd(Ph$_3$P)$_4$, Pd(dppf)(OAc)$_2$, and the like, preferably at a temperature in the range of about 80 to about 120° C. When the selected reagent is a tributyl-stannane of formula (XII), the compound of formula (XIX) is reacted in a solvent such as DMF, dioxane, and the like, in the presence of a catalyst such as Pd(dppf)(OAc)$_2$.

The compound of formula (XX) is reacted with an oxidizing agent such as NaIO$_4$, KO$_2$, singlet oxygen, oxygen gas, ozone, and the like, preferably KO$_2$, to produce the corresponding compound of formula (Id).

Compounds of formula (I), wherein R$^3$ is other than hydrogen, and compounds of formula (II), may be prepared according to the process outlined in Scheme 8.

Scheme 8

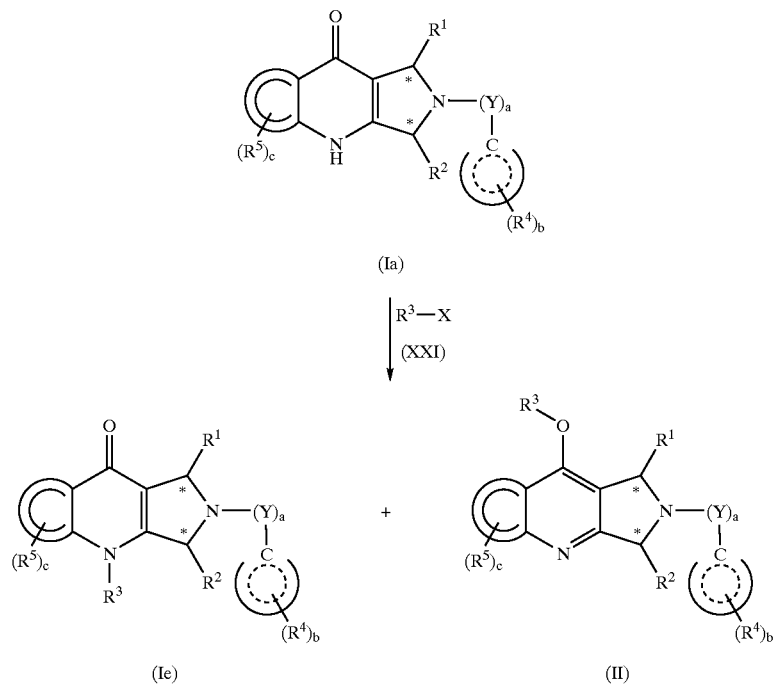

More specifically, a compound of formula (Ia) is reacted with a suitably substituted compound of formula (XXI), where X is halogen, hydroxy, tosylate, mesylate, and the like, preferably X is halogen, in an organic solvent such as THF, DMF, dichloromethane, toluene, and the like, preferably THF or DMF, to yield a mixture of the corresponding substituted compound of formula (Ie) and the corresponding substituted compound of formula (II). When in the compound of formula (XXI), X is halogen, the reaction is preferably carried out in the presence of an organic or inorganic base such as triethylamine, diisopropylethylamine, potassium carbonate, sodium hydride, sodium hydroxide and the like.

The compounds of formula (Ie) and (II) are preferably separated by known methods such as recrystallization, column chromatography, HPLC, and the like.

Compounds of formula (VII) wherein $Y_a$ is $Y_0$ (i.e. wherein Y is absent) and

is 2-(4-substituted)thiazolyl, may be prepared according to a process as outlined in Scheme 9.

SCHEME 9

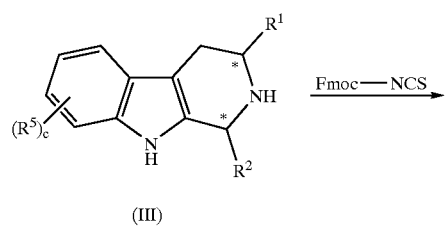

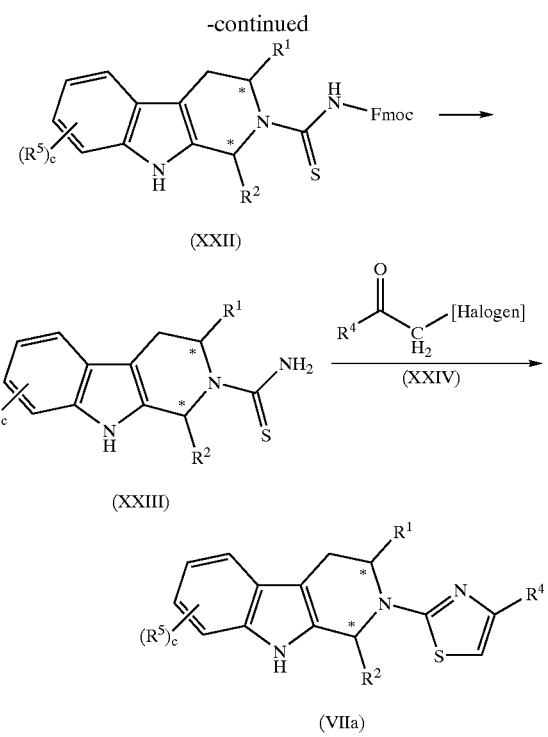

Accordingly, a suitably substituted compound of formula (III) is reacted with Fmoc-NCS, in an organic solvent such as DCM, DMF, THF, and the like, preferably at room temperature, to produce the corresponding compound of formula (XXII).

The compound of (XXII) is reacted with 20% piperidine, in an alcohol such as methanol, ethanol, and the like, to produce the corresponding amine of formula (XXIII).

The amine of formula (XXIII) is reacted with a suitably substituted α-halo methyl ketone of formula (XXIV), in the presence of an organic solvent or mixture such as DMF, ethanol:dioxane, and the like, in the presence of a base such as TEA, DIPEA, and the like, preferably at a temperature of about 70° C., to produce the corresponding compound of formula (VIIa).

Specific diastereomers of the compounds of formula (I), more particularly compounds of formula (I) wherein $R^1$ is hydrogen and an R-configuration at the chiral center of the $R^2$ bond to the pyrrolopyridinone is desired, may be prepared according to the process outlined in Scheme 10.

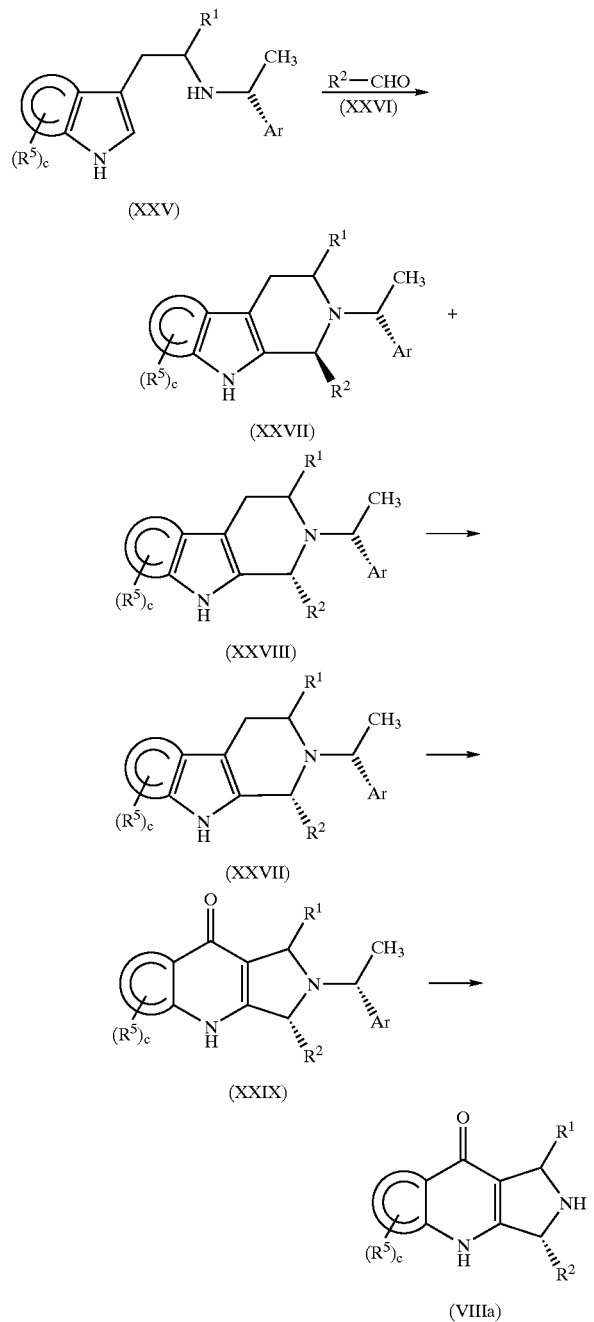

Accordingly, a suitably substituted compound of formula (XXV), a known compound or compound prepared by known methods, wherein $R^1$ is hydrogen and Ar is an aryl group, preferably naphthyl, more preferably 1-naphthyl, is reacted with a suitably substituted aldehyde, a compound of formula (XXVI), in an organic solvent such as p-xylene, o-xylene, toluene, DCM, and the like, at a temperature in the range of about 25–270° C., under aprotic or protic conditions, to yield a mixture of the corresponding diastereomers, compounds of formula (XXVII) and (XXVIII).

The R-diastereomer, the compound of formula (XXVII) is separated from the compound of formula (XXVIII) by recrystallization or silica gel chromatography.

The compound of formula (XXVII) (the S-diastereomer) is converted to the desired R-diastereomer, the compound of formula (XXVIII), by stirring the compound of formula (XXVII) in an acid such as TFA, HCl, TsOH, and the like, in the presence of an organic solvent such as $CH_2Cl_2$, DCM, 1m4-dioxane, and the like, to yield the desired R-diastereomer, the compound of formula (XXVIII).

The compound of formula (XXVIII) is reacted with an oxidizing agent such as oxygen gas, singlet oxygen, $KO_2$, $NaIO_4$, ozone, and the like, preferably oxygen gas at about atmospheric pressure, to yield the corresponding compound of formula (XXIX). When the oxidizing agent is oxygen gas, the reaction is carried out in the presence of a base such as sodium hydride, potassium-t-butoxide, and the like, in an organic solvent such as DMF, DMSO, NMP, and the like.

The compound of formula (XXIX) is reacted with a reducing agent such as hydrogen gas, in the presence of a catalyst such as palladium on carbon, in a polar solvent such as methanol, ethanol, and the like, to yield the corresponding compound of formula (VIIIa).

The compound of formula (VIIIa) may then be further reacted to yield the corresponding compound of formula (I) according to the process outlined in Scheme 3 above.

For compounds of formula (I), wherein $R^1$ is other than hydrogen, a second chiral center will exist at the bond of the $R^1$ group to the pyrrolopyridinone. If a specific orientation of the $R^1$ group is present in the starting reagent, the compound of formula (XXV) in Scheme 10 above, its orientation will impact the conversion of diastereomers.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared by enantioselective synthesis, by resolution or from enantiomerically enriched reagents. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters, amides or amines, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds to treat sexual dysfunction can be determined according to the procedures described in Example 95, 96 and 97 herein.

The present invention therefore provides a method of treating sexual dysfunction, more particularly male erectile dysfunction in a subject in need thereof which comprises administering any of the compounds as defined herein in a quantity effective to treat ED. The compound may be administered to a patient by any conventional route of administration, including, but not limited to, intravenous, oral, subcutaneous, intramuscular, intradermal and parenteral. The quantity of the compound which is effective for treating ED is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating sexual dysfunction, more particularly male erectile dysfunction described in the present invention may also be carried out using a pharmaceutical composition comprising any of the compounds as defined herein and a pharmaceutically acceptable carrier. The pharmaceutical composition may contain between about 1 mg and 1000 mg, preferably about 1 to 200 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of sexual dysfunction, more particularly male erectile dysfunction is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.1 mg/kg to about 3 mg/kg of body weight per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter. Unless otherwise indicated, $^1$H NMRs were run on a Bruker instrument.

EXAMPLE 1

1-(3,4-Methylenedioxyphenyl)-2-benzyl-2,3,4,9-tetrahydro-1H-β-carboline

To a solution of the 1-(3,4-methylenedioxyphenyl)-2,3,4,9-tetrahydro-1H-β-carboline (prepared according to the process as disclosed in WO97/43287, Intermediate 7, page 24) (7.37 g, 25 mmol) in dry DMF (25 mL) was added triethylamine (3.52 mL, 25 mmol) and benzyl bromide (3.00 mL, 25 mmol). The mixture was stirred at ambient temperature overnight and added dropwise to a solution of sodium hydroxide (25 mmol) in water (200 mL). A precipitate was formed, collected by vacuum filtration, washed with water (2×50 mL), and dried in vacuo overnight to yield the product as a freely flowing pale yellow powder.

MS (m/z) 383 (MH$^+$).

$^1$H NMR (CDCl$_3$) δ 2.57–2.89 (series of m, 3H), 3.18–3.23 (m, 1H), 3.33 (d, J=13.7 Hz, 1H), 3.63 (d, J=13.7 Hz, 1H), 4.55 (s, 1H), 5.94 (nd, J=2.2 Hz, 2H), 6.77–7.52 (series of m, 13H).

EXAMPLE 1A (R)-1-(3,4-Methylenedioxyphenyl)-2-benzyl-2,3,4,9-tetrahydro-1H-β-carboline Following the procedure as described in Example 1, (R)-1-(3,4,-methylenedioxyphenyl)-2,3,4,9-tetrahydro-1H-β-carboline was reacted to produce the title compound.

MS (m/z) 383 (MH$^+$).

EXAMPLE 2

1-(2,3-Dihydrobenzofuran-5-yl)-2-benzyl-2,3,4,9-tetrahydro-1H-β-carboline

The title product was prepared according to the process described in Example 1 using 1-(2,3-dihydrobenzofuran-5-yl)-2,3,4,9-tetrahydro-1H-β-carboline as the starting reagent.

MS (m/z) 381 (MH$^+$).

$^1$H NMR (CDCl$_3$) δ 2.59–2.90 (series of m, 3H), 3.13–3.24 (m, 3H), 3.33 (d, J=13.5 Hz, 1H), 3.93 (d, J=13.5 Hz, 1H), 4.56 (t, J=8.6 Hz, 2H), 6.75 (d, J=8.1 Hz, 1H), 7.05–7.35 (series of m, 10H), 7.49–7.52 (m, 1H).

EXAMPLE 2A (R)-1-(2,3-Dihydrobenzofuran-5-yl)-2-benzyl-2,3,4,9-tetrahydro-1H-β-carboline Following the procedure as described in Example 2, (R)-1-(2,3-dihydrobenzofuran-5-yl)-2,3,4,9-tetrahydro-1H-β-carboline was reacted to produce the title compound.

MS (m/z) 381 (MH$^+$).

[α}=−56.9° (c=0.62, CH$_3$OH).

EXAMPLE 3

1,2,3,4-Tetrahydro-2-benzyl-3-(3,4-methylenedioxyphenyl)-9H-pyrrolo-[3,4-b]quinolin-9-one (#54)

1-(3,4-Methylenedioxyphenyl)-2-benzyl-2,3,4,9-tetrahydro-1H-β-carboline (0.79 g, 2.0 mmol) (prepared as in Example 1) was dissolved in dry DMF (15 mL). Potassium t-butoxide (0.56 g, 5.0 mmol) was added, followed by oxygen, bubbled in via syringe needle. The mixture was maintained at room temperature for one hour and then poured onto a mixture of 1N HCl (5 mL), water (35 mL) and ethyl acetate (35 mL). A fluffy yellow precipitate was collected, the organic layer removed, and the aqueous solution extracted with ethyl acetate (15 mL). The extracted layer was agitated and set aside overnight. The following day an additional quantity of product (as a precipitate) was collected. Drying of the combined solids yielded the product as a yellow powder.

MS (m/z): 397 (MH$^+$).

$^1$H-NMR (DMSO-d6) δ 3.52 (dd, J=11.9, 3 Hz, 1H), 3.63 (d, J=13.2 Hz, 1H), 3.84 (d, J=13.2 Hz, 1H), 3.93 (dd, J=11.9, 3 Hz, 1H), 5.10 (s, 1H), 6.05 (nd, J=3.4 Hz, 2H), 6.98 (s, 3H), 7.26–7.36 (m, 6H), 7.54–7.59 (m, 2H), 8.10 (d, J=8 Hz, 1H), 11.42 (s, 1H).

EXAMPLE 3A (R)-1,2,3,4-Tetrahydro-2-benzyl-3-(3,4-methylenedioxyphenyl)-9H-pyrrolo-[3,4-b]quinolin-9-one (#67)

Following the procedure as described in Example 3, (R)-1-(3,4-Methylenedioxyphenyl)-2-benzyl-2,3,4,9- tetrahydro-1H-β-carboline was reacted to produce the title compound.

MS (m/z) 397 (MH$^+$).

EXAMPLE 4

1,2,3,4-Tetrahydro-2-benzyl-3-(2,3-dihydrobenzofuran-5-yl)-9H-pyrrolo-[3,4-b]quinolin-9-one (#60)

1-(2,3-Dihydrobenzofuran-5-yl)-2-benzyl-2,3,4,9-tetrahydro-1H-β-carboline (prepared as in Example 2) (3.10 g, 8.15 mmol) was dissolved in dry DMF (20 mL). Potassium t-butoxide (2.29 g, 20.38 mmol) was added, followed by oxygen, bubbled in via syringe needle. The solution was stirred for 1.5 h. To the reaction mixture was added a solution of HCl in ether (10 mL, 2M) and the solution dripped into rapidly stirring water. The resulting suspension was stirred overnight. A brown solid was filtered off and washed with water. The filtrate was neutralized with 1N NaOH, resulting in a yellow precipitate. The solid was filtered, washed with water, dried briefly, and partially dissolved in THF/methanol. The precipitate solid was filtered and washed with ether to yield the product as a pale yellow solid.

MS (m/z) 395 (MH$^+$).

$^1$H NMR (DMSO-d6) δ 3.19 (t, J=8.7 Hz, 2H), 3.53 (d, J=11.8 Hz, 1H), 3.61 (d, J=12.2 Hz, 1H), 3.82 (d, J=12.2 Hz, 1H), 3.92 (d, J=11.8 Hz, 1H), 4.55 (t, J=8.7 Hz, 2H), 5.08 (s, 1H), 6.81 (d, J=8.1 Hz, 1H), 7.16–7.59 (series of m, 9H), 8.10 (d, J=8.1 Hz, 1H), 11.42 (s, 1H).

EXAMPLE 4A (R)-1,2,3,4-Tetrahydro-2-benzyl-3-(2,3-dihydrobenzofuran-5-yl)-9H-pyrrolo-[3,4-b]quinolin-9-one (#77)

Following the procedure as described in Example 4, (R)-1-(2,3-Dihydrobenzofuran-5-yl)-2-benzyl-2,3,4,9-tetrahydro-1H-β-carboline was reacted to produce the title compound.

MS (m/z) 395 (MH$^+$).

[α]=−110.0° (c=0.43, CH$_3$OH); HPLC Chiralpak OD 0.46×25 cm, 0.1% DEA/MeOH, Tr=5.360 min.

EXAMPLE 5

1,2,3,4-Tetrahydro-3-(3,4-methylenedioxyphenyl)-9H-pyrrolo-[3,4-b]quinolin-9-one, hydrochloride salt (#4)

Method A: HCl Salt

To a suspension of 1,2,3,4-tetrahydro-2-benzyl-3-(3,4-methylenedioxyphenyl)-9H-pyrrolo-[3,4-b]quinolin-9-one (prepared as in Example 3) (1.12 g, 2.82 mmol) in methanol (50 mL) and 10% Pd/C (500 mg) was added HCl in ether solution (1.41 mL, 2N). The reaction mixture was agitated under a hydrogen atmosphere (45 psi) in a Parr apparatus for 6 h. The resulting solution was filtered through Celite and concentration in vacuo to yield the product as a green solid.

MS (m/z) 307 (MH$^+$).

$^1$H NMR (DMSO-d6) δ 4.39–4.48 (m, 2H), 6.09 (broad s, 3H), 6.97–7.05 (m, 3H), 7.40 (t, J=7.1 Hz, 1H), 7.60–7.71 (m, 2H), 8.17 (d, J=8.0 Hz, 1H), 9.68 (s, 1H), 11.13 (s, 1H).

Method B: Free Base 1-(3,4-methylenedioxyphenyl)-2,3,4,9-tetrahydro-1H-β-carboline, a known compound, (prepared according to the process as disclosed in WO97/43287, Intermediate 7, page 24) (15.35 g, 52.5 mmol) was dissolved in dry DMF (90 mL). Potassium tert-butoxide (10.02 g, 89.3 mmol) was introduced in one portion and the suspension was stirred until a clear solution was obtained. Oxygen gas was then passed through the solution via a syringe needle for 50 min. The reaction was quenched by the addition of glacial acetic acid (5.11 mL, 89.3 mmol) and poured into diethyl ether (1 L), which resulted in a precipitate that was collected by filtration. The product was purified by flash chromatography (0–50% EtOH/THF) to yield the product as a yellow powder.

MS (m/z): 307 (MH$^+$).

$^1$H-NMR (CD$_3$OD) δ 4.18 (d, J=13.7 Hz, 1H), 4.36 (d, J=13.7 Hz, 1H), 4.92 (broad s, 2H), 5.43 (s, 1H), 5.92 (s, 1H), 6.74 (s, 1H), 6.81 (s, 1H), 7.36–7.70 (series of m, 4H), 8.31 (d, J=8.6 Hz, 1H).

EXAMPLE 5A (R)-1,2,3,4-Tetrahydro-3-(3,4-methylenedioxyphenyl)-9H-pyrrolo-[3,4-b]quinolin-9-one, hydrochloride salt (#48)

Following the procedure as described in Example 5, Method A, (R)-1,2,3,4-tetrahydro-2-benzyl-3-(3,4-methylenedioxyphenyl)-9H-pyrrolo-[3,4-b]quinolin-9-one was reacted to produce the title compound.

MS (m/z) 307 (MH$^+$).

EXAMPLE 6

1,2,3,4-Tetrahydro-3-(2,3-dihydrobenzofuran-5-yl)-9H-pyrrolo-[3,4-b]quinolin-9-one, hydrochloride salt Method A: HCl Salt The title product was prepared according to the process described in Example 4 with substitution of appropriate reagents.

MS (m/z) 305 (MH$^+$).

$^1$H NMR (DMSO-d6) δ 3.17–3.20 (m, 2H), 4.38–4.60 (m, 4H), 6.10 (s, 1H) 6.85 (d, J=8.2 Hz, 1H), 7.21 (d, J=8.1 Hz, 1H), 7.30 (s, 1H), 7.40 (t, J=7.1 Hz, 1H), 7.61 (t, J=8.2 Hz, 1H), 7.68(d, J=7.2 Hz, 1H), 8.17 (d, J=8.9 Hz, 1H), 9.71 (s, 1H), 11.17 (s, 1H).

Method B: Free Base 1-(2,3-dihydro-5-benzofuranyl)-2,3,4,9-tetrahydro-1H-β-carboline (1.06 g, 3.64 mmol), a known compound, (prepared according to the process as disclosed in WO97/43287, Intermediate 10, page 25) was dissolved in dry DMF (8 mL). Potassium tert-butoxide (829 mg, 7.38 mmol) was introduced in one portion and the suspension was stirred until a clear solution was obtained. Oxygen gas was then passed through the solution via a syringe needle for 50 min. The reaction was quenched by the addition of glacial acetic acid (0.42 mL, 7.34 mmol) and poured into diethyl ether (50 mL), which resulted in a precipitate that was collected by filtration. The product was purified by flash chromatography (0–50% MeOH/THF) to yield the product as a yellow powder.

MS (m/z): 305 (MH$^+$).

$^1$H-NMR (CD$_3$OD) δ 3.17 (t, J=8.7 Hz, 2H), 3.29–3.31 (m, 2H), 4.18 (d, J=12.9 Hz, 1H), 4.38 (d, J=12.9 Hz, 1H), 4.53 (t, J=8.7 Hz, 2H), 5.44 (s, 1H), 6.74 (d, J=8.2 Hz, 1H), 7.07 (d, J=8.2 Hz, 1H), 7.13 (s, 1H), 7.40 (t, J=7.9 Hz, 1H), 7.54 (d, J=8.3 Hz, 1H), 7.65 (t, J=7.9 Hz, 1H), 8.29 (d, J=8.1 Hz, 1H).

EXAMPLE 6A (R)-1,2,3,4-Tetrahydro-3-(2.3-dihydrobenzofuran-5-yl)-9H-pyrrolo-[3,4-b]quinolin-9-one, hydrochloride salt Following the procedure as described in Example 6, Method A, (R)-1,2,3,4-tetrahydro-2-benzyl-3-(2,3- dihydrobenzofuran-5-yl)-9H-pyrrolo-[3,4-b]quinolin-9-one was reacted to produce the title compound.

MS (m/z) 305 (MH+).

[α]=+39.0° (C=0.605, 1% TFA in CH$_3$OH).

EXAMPLE 7

(4-Pyridinyl)methyl-4-nitrophenylcarbonic acid ester

To a solution of 4-pyridinylcarbinol (50 mmol) and triethylamine (50 mmol) in dry dichloromethane (100 mL) was added a solution of 4-nitrophenylchloroformate (50 mmol). The reaction mixture was stirred overnight at ambient temperature, resulting in a yellow precipitate which was removed by filtration, and concentrated. The semisolid residue was treated with THF (50 mL) to form a white precipitate. The precipitate was collected by filtration, concentrated and purified by flash chromatography (20% THF/CHCl$_3$) to yield the product as an orange solid.

MS (m/z) 275 (MH+).

$^1$H NMR (CDCl$_3$) δ 5.33 (s, 2H), 7.36 (d, J=5.8 Hz, 2H), 7.41 (d, J=9.4 Hz, 2H), 8.30 (d, J=9.4 Hz, 2H), 8.68 (d, J=5.8 Hz, 2H).

EXAMPLE 8

6-[2-(1-Morpholino)ethoxy]-2-benzofurancarboxylic acid

A solution of 6-methoxy-2-benzofurancarboxylate methyl ester (868 mg, 4.52 mmol) in dry benzene was treated with triphenylphosphine (1.18 g, 4.52 mmol) and 1-(2-hydroxyethyl)-morpholine (0.72 mL, 4.57 mmol) under an argon atmosphere. DEAD (0.55 mL, 4.5 mmol) was added dropwise to the reaction mixture, at room temperature. The solution was stirred overnight, concentrated in vacuo and the residue purified by flash chromatography (0–10% MeOH/CHCl$_3$).

The purified product was subjected to saponification for 3 h in a 1:1 mixture of methanol and aqueous 1N NaOH (80 mL) at reflux temperature. The reaction mixture was neutralized with concentrated HCl and concentrated to yield a residue which was triturated with methanol (20 mL). The resulting salt was removed by filtration and concentrated to yield a second residue that was similarly triturated with THF. The third residue was dried under vacuum to yield the product as a yellow powder.

MS (m/z) 292 (MH+).

$^1$H NMR (DMSO-d6) δ 2.57 (broad s, 4H), 2.87 (t, J=5.3 Hz, 2H), 3.64 (t, J=4.6 Hz, 4H), 4.23 (t, J=5.5 Hz, 2H), 6.97 (dd, J=8.7, 2 Hz, 1H), 7.31 (s, 1H), 7.53 (s, 1H), 7.63 (d, J=8.7 Hz, 1H).

EXAMPLE 9

1-(3,4-Methylenedioxyphenyl)-2-(tert-butoxycarbonyl]-2,3,4,9-tetrahydro-1H-β-carboline To a suspension of 1-(3,4-methylenedioxyphenyl)-2,3,4,9-tetrahydro-1H-β-carboline (27.7 g, 94.8 mmol) (prepared according to the process as disclosed in WO97/43287, Intermediate 7, page 24) in dry methanol (300 mL) was added t-butylpyrocarbonate (25.0 g, 114 mmol). Shortly after the addition of the pyrocarbonate, a clear solution was formed. The solution was stirred at ambient temperature for 1 h, resulting in formation of a white precipitate. The solid was collected by filtration, washed with a 1:1 mixture of diethyl ether:pentane, and dried in vacuo to yield the product as a white solid.

MS (m/z): 415 (MNa+).

$^1$H-NMR (CDCl$_3$) δ 1.53 (s, 9H), 2.75–3.17 (series of m, 3H), 4.22 (broad, 1H), 5.93 (s, 2H), 6.31 (broad, 1H), 6.64–6.72 (m, 2H), 6.80 (s, 1H), 7.12–7.33 (series of m, 3H), 7.54 (d, J=7.7 Hz, 1H), 7.93 (broad, 1H).

EXAMPLE 10

1-(3,4-Methylenedioxyphenyl)-2-(benzyloxycarbonyl)-2,3,4,9-tetrahydro-1H-β-carboline To a solution of 1-(3,4-methylenedioxyphenyl)-2,3,4,9-tetrahydro-1H-β-carboline (9.11 g, 31.1 mmol) (prepared according to the process as disclosed in WO97/43287, Intermediate 7, page 24) in dry dichloromethane (100 mL) were added triethylamine (8.80 mL, 63.1 mmol) and dimethylaminopyridine (5 mg), followed by the dropwise addition of benzylchloroformate (4.60 mL, 30.6 mmol) over a period of 30 min. The reaction mixture was stirred for 16 h, transferred to a separatory funnel, washed with 2N HCl, brine, dried over anhydrous magnesium sulfate and concentration in vacuo. Flash chromatography yielded the product as a white solid.

MS (m/z): 425 (M−1).

$^1$H-NMR (CDCl$_3$) δ 2.78–2.95 (broad m, 2H), 3.15–3.25 (m, 1H), 4.40 (broad, 1H), 5.14 (d, J=12.3 Hz, 1H), 5.22 (d, J=12.3 Hz, 1H), 5.90 (s, 2H), 6.35 (broad 1H), 6.80 (broad, 3H), 7.09–7.35 (series of m, 8H), 7.53 (d, J=7.6 Hz, 1H), 7.70 (broad, 1H).

EXAMPLE 11

1-(3,4-Dimethoxyphenyl)-2,3,4,9-tetrahydro-1H-β-carboline

To a solution of tryptamine (5.0 g, 0.0312 mol) and 3,4-dimethoxy benzaldehyde (5.7 g, 0.0312 mol) in CH$_2$Cl$_2$ (220 mL) was added TFA (4.5 mL, 0.0584 mol). The deep blue solution was stirred at room temperature for 20 h. The reaction mixture was neutralized with NaHCO$_3$ (4.9 g, 0.0584 mol) in H$_2$O (50 mL) and the organic layer washed with brine (2×100 mL). The reaction mixture was dried with MgSO$_4$ and the solvent evaporated. Product was isolated by column chromatography (silica gel; CH$_3$OH:EtOAc=1:9) as a yellowish oil, which solidified slowly upon standing at room temperature.

mp: 146–148° C.; MS (m/z) 307 (M−1), 309 (MH+).

$^1$H NMR (CDCl$_3$) δ 2.70–2.92 (m, 2H), 3.05 (m, 1H), 3.31 (m, 1H), 3.65 (s, 3H), 3.81 (s, 3H), 5.01 (s, 1H), 6.72 (m, 2H), 7.12 (m, 3H), 7.52 (m, 1H), 8.18 (s, 1H).

EXAMPLE 12

1-(3,4-Methylenedioxyphenyl)-2-[5-(4-methoxyphenyl)-pyrimidin-2-yl]-2,3,4,9-tetrahydro-1H-β-carboline 1-(3,4-methylenedioxyphenyl)-2,3,4,9-tetrahydro-1H-β-carboline (2.72 g, 9.6 mmol) (prepared according to the process as disclosed in WO97/43287, Intermediate 7, page 24) and 2-chloro-5-(4-methoxyphenyl)pyrimidine (1.04 g, 4.78 mmol) were stirred in DMF (20 mL, anhydrous) at 120° C. for 16 h. The resulting mixture was quenched with saturated NH$_4$Cl, extracted with ethyl acetate and dried with MgSO$_4$. The reaction mixture solvent was evaporated and the residue purified by column chromatography (silica gel, ethyl acetate:hexanes=1:2) to yield the product as a white solid.

mp: 200–202° C.; MS (m/z): 477 (MH$^+$).

$^1$H-NMR (DMSO-d$_6$) δ 2.71 (m, 2H), 3.25 (m, 1H), 3.78 (s, 3H), 4.93 (d, J=12 Hz, 1H), 5.99 (d, J=5 Hz, 2H), 6.76 (d, J=8 Hz, 1H), 6.87 (d, J=8 Hz, 2H), 7.02 (d, J=9 Hz, 2H), 7.06 (d, J=7 Hz, 1H), 7.11 (s, 1H), 7.31 (d, J=8 Hz, 1H), 7.46 (d, J=8 Hz, 1H), 7.59 (d, J=9 Hz, 2H), 8.74 (s, 2H), 11.00 (s, 1H).

EXAMPLE 13

1-(3,4-Methylenedioxyphenyl)-2-[5-(3,4-dimethoxyphenyl)-pyrimidin-2-yl]-2,3,4,9-tetrahydro-1H-β-carboline Following the same procedure as outlined in Example 12, 1-(3,4-methylenedioxyphenyl)-2,3,4,9-tetrahydro-1H-β-carboline (3.73 g, 12.8 mmol) (prepared according to the process as disclosed in WO97/43287, Intermediate 7, page 24) and 2-chloro-5-(3,4-dimethoxylphenyl)pyrimidine (1.60 g, 6.4 mmol) in DMF (50 mL, anhydrous) were reacted to yield the product as a white solid.

mp: 173–175° C.; MS (m/z): 507 (MH$^+$).

$^1$H-NMR (CDCl$_3$) δ 2.89 (d, J=15 Hz, 1H), 3.02 (m, 1H), 3.39 (m, 1H), 3.92, 3.94 (2s, 6H), 5.03 (d, J=12 Hz, 1H), 5.92 (d, J=4 Hz, 2H), 6.71 (d, J=7 Hz, 1H), 6.87–7.32 (m, 6H), 7.56 (d, J=7 Hz, 2H), 7.80 (s, 1H), 8.56 (s, 2H);

EXAMPLE 14

1-(3,4-Methlenedioxyphenyl)-2-[5-(4-methylphenyl)-pyrimidin-2-yl]-2,3,4,9-tetrahydro-1H-β-carboline Following the same procedure as outlined in Example 12, 1-(3,4-methylenedioxyphenyl)-2,3,4,9-tetrahydro-1H-β-carboline (2.19 g, 7.5 mmol) (prepared according to the process as disclosed in WO97/43287, Intermediate 7, page 24) and 2-chloro-5-(4-methylphenyl)pyrimidine (1.03 g, 5 mmol) in toluene (50 mL, anhydrous) and DBU (0.9 mL) were reacted to yield the product as a white solid.

MS (m/z): 459 (MH$^+$).

$^1$H-NMR (CDCl$_3$) δ 2.43 (s, 3H), 2.85 (d, J=14 Hz, 1H), 3.01 (t, J=12 Hz, 1H), 3.38 (t, J=12 Hz, 1H), 5.04 (dd, J=14 Hz, 1H), 5.88 (d, J=4 Hz, 2H), 6.73 (d, J=7 Hz, 1H), 6.89 (d, J=7 Hz, 1H), 7.02 (s, 1H), 7.25–7.50 (m, 7H), 7.56 (d, J=7 Hz, 1H), 7.79 (s, 1H), 8.54 (s, 2H).

EXAMPLE 15

1-(3,4-Methylenedioxyphenyl)-2-(pyridin-4-yl)methyl-2,3,4,9-tetrahydro-1H-β-carboline A solution of 1-(3,4-methylenedioxyphenyl)-2,3,4,9-tetrahydro-1H-β-carboline (2.92 g, 10 mmol) (prepared according to the process as disclosed in WO97/43287, Intermediate 7, page 24), 4-picolylchloride hydrochloride (1.64 g, 10 mmol) and DBU (3.1 g, 20 mmol) in DMF (50 mL) was stirred at room temperature for 16 h. Water (100 mL) and ethyl acetate (100 mL) were added to the reaction mixture. The solute, present in the organic phase, was purified by column chromatography (silica gel, ethyl acetate) to yield the product as an off-white solid.

MS (m/z) 382 (M−1).

$^1$H NMR (CDCl$_3$) δ 2.65 (m, 1H), 2.75 (d, 1H), 2.88 (m, 1H), 3.15 (m, 1H), 3.35 (d, J=15 Hz, 1H), 3.92 (d, J=15 Hz, 1H), 4.57 (s, 1H), 5.94 (s, 1H), 6.79 (d, J=8 Hz, 1H), 6.89 (m, 2H), 7.20–7.40 (m, 7H), 7.51 (d, J=6 Hz, 1H), 8.53 (d, J=7 Hz, 1H);

EXAMPLE 16

1-(3,4-Methylenedioxyphenyl)-2-(pyrimidin-2-yl)-2,3,4,9-tetrahydro-1H-β-carboline 1-(3,4-methylenedioxyphenyl)-2,3,4,9-tetrahydro-1H-β-carboline (2.3 g, 8.0 mmol) (prepared according to the process as disclosed in WO97/43287, Intermediate 7, page 24) and 2-chloropyrimidine (0.914 g, 8.0 mmol) were stirred in anhydrous DMF (15 mL) at 140° C. for 24 h. The reaction mixture was diluted with ethyl acetate (100 mL) and washed with saturated aqueous NH$_4$Cl solution (100 mL). The aqueous layer was extracted with ethyl acetate (2×50 mL). The combined organic layers were washed with brine (2×80 mL) and dried with MgSO$_4$. The solvents were evaporated and the product was isolated by column chromatography (silica gel, EtOAc:Hexane=1:9) as a yellowish solid.

mp: 176–177° C.

MS (m/z): 371 (MH$^+$), 369 (M−1); Anal. calculated for C$_{22}$H$_{18}$N$_4$O$_2$, C, 71.34; H, 4.90; N, 15.13; found C, 70.57; H, 4.92; N, 15.38.

$^1$H NMR (CDCl$_3$) δ 2.71 (m, 1H), 2.92 (m, 1H), 3.29 (m, 1H), 4.92 (dd, 1H, J=14, 7 Hz), 5.91 (d, 2H, J=6 Hz), 6.43 (t, 1H, J=6 Hz), 6.63 (d, 1H, J=10 Hz), 6.81 (d, 1H, J=10 Hz), 6.95 (s, 1H), 7.08 (m, 3H), 7.21 (d, 1H, J=8 Hz), 7.54 (d, 1H, J=10 Hz), 8.12 (s, 1H), 8.30 (d, 2H, J=6 Hz).

EXAMPLE 17

1-(3,4-Methylenedioxyphenyl-2-[5-(4-chlorophenyl)-pyrimidin-2-yl]-2,3,4,9-tetrahydro-1H-β-carboline Following the same procedure as outlined in Example 12 above, 1-(3,4-methylenedioxyphenyl)-2,3,4,9-tetrahydro-1H-β-carboline (295 mg, 1 mmol) (prepared according to the process as disclosed in WO97/43287, Intermediate 7, page 24) and 2-chloro-5-(4-chlorophenyl)pyrimidine (113 mg, 0.5 mmol) in DMF (5 mL, anhydrous) were reacted to yield the product as a white solid.

MS (m/z): 479 (MH$^+$).

$^1$H-NMR (CDCl$_3$) δ 2.87 (dd, J=4, 14 Hz, 1H), 3.01 (dt, J=5, 12 Hz, 1H), 3.38 (dt, J=4, 14 Hz, 1H), 5.04 (dd, J=5, 14 Hz, 1H), 5.91 (d, J=4 Hz, 2H), 6.73 (d, J=7 Hz, 1H), 6.89 (d, J=7 Hz, 1H), 7.00 (s, 1H), 7.20 (s, 1H), 7.25 (m, 2H), 7.30 (d, J=7 Hz, 1H), 7.40 (m, 4H), 7.56 (d, J=7 Hz, 1H), 7.83 (s, 1H), 8.54 (s, 2H).

EXAMPLE 18

[5-(3,4-Dimethoxyphenyl)-pyrimidin-2-yl]-1-(3,4-dimethoxyphenyl-2,3,4,9-tetrahydro-1H-β-carboline Following the same procedure as outlined in Example 16, 1-(3,4-methylenedioxyphenyl)-2,3,4,9-tetrahydro-1H-β-carboline (prepared according to the process as disclosed in WO97/43287, Intermediate 7, page 24) and 2-chloro-5-(3,5-dimethoxyphenyl)pyrimidine were reacted to yield the product as a white solid.

mp. 184–186° C.

MS (m/z) 523 (MH$^+$), 521 (M−1).

$^1$H NMR (CDCl$_3$) δ 2.81~3.20 (m, 2H), 3.40 (m, 1H), 3.71 (s, 3H), 3.79 (s, 3H), 3.88 (s, 3H), 3.91 (s, 3H), 5.01 (dd, 1H, J=14 Hz, 5 Hz), 6.68 (d, 1H, J=8 Hz), 6.70~7.19 (m, 7H), 7.28 (t, 1H, J=8 Hz), 7.52 (t, 1H, J=8 Hz), 8.20 (s, 1H), 8.52 (s, 2H).

EXAMPLE 19

1,2,3,4-Tetrahydro-3-(3,4-dimethoxyphenyl)-9H-pyrrolo-[3,4-b]quinolin-9-one (#12)

1-(3,4-Dimethoxyphenyl)-2,3,4,9-tetrahydro-1H-β-carboline (1.854 g, 6.04 mmol) (prepared as in Example 11) and KOt-Bu (1.14 g, 10.15 mmol) were stirred in DMF (60 mL) at room temperature for 10 min. Oxygen was bubbled through the solution for 1 h. The reaction mixture was neutralized with 1N HCl solution (10.15 mL, 10.15 mmol) and the water removed in vacuo as an azeotrope with toluene. Silica gel (~5 g) was added to the residual DMF solution, followed by diethyl ether (600 mL), which resulted in precipitation of the product onto the silica gel. The diethyl ether was decanted and the silica gel was washed with diethyl ether (2×100 mL). After the solvent was decanted and any remaining trace amounts evaporated, the residue was purified by column chromatograph (silica gel; EtOH:EtOAc=1:9) to yield the product as a bright yellow solid. The product was recrystallized from methanol.

mp. 223–225° C.

MS (m/z): 323 (MH$^+$), 321 (M−1).

$^1$H NMR (CD$_3$OD) δ 3.71 (s, 3H), 3.88 (s, 3H), 4.18 (d, 1H, J=14 Hz), 4.38 (d, 1H, J=14 Hz), 5.41 (s, 1H), 6.83 (m, 3H), 7.39 (t, 1H, J=7 Hz), 7.58 (m, 2H), 8.22 (d, 1H, J=6 Hz), 11.85 (s, 1H).

EXAMPLE 20

1,2,3,4-Tetrahydro-2-[5-(4-methoxyphenyl)-pyrimidin-2-yl]-3-(3,4-methylene-dioxyphenyl)-9H-pyrrolo-[3,4-b]quinolin-9-one (#2)

Sodium hydride (60% in mineral oil, 36 mg, 0.9 mmol) and 1-(3,4-methylenedioxyphenyl)-2-[5-(4-methoxyphenyl)-pyrimidin-2-yl]-2,3,4,9-tetrahydro-1H-β-carboline (186 mg, 0.39 mmol) (prepared as in Example 12) in DMF (10 mL, anhydrous) were stirred at room temperature for 30 min. Dry air was then bubbled through the solution for 16 h. Ethyl acetate (100 mL) and saturated NaHCO$_3$ were added, the organic phase was washed with water, brine, and dried with MgSO$_4$. Solvent was evaporated and the residue triturated with ethyl acetate to yield the product as a white solid.

mp: 325–327° C.

MS (m/z) 491 (MH$^+$); 489 (M−1).

$^1$H NMR (DMSO-d$_6$) δ 3.77 (s, 3H), 4.86 (d, J=12 Hz, 1H), 4.96 (dd, J=15 Hz, 1H), 5.98 (s, 2H), 6.29 (d, J=2.5 Hz, 1H), 6.87 (d, J=8 Hz, 1H), 6.95 (d, J=9 Hz, 2H), 6.98 (s, 1H), 7.02 (d, J=4 Hz, 3H), 7.34 (t, J=7 Hz, 1H), 7.57 (d, J=9 Hz, 2H), 7.63 (dd, J=8 Hz, 3H), 8.16 (d, J=8 Hz, 1H), 8.69 (broad, s, 2H); 11.85 (s, 1H).

EXAMPLE 21

1,2,3,4-Tetrahydro-2-[5-(3,4-dimethoxyphenyl)-pyrimidin-2-yl]-3-(3,4-methylenedioxyphenyl)-9H-pyrrolo-[3,4-b]quinolin-9-one (#1)

Sodium hydride (60% in mineral oil, 40 mg, 1.0 mmol) and 1-(3,4-methylenedioxyphenyl)-2-[5-(3,4-dimethoxyphenyl)-pyrimidin-2-yl]-2,3,4,9-tetrahydro-1H-β-carboline (218 mg, 0.43 mmol) (prepared as in Example 13) in DMF (10 mL, anhydrous) were stirred at room temperature for 30 min. Dry air was then bubbled through the solution for 16 h. Ethyl acetate (100 mL) and saturated NaHCO$_3$ were added, the organic phase was washed with water, brine, and dried with MgSO$_4$. Solvent was evaporated and the residue purified by chromatography (silica gel, ethyl acetate) to yield the product as a white solid.

MS (m/z) 521 (MH$^+$); 519 (M−1).

$^1$H NMR (DMSO-d$_6$) δ 3.77 (s, 3H), 3.83 (s, 3H), 4.86 (d, J=12 Hz, 1H), 4.96 (dd, J=15 Hz, 1H), 5.99 (s, 2H), 6.31 (d, J=2.5 Hz, 1H), 6.87 (d, J=8 Hz, 1H), 6.95 (d, J=9 Hz, 2H), 6.98 (s, 1H), 7.02 (m, 1H), 7.17 (d, J=7 Hz, 1H), 7.22 (s, 1H), 7.35 (t, J=7 Hz, 1H), 7.62 (m, 2H), 8.17 (d, J=8 Hz, 1H), 8.74 (broad, s, 2H); 11.85 (s, 1H).

EXAMPLE 21A

(S)-1,2,3,4-Tetrahydro-2-[5-(3,4-dimethoxyphenyl)-pyrimidin-2-yl]-3-(3,4-methylenedioxyphenyl)-9H-pyrrolo-[3,4-b]quinolin-9-one (#35)

Following the procedure as described in Example 21, (S)-1-(3,4-methylenedioxyphenyl)-2-[5-(3,4-dimethoxyphenyl)-pyrimidin-2-yl]-2,3,4,9-tetrahydro-1H-β-carboline was reacted to yield the title compound.

EXAMPLE 21B

(R)-1,2,3,4-Tetrahydro-2-[5-(3,4-dimethoxyphenyl)-pyrimidin-2-yl]-3-(3,4-methylenedioxyphenyl)-9H-pyrrolo-[3,4-b]quinolin-9-one (#36)

Following the procedure as described in Example 21, (R)-1-(3,4-methylenedioxyphenyl)-2-[5-(3,4-dimethoxyphenyl)-pyrimidin-2-yl]-2,3,4,9-tetrahydro-1H-β-carboline was reacted to yield the title compound.

EXAMPLE 22

1,2,3,4-Tetrahydro-2-[5-(4-methylphenyl)-pyrimidin-2-yl]-3-(3,4-methylenedioxyphenyl)-9H-pyrrolo-[3,4-b]quinolin-9-one (#7)

Following the same procedure as outlined in Example 21, sodium hydride (60% in mineral oil, 43 mg, 1.09 mmol) and 1-(3,4-methylenedioxyphenyl)-2-[5-(4-methylphenyl)-pyrimidin-2-yl]-2,3,4,9-tetrahydro-1H-β-carboline (278 mg, 0.60 mmol) (prepared as in Example 12) in DMF (15 mL, anhydrous) were reacted to yield the product as a white solid.

MS (m/z) 475 (MH$^+$).

$^1$H NMR (DMSO-d$_6$) δ 2.32 (s, 3H), 4.86 (d, J=12 Hz, 1H), 4.96 (dd, J=15 Hz, 1H), 5.98(s, 2H), 6.30 (d, J=2.5 Hz, 1H), 6.87 (d, J=8 Hz, 1H), 6.95 (d, J=9 Hz, 2H), 7.02 (d, J=4 Hz, 3H), 7.24 (d, J=7 Hz, 2H), 7.34 (t, J=7 Hz, 1H), 7.40–7.65 (m, 3H), 8.16 (d, J=8 Hz, 1H), 8.69 (broad, s, 2H); 11.85 (s, 1H).

EXAMPLE 23

1,2,3,4-Tetrahydro-[5-(3,4-dimethoxyphenyl)-pyrimidin-2-yl]-3-(3,4-dimethoxyphenyl)-9H-pyrrolo[3,4-b]quinolin-9-one (#15)

Following the same procedure as outlined in Example 19, [5-(3,4-Dimethoxyphenyl)-pyrimidin-2-yl]-1-(3,4-dimethoxyphenyl)-2,3,4,9-tetrahydro-1H-β-carboline (prepared as in Example 18) was reacted to yield the product as a white solid.

MS (m/z) 535 (MH$^+$), 537 (MH$^-$).

$^1$H NMR (CD$_3$OD) δ 3.74 (s, 3H), 3.79 (s, 3H), 3.80 (s, 3H), 3.85 (s, 3H), 5.0 (m, 2H), 6.31 (s, 1H), 6.75~7.15 (m, 5H), 7.36 (t, 1H, J=8 Hz), 7.32 (d, 1H, J=8 Hz), 7.61 (m, 2H), 8.29 (d, 1H, J=8 Hz), 8.58 (s, 2H).

EXAMPLE 24

1,2,3,4-Tetrahydro-3-(3,4-methylenedioxyphenyl)-2-(pyridin-4-yl)methyl-9H-pyrrolo-[3,4-b]quinolin-9-one (#5)

Following the same procedure as outlined in Example 21, sodium hydride (60% in mineral oil, 40 mg, 1.0 mmol) and 1-(3,4-methylenedioxyphenyl)-2-(pyridin-4-yl)methyl-2,3,4,9-tetrahydro-1H-β-carboline (192 mg, 0.50 mmol) (prepared as in Example 15) in DMF (10 mL, anhydrous) were reacted to yield the product as a white solid.

MS (m/z) 398 (MH$^+$).

$^1$H NMR (DMSO-d$_6$) δ 3.58 (d, J=14 Hz, 1H), 3.76 (d, J=15 Hz, 1H), 3.88 (d, J=15 Hz, 1H), 4.01 (d, J=14 Hz, 1H), 5.17 (s, 1H), 6.03 (s, 1H), 6.97 (s, 3H), 7.7.35 (m, 3H), 7.60 (m, 2H), 7.34 (t, J=7 Hz, 1H), 8.11 (d, J=8 Hz, 1H), 8.53 (d, J=6 Hz2H); 11.45 (s, 1H).

EXAMPLE 25

1,2,3,4-Tetrahydro-2-(tert-butoxycarbonyl)-3-(3,4-methylenedioxyphenyl)-9H-pyrrolo-[3,4-b]quinolin-9-one (#3)

2-t-Butoxycarbonyl-1-(3,4-methylenedioxyphenyl)-2,3,4,9-tetrahydro-1H-β-carboline (4.09 g, 10.4 mmol) (prepared as in Example 9) was dissolved in dry DMF (100 mL). Potassium t-butoxide (2.55 g, 22.7 mmol) was introduced in one portion and the suspension was stirred until a clear solution was obtained. Oxygen gas was then passed through the solution via a syringe needle for 16 h. The reaction was quenched by the addition of glacial acetic acid (25 mmol) and poured into a mixture of diethyl ether and water, which resulted in a precipitate that was collected by filtration. The product was purified by flash chromatography (0–10% MeOH/CHCl$_3$) to yield the product as a white solid.

MS (m/z): 405 (M–1).

$^1$H-NMR (CDCl$_3$) δ 1.38–1.65 (series of s, 9H), 4.79–4.88 (m, 2H), 5.86–6.27 (series of m, 3H), 6.71–7.50 (series of m, 7H), 11.57 and 11.64 (s, 1H).

EXAMPLE 26

1,2,3,4-Tetrahydro-2-(benzyloxycarbonyl)-3-(3,4-methylenedioxyphenyl)-9H-pyrrolo-[3,4-b]quinolin-9-one (#27)

2-benzyloxycarbonyl-1-(3,4-methylenedioxyphenyl)-2,3,4,9-tetrahydro-1H-β-carboline (3.63 g, 8.51 mmol)) (prepared as in Example 10) was dissolved in dry DMF (25 mL). Potassium t-butoxide (2.40 g, 21.4 mmol) was introduced in one portion and the suspension was stirred until a clear solution was obtained. Oxygen gas was then passed through the solution via a syringe needle for 16 h. The reaction was quenched by the addition of glacial acetic acid (1.23 mL, 21.0 mmol) and poured into water (250 mL), which resulted in a precipitate that was collected by filtration. The product was purified by flash chromatography (2–10% MeOH/CHCl$_3$) to yield the product as a red powder.

MS (m/z): 439 (M–1).

$^1$H-NMR (CDCl$_3$) δ 4.63–5.18 (series of m, 4H), 5.71–5.85 (series of m, 3H), 6.54–6.72 (series of m, 3H), 6.98–7.01 (m, 1H), 7.25–7.57 (series of m, 7H), 8.27–8.32 (m, 1H), 10.04 and 10.33 (s, 1H).

EXAMPLE 27

(E)-4-[3-Oxo-3-[1,2,3,4-tetrahydro-3-(2,3-dihydrobenzofuran-5-yl)-9H-pyrrolo-[3,4-b]quinolin-9-one-2-yl]-1-propenyl]benzoic acid, methyl ester (#20)

A. A solution of (E)-4-carbomethoxycinnamic acid (5.09 g, 24.7 mmol) was dissolved in dry THF (25 mL) and treated under an argon atmosphere with oxalyl chloride (3.00 mL, 34.4 mmol) and a drop of dry DMF. After heating at 50° C. for 2 hours, the reaction mixture was concentrated in vacuo to yield the acid chloride of (E)-carboxymethyl cinnamic acid as a tan solid.

B. The product from Part A (78 mg, 0.35 mmol) was added to a solution of 1,2,3,4-tetrahydro-3-(2,3-dihydrobenzofuran-5-yl)-9H-pyrrolo-[3,4-b]quinolin-9-one (93.5 mg, 0.31 mmol) (prepared as in Example 6), THF (3 mL), triethylamine (0.20 mL, 1.43 mmol), and DMAP (5 mg). The mixture was stirred for 16 h at room temperature, diluted with 1N HCl (10 mL) and the resulting white precipitate collected by filtration. The solid was washed with water (3×), with diethyl ether (3×) and dried in vacuo to yield the product as a slightly pink solid.

MS (m/z): 493 (MH$^+$).

$^1$H-NMR (DMSO) δ 3.10–3.m, 2H), 3.87 (s, 3H), 4.43–4.52 (m, 2H), 4.70–5.14 (series of m, 2H), 6.23 and 6.61 (s, 1H), 6.72–6.79 (m, 1H), 7.07–8.19 (series of m, 12H), 10.69 and 10.77 (s, 1H).

EXAMPLE 28

1,2,3,4-Tetrahydro-3-(3,4-methylenedioxyphenyl)-2-[5-(3-trifluoromethylphenyl)furoyl]-9H-pyrrolo-[3,4-b]quinolin-9-one (#13)

To a solution of 5-(3-trifluoromethylphenyl)-2-furoic acid (80.44 mg, 0.314 mmol) in 1:1 DCM:THF (5 mL, anhydrous) was added oxalyl chloride (43.85 mg, 0.345 mmol), followed by two drops of DMF. The mixture was stirred at room temperature for 1 h. A suspension of 1,2,3,4-tetrahydro-3-(3,4-methylenedioxyphenyl)-9H-pyrrolo-[3,4-b]quinolin-9-one (96.2 mg, 0.314 mmol) (prepared as in Example 5), triethylamine (0.13 mL), and DMAP (trace) in 1:1 DCM:THF (5 mL) was added. The resulting mixture was stirred at room temperature for 16 h. Ethyl acetate (50 mL) was added, and the solution was washed with aq. NaHCO$_3$, brine, 1N HCl, brine and then dried with MgSO$_4$. The solvent was evaporated and the residue triturated with ethyl acetate to yield the product as a white solid.

mp: 219–221° C.

MS (m/z): 545 (MH$^+$), 567 (M+23), 543 (MH$^-$).

$^1$H-NMR (DMSO-d$_6$) δ 5.09 (d, J=14 Hz, 1H), 5.46 (d, J=14 Hz, 1H), 5.99 (s, 2H), 6.39 (s, 1H), 6.91 (d, J=8 Hz, 1H), 6.97 (d, J=9 Hz, 1H), 7.02 (s, 1H), 7.33 (d, J=8 Hz, 1H), 7.38 (d, J=4 Hz, 1H), 7.43 (d, J=4 Hz, 1H), 7.60 (m, J=8 Hz, 2H), 7.77 (d, J=5 Hz, 2H), 8.16 (d, J=4 Hz, 3H), 11.55 (s, 1H).

EXAMPLE 29

1,2,3,4-Tetrahydro-3-(3,4-methylenedioxyphenyl)-2-(6-hydroxy-2-benzo-furoyl)-9H-pyrrolo[3,4-b]quinolin-9-one (#9)

To a solution of 6-hydroxy-2-benzofuranoic acid (0.054 g, 0.3 mmol) in tetrahydrofuran (5 mL) at 0° C. was added dropwise oxalyl chloride (0.046 g, 0.36 mmol) followed by DMF (2 drops). The solution was warmed to 25° C. and stirred for 30 min, then concentrated in vacuo. The residue was dissolved in tetrahydrofuran (5 mL), and added to a solution of 1,2,3,4-tetrahydro-3-(3,4-methylenedioxyphenyl)-9H-pyrrolo-[3,4-b]quinolin-9-one (0.092 g, 0.3 mmol) (prepared as in Example 5) in THF (5 ml), triethylamine (0.045 g, 0.45 mmol) and 4-dimethylaminopyridine (0.01 g, cat.). The solution was stirred for 20 h at 25° C., and then concentrated in vacuo.

The resulting crude residue was purified by silica gel column chromatography, eluting with 3% methanol in dichloromethane, to yield the product as a clear oil.

$^1$H NMR (CD$_3$OD): δ 5.25 (d, J=15 Hz, 1H), 5.48 (d, J=15 Hz, 1H), 5.91 (s, 2H), 6.45 (broad s, 1H), 6.84 (m, 3H), 6.93 (m, 2H), 7.00 (s, 1H), 7.25–7.89 (overlapping m's, 5H), 8.32 (d, 1H).

EXAMPLE 30

(E)-4-[3-Oxo-3-[1,2,3,4-tetrahydro-3-(3,4-methylenedioxyphenyl)-9H-pyrrolo-[3,4-b]quinolin-9-one-2-yl]-1-propenyl]benzoic Acid Methyl Ester (#6)

Following the procedure outlined in Example 20, 1,2,3,4-tetrahydro-3-(3,4-methylenedioxyphenyl)-9H-pyrrolo-[3,4-b]quinolin-9-one (398 mg, 1.30 mmol) (prepared as in Example 5) was reacted with the acid chloride of (E)-carboxymethyl cinnamic acid (301 mg, 1.34 mmol), in the presence of triethylamine (0.54 mL, 3.87 mmol) in a 1:1 mixture of dichloromethane:THF (40 mL) to yield the product as a tan solid.

MS (m/z): 493 (M−1).

$^1$H-NMR (CD$_3$OD) δ 3.86 (s, 3H), 4.69–5.29 (series of m, 2H), 5.93–6.02 (m, 2H), 6.27 and 6.62 (s, 1H), 6.89–8.21 (series of m, 13H), 9.50 and 11.96 (broad s, 1H).

EXAMPLE 31

1,2,3,4-Tetrahydro-2-(imidazol-1-yl)thiocarbonyl-3-(3,4-methylenedioxyphenyl)-9H-pyrrolo-[3,4-b]quinolin-9-one (#18)

To a suspension of 1,1'-thiocarbonyldiimidazole (0.192 g, 1.08 mmol) in DMF (5 mL, anhydrous) at 0° C. was added 1,2,3,4-tetrahydro-3-(3,4-methylenedioxyphenyl)-9H-pyrrolo-[3,4-b]quinolin-9-one (0.30 g, 0.98 mmol) (prepared as in Example 5). The mixture warmed to room temperature and stirred for 20 h. The solution was diluted with water and extracted into ethyl acetate. The organic layers were combined and washed with aq. NaHCO$_3$ and brine, dried with MgSO$_4$ and concentrated in vacuo, to yield the product as a light tan solid.

mp: 211–215° C. (dec.).

MS (m/z): 415 (M−1).

$^1$H-NMR (CD$_3$OD) δ 4.71–5.16 (m, 1H), 5.46 (d, J=15 Hz, 1H), 6.36–7.17 (overlapping m's, 5H), 7.42 (m, 2H), 7.52 (m, 1H), 7.58 (m, 2H), 8.28 (m, 1H).

EXAMPLE 32

(E)-4-[3-Oxo-3-[1,2,3,4-tetrahydro-3-(3,4-methylenedioxyphenyl)-9H-pyrrolo-[3,4-b]quinolin-9-one-2-yl]-1-propenyl]benzoic acid (#8)

(E)-4-[3-Oxo-3-[1,2,3,4-tetrahydro-3-(3,4-methylenedioxyphenyl)-9H-pyrrolo-[3,4-b]quinolin-9-one-2-yl]-1-propenyl]benzoic acid methyl ester (149 mg, 0.30 mmol), (prepared as in Example 30) was suspended in a 1:1 mixture of 1 N aqueous sodium hydroxide:methanol (10 mL) and heated to reflux for 8 h. The reaction mixture was treated with aqueous HCl to pH 1, resulting in a white precipitate. The precipitate was collected by filtration and washed with water (30 mL) and diethyl ether (160 mL) to yield the product as a white solid.

MS (m/z): 481 (MH$^+$).

$^1$H-NMR (DMSO) δ 4.71–5.13 (series of d, 2H,), 5.95–5.98 (m, 2H), 6.23 and 6.61 (s, 1H), 6.84–7.78 (series of m, 10H), 7.89–7.92 (m, 3H), 8.13–8.17 (m, 1H), 11.94 (broad s, 1H).

EXAMPLE 33

1,2,3,4-Tetrahydro-3-(3,4-methylenedioxyphenyl)-2-[5-(4-nitrophenyl)-furoyl]-9H-pyrrolo[3,4-b]quinolin-9-one (#16)

1,2,3,4-Tetrahydro-3-(3,4-methylenedioxyphenyl)-9H-pyrrolo-[3,4-b]quinolin-9-one (70.3 mg, 0.229 mmol) (prepared as in Example 5), 5-(4-nitrophenyl)-2-furoic acid (58.9 mg, 0.25 mmol) and PyBrOP (0.118 g, 0.25 mmol) were stirred in DMF (3 mL) and DIPEA (0.088 mL, 0.50 mmol) for 16 h. The reaction mixture was poured into ethyl acetate (80 mL) and the resulting organic layer washed with 1N aqueous HCl (3×50 mL), saturated aqueous Na$_2$CO$_3$ solution (1×50 mL) and brine (1×50 mL). The organic layer was dried with MgSO$_4$ and the solvent evaporated in vacuo. Column chromatography of the residue (silica gel, 5% CH$_3$OH/CH$_3$Cl) yielded the product as a yellow powder.

MS (m/z): 522 (MH$^+$), 520 (M−1).

$^1$H NMR (DMSO-d$_6$) δ 5.05 (d, 1H, J=14 Hz), 5.45 (d, 1H, J=14 Hz), 6.0 (s, 2H), 6.42 (s, 1H), 6.95 (m, 3H), 7.32~7.41 (m, 2H), 7.55~7.65 (m, 3H), 8.12 (m, 3H), 8.39 (m, 2H), 11.91 (s, 1H).

EXAMPLE 34

1,2,3,4-tetrahydro-3(3,4-methylenedioxyphenyl)2-[5-(4-aminophenyl)-furoyl]-9H-pyrrolo[3,4-b]quinolin-9-one (#26)

1,2,3,4-Tetrahydro-3-(3,4-methylenedioxyphenyl)-2-[(5-(4-nitrophenyl))-furoyl]-9H-pyrrolo[3,4-b]quinolin-9-one (25 mg, 0.0479 mmol) (prepared as in Example 33) was stirred with 10% Pd on Carbon (5.1 mg, 0.00479 mmol) under 1 atm H$_2$ at room temperature for 14 h. The solvent was evaporated and product isolated by preparative TLC as a yellow powder.

MS (m/z): 492 (MH$^+$); 490 (M−1).

$^1$H NMR (CD$_3$OD) δ 5.25 (d, 1H, J=14 Hz), 5.45 (d, 1H, J=14 Hz), 5.91 (s, 2H), 6.45 (s, 1H), 6.70~8.60 (m, 13H).

EXAMPLE 35

1,2,3,4-Tetrahydro-3-(3,4-methylenedioxyphenyl)-2-[2-hydroxynicotinoyl]-9H-pyrrolo[3,4-b]-quinolin-9-one (#25)

Following the procedure outlined in Example 33, with appropriate substitution of reagents, the product was obtained as a pale yellow solid.

MS (m/z): 428 (MH$^+$); 426 (M−1).

$^1$H NMR (CD$_3$OD) δ 4.65 (d, J=14 Hz), 5.10 (d, 1H, J=14 Hz), 5.85 (s, 2H), 5.92 (s, 1H), 6.50~7.10 (m, 3H), 7.30~7.70 (m, 5H), 8.25 (m, 2H).

EXAMPLE 36

1,2,3,4-Tetrahydro-3-(3,4-methylenedioxyphenyl)-2-[5-(4-methoxyphenyl)-furoyl]-9H-pyrrolo[3,4-b]-quinolin-9-one (#21)

Following the procedure outlined in Example 33, with appropriate substitution of reagents, the product was obtained as a pale yellow solid.

MS (m/z): 507 (MH$^+$); 505 (M−1).

$^1$H NMR (CDCl$_3$) δ 3.85 (s, 3H), 5.10 (d, 1H, J=14 Hz), 5.38 (d, 1H, J=14 Hz), 6.02 (s, 2H), 6.41 (s, 1H), 6.80~8.35 (m, 13H), 11.80 (s, 1H).

EXAMPLE 37

1,2,3,4-Tetrahydro-3-(3,4-methylenedioxyphenyl)-2-[5-(4-hydroxyphenyl)furoyl]-9H-pyrrolo[3,4-b]-quinolin-9-one (#22)

Following the procedure outlined in Example 33, with appropriate substitution of reagents, the product was obtained as a pale yellow solid.

MS (m/z): 493 (MH$^+$); 491 (M−1).

$^1$H NMR (DMSO-d$_6$) δ 5.05 (d, 1H, J=14 Hz), 5.15 (d, 1H, J=14 Hz), 5.75 (s, 2H), 6.31 (s, 1H), 6.80~8.35 (m, 13H), 11.60 (s, 1H).

EXAMPLE 38

1,2,3,4-Tetrahydro-3-(3,4-methylenedioxyphenyl)-2-[5-(4-methoxycarbonylphenyl)-furoyl]-9H-pyrrolo[3,4-b]-quinolin-9-one (#24)

Following the procedure outlined in Example 33, with appropriate substitution of reagents, the product was obtained as a pale yellow solid.

$^1$H NMR (DMSO-d$_6$) δ 4.10 (s, 3H), 5.10 (d, 1H, J=14 Hz), 5.50 (d, 1H, J=14 Hz), 6.02 (s, 2H), 6.45 (s, 1H), 6.80~8.35 (m, 13H).

EXAMPLE 39

1,2,3,4-Tetrahydro-3-(3,4-methylenedioxyphenyl)-2-[5-(4-formylphenyl)-furoyl]-9H-pyrrolo[3,4-b]-quinolin-9-one (#23)

Following the procedure outlined in Example 33, with appropriate substitution of reagents, the product was obtained as a pale yellow solid.

MS (m/z): 503 (M−1).

$^1$H NMR (DMSO-d$_6$) δ 5.10 (d, 1H, J=14 Hz), 5.55 (d, 1H, J=14 Hz), 6.02 (s, 2H), 6.45 (s, 1H), 6.80~8.35 (m, 13H).

EXAMPLE 40

(E)-4-[3-Oxo-3-[1,2,3,4-tetrahydro-3-(3,4-methylenedioxyphenyl)-4-methyl-9H-pyrrolo-[3,4-b]quinolin-9-one-2-yl]-1-propenyl]benzoic acid, methyl ester (#63)

(E)-4-[3-Oxo-3-[1,2,3,4-tetrahydro-3-(3,4-methylenedioxyphenyl)-9-methoxy-9H-pyrrolo-[3,4-b]quinolin-2-yl]-1-propenyl]benzoic acid, methyl ester (#64)

A solution of (E)-4-[3-Oxo-3-[1,2,3,4-tetrahydro-3-(3,4-methylenedioxyphenyl)-9H-pyrrolo-[3,4-b]quinolin-9-one-2-yl]-1-propenyl]benzoic acid methyl ester (349 mg, 0.62 mmol) (prepared as in Example 30) and iodomethane (0.060 mL, 0.96 mmol) in dry acetone (10 mL) was treated with anhydrous potassium carbonate (241 mg, 1.74 mmol) and heated to reflux for 3 h under an argon atmosphere. The reaction mixture was concentrated in vacuo and the residue purified by flash chromatography (0–10% methanol in dichloromethane) to yield a mixture of the N- and O-methylated products.

The mixture of N- and O-methylated products was separated by column chromatography (0–10% MeOH/DCM) to yield the N-methylated product (E)-4-[3-Oxo-3-[1,2,3,4-tetrahydro-3-(3,4-methylenedioxyphenyl)-4-methyl-9H-pyrrolo-[3,4-b]quinolin-9-one-2-yl]-1-propenyl]benzoic acid, methyl ester as a tan solid.

MS (m/z): 509 (M−1).

$^1$H-NMR (CDCl$_3$) δ 3.55 (s, 3H), 3.93 (s, 3H), 5.10 (m, 2H), 5.94 (nd, J=3.7 Hz, 2H), 6.53 (s, 1H), 6.78 (d, J=7.9 Hz, 1H), 6.86–6.96 (m, 3H), 7.44–7.76 (series of m, 6H), 8.05 (d, J=8.2 Hz, 2H), 8.55 (d, J=7.4 Hz).

and the O-methylated product (E)-4-[3-Oxo-3-[1,2,3,4-tetrahydro-3-(3,4-methylenedioxyphenyl)-9-methoxy-9H-pyrrolo-[3,4-b]quinolin-2-yl]-1-propenyl]benzoic acid, methyl ester as a pink solid.

MS (m/z): 509 (M−1).

$^1$H-NMR (CDCl$_3$) δ 3.93 (s, 3H), 4.38 (s, 3H), 5.45 (d, J=17.1 Hz, 1H), 5.64 (d, J=17.1 Hz, 1H), 5.91 (s, 2H), 6.26 (s, 1H), 6.75–7.09 (series of d, 4H), 7.39–8.23 (series of m, 9H).

EXAMPLE 41

1,2,3,4-Tetrahydro-2-(pyrimidin-2-yl)-3-(3,4-methylenedioxyphenyl)-9H-pyrrolo-[3,4-b]quinolin-9-one (#11)

To a solution of 1-(3,4-methylenedioxyphenyl)-2-(pyrimidin-2-yl)-2,3,4,9-tetrahydro-1H-β-carboline (0.153 g, 0.415 mmol) (prepared as in Example 16) in anhydrous DMF (4.1 mL) was added KOtBu (0.079 g, 0.70 mmol, 1.7 eq.). After 5 min, oxygen gas was bubbled through the solution for 1 h. Diethyl ether (45 mL) was added to the reaction mixture and the supernatant decanted. Brine (2 mL) was added to the residue and the pH was adjusted to pH~7 by addition of a few drops of 1N HCl. The water was removed in vacuo as an azeotrope with toluene. The resulting deep red residue was dissolved in a minimum amount of THF, and purified by column chromatography (silca gel; EtOH: CH$_2$Cl$_2$=1:9) to yield the product as a white solid.

MS (m/z): 383 (M−1); 385 (MH$^+$).

$^1$H NMR (DMSO-d$_6$) δ 4.84 (dd, 2H, J=14 Hz, 10 Hz), 5.98 (s, 2H), 6.25 (s, 1H), 6.69 (t, 1H, J=5 Hz), 6.85 (d, 1H, J=8 Hz), 6.92 (d, 1H, J=8 Hz), 7.00 (s, 1H), 7.33 (t, 1H, J=7 Hz), 7.60 (m, 2H), 8.15 (d, 1H, J=8 Hz), 8.41 (broad s, 2H), 11.9 (s, 1H).

EXAMPLE 42

1,2,3,4-Tetrahydro-2-(pyrimidin-2-yl)-3-(3,4-methylenedioxyphenyl)-9H-pyrrolo-[3,4-b]quinolin-9-one (#11)

1,2,3,4-Tetrahydro-3-(3,4-methylenedioxyphenyl)-9H-pyrrolo-[3,4-b]quinolin-9-one (100 mg, 0.3265 mmol) (prepared as in Example 5) and 2-chloropyrimidine (38 mg, 0.3265 mmol) were stirred in DMF (2.5 mL) at 100° C. for 16 h. The solvent was removed under vacuum and the residue purified by column chromatography (silica gel, 5% CH$_3$OH/CH$_3$Cl) to yield a yellow oil. Trituration of the oil with MeOH afforded the product as a pale yellow solid.

MS (m/z): 383 (M−1); 385 (MH$^+$).

$^1$H NMR (DMSO-d$_6$) δ 4.84 (dd, 2H, J=14 Hz, 10 Hz), 5.98 (s, 2H), 6.25 (s, 1H), 6.69 (t, 1H, J=5 Hz), 6.85 (d, 1H, J=8 Hz), 6.92 (d, 1H, J=8 Hz), 7.00 (s, 1H), 7.33 (t, 1H, J=7 Hz), 7.60 (m, 2H), 8.15 (d, 1H, J=8 Hz), 8.41 (broad s, 2H), 11.9 (s, 1H).

EXAMPLE 43

1,2,3,4-Tetrahydro-2-[(4-pyridinyl)methyloxycarbonyl]-3-(3,4-methylenedioxyphenyl)-9H-pyrrolo-[3,4-b]quinolin-9-one, hydrochloride salt (#37)

A mixture of 1,2,3,4-tetrahydro-3-(3,4-methylenedioxyphenyl)-9H-pyrrolo-[3,4-b]quinolin-9-one, hydrochloride salt (101 mg, 0.33 mmol) (prepared as in Example 5), (4-pyridinyl)methyl-4-nitrophenylcarbonic acid ester (106 mg, 0.38 mmol) (prepared as in Example 7) and triethylamine (2 eq.) was heated to reflux for 1 h. The reaction mixture was concentrated in vacuo and purified by flash chromatography (0–10% MeOH/CHCl$_3$). The corresponding salt was formed by precipitation of the methanolic solution of the free base with a solution of HCl-ether.

MS (m/z) 442 (MH$^+$).

$^1$H NMR (CD$_3$OD) δ 5.02–5.62 (series of m, 4H), 5.93–6.00 (m, 2H), 6.23 and 6.44 (s, 1H), 6.82–7.04 (m, 3H), 7.71–7.90 (m, 4H), 8.12 (d, J=6.2 Hz, 1H), 8.44 (s, 1H), 8.78 (s, 1H), 8.84 (s, 1H).

EXAMPLE 44

1,2,3,4-Tetrahydro-2-[(4-pyridinyl) methyloxycarbonyl]-3-(2,3-dihydrobenzofuran-5-yl)-9H-pyrrolo-[3,4-b]quinolin-9-one (#53)

Following the procedure outlined in Example 36, 1,2,3,4-tetrahydro-3-(2,3-dihydrobenzofuran-5-yl)-9H-pyrrolo-[3,4-b]quinolin-9-one, hydrochloride salt (prepared as in Example 6) and (4-pyridinyl)methyl-4-nitrophenylcarbonic acid ester (prepared as in Example 7) were reacted to yield the product as a slightly pink solid.

MS (m/z) 440 (MH$^+$).

$^1$H NMR (DMSO-d$_6$) δ 2.82–2.94 (m, 2H), 4.35–5.26 (series of m, 6H), 5.91 (s, 1H) 6.45–7.58 (series of m, 9H), 8.30–8.46 (m, 2H), 12.26 (broad, 1H).

EXAMPLE 45

1,2,3,4-Tetrahydro-2-[[5-[2-(4-morpholinyl)ethoxy]-2-benzofuryl]carbonyl]-3-(3,4-methylenedioxyphenyl)-9H-pyrrolo-[3,4-b]quinolin-9-one, hydrochloride salt (#49)

1,2,3,4-Tetrahydro-3-(3,4-methylenedioxyphenyl)-9H-pyrrolo-[3,4-b]quinolin-9-one, hydrochloride salt (222 mg, 0.65 mmol) (prepared as in Example 5) and 6-[2-(1-Morpholino)ethoxy]-2-benzofurancarboxylic acid (209 mg, 0.72 mmol) (prepared as in Example 8) were suspended in dry THF (10 mL). To this mixture was added PyBrOP (358 mg, 0.77 mmol) and triethylamine (0.40 mL, 2.87 mmol). The mixture was stirred overnight under an argon atmosphere and concentrated in vacuo. Purification of the residue by flash chromatography (0–10% MeOH/CHCl$_3$) yielded the free base. The corresponding salt was formed by precipitation of the methanolic solution of the free base with a solution of HCl-ether.

MS (m/z) 580 (MH$^+$).

$^1$H NMR (DMSO-d$_6$) δ 3.17–3.24 (m, 2H), 3.52–3.61 (m, 4H), 3.80 (t, J=11.7 Hz, 2H), 3.98 (d, J=12.1 Hz, 2H), 4.53 (broad s, 1H), 5.10 (d, J=13.3 Hz, 1H), 5.40 (d, J=13.3 Hz, 1H), 6.00 (s, 2H), 6.42 (s, 1H), 6.90–7.08 (series of m, 4H), 7.32–7.66 (series of m, 4H), 7.73 (d, J=8.5 Hz, 1H), 8.16 (d, J=8.0 Hz, 1H), 10.81 (s, 1H), 12.06 (s, 1H).

EXAMPLE 46

1-(2,3-dihydrobenzofuranyl)-2-[5-(4-methoxyphenyl)-pyrimidin-2-yl]-2,3,4,9-tetrahydro-1H-β-carboline 1-(2,3-dihydrobenzo-5-furanyl)-2,3,4,9-tetrahydro-1H-β-carboline (prepared according to the process as disclosed in WO97/43287, Intermediate 10, page 25) (3.35 g, 11.54 mmol), 5-(4-methoxyphenyl)-2-chloropyrimidine (2.55 g, 11.54 mmol), and N,N-diisopropylethylamine (3.5 mL) were stirred in DMF (10 mL, anhydrous) at 120° C. for 16 h. The resulting mixture was quenched with 10% NaCl and extracted with ethyl acetate. The organic layer was washed with 10% NaCl, brine, and then dried with MgSO$_4$. The reaction mixture solvent was evaporated, the resulting residue triturated with CH$_2$Cl$_2$ and filtered. The filtrate was purified by column chromatography (silica gel, ethyl acetate:hexanes=4:6) to yield the product as a white solid.

mp: 242–243° C.

MS (m/z): 475 (MH$^+$), 483 (M−1).

$^1$H-NMR (DMSO-d$_6$) δ 2.50 (s, 1H), 2.83 (m, 2H), 3.12 (t, J=8.7 Hz, 2H), 3.24 (m, 1H), 3.78 (s, 3H), 4.49 (t, J=8.7 Hz, 2H), 4.90 (d, J=12 Hz, 1H), 6.72 (d, J=8.2 Hz, 1H), 7.03 (m, 4H), 7.06 (d, J=7 Hz, 1H), 7.17 (d, J=9.3 Hz, 2H), 7.30 (d, J=8 Hz, 1H), 7.46 (d, J=7.6 Hz, 1H), 7.59 (d, J=8.6 Hz, 2H), 8.73 (s, 2H), 11.00 (s, 1H).

EXAMPLE 47

1,2,3,4-Tetrahydro-2-[5-(4-methoxyphenyl)-pyrimidin-2-yl]-3-(2,3-dihydrobenzofuranyl)-9H-pyrrolo-[3,4-b]quinolin-9-one (#39)

Sodium hydride (60% in mineral oil, 87 mg, 2.18 mmol) and 1-(2,3-dihydro-5-benzfuranyl)-2,3,4,9-tetrahydro-2-[5-(4-methoxyphenyl)-2-pyrimidinyl]-1H-β-carboline (450 mg, 0.95 mmol) (prepared as in Example 46) in DMF (30 mL, anhydrous) were stirred at room temperature for 30 min. Dry air was then bubbled through the solution for 16 h. Ethyl acetate (200 mL) was then added to the solution. The resulting mixture was washed with 10% NaCl solution, brine and then dried with MgSO$_4$. The solvent was evaporated and the residue triturated with ethyl acetate to yield the product as a white solid.

mp: 301–302° C.

MS (m/z) 489 (MH$^+$); 487 (M−1).

$^1$H NMR (DMSO-d$_6$) δ 3.11 (t, J=8.7 Hz, 2H), 3.77 (s, 3H), 4.47 (t, J=8.7 Hz, 2H), 4.89 (m, 2H), 6.29 (s, 1H), 6.72 (d, J=8.1 Hz, 1H), 6.95 (d, J=8.7 Hz, 2H), 7.29 (m, 3H), 7.57 (d, J=8.6 Hz, 2H), 7.64 (d, J=8.2 Hz, 2H), 8.16 (d, J=8.0 Hz, 1H), 8.67 (s, 2H), 11.87 (s, 1H).

EXAMPLE 47A (R)-1,2,3,4-Tetrahydro-2-[5-(4-methoxyphenyl)-pyrimidin-2-yl]-3-(2,4-dihydrobenzofuranyl)-9H-pyrrolo-[3,4-b]quinolin-9-one (#66)

(R)-1,2,3,4-tetrahydro-3-(2,3-dihydrobenzofuran-5-yl)-9H-pyrrolo-[3,4-b]quinolin-9-one (0.23 g, 0.678 mmol) (prepared as in Example 6A), and 5-(4-methoxyphenyl)-2-chloropyrimidine (0.167 g, 0.758 mmol) were stirred with diisopropyl ethyl amine (0.33 mL) and KF (44.8 mg, 0.758 mmol) in DMF (5 mL) at 60° C. for 36 h. The reaction mixture was diluted with CH$_2$Cl$_2$ (75 mL) and EtOAc (75 mL). This was washed with 1N aqueous HCl (3×100 mL). This was then washed with brine (2×100 mL). After drying over MgSO$_4$, this was concentrated to yellow oil. The crude product was purified by silica gel column to yield the product as white solid.

MS (m/z): 499 (MH$^+$), 497 (M−1).

$^1$H NMR δ CDCl$_3$ 3.02 (t, 2H, J=11.7 Hz), 3.82 (s, 3H), 4.44 (t, 2H, J=11.7 Hz), 4.95 (d, 1H, J=15.6 Hz), 5.08 (d, 1H, J=15.6 Hz), 6.24 (s, 1H), 6.62 (d, 1H, J=7.8 Hz), 6.92 (d, 2H, J=7.8 Hz), 7.14~7.61 (m, 7H), 8.45 (m, 3H), 9.65 (s, 1H).

Rf=0.47 (10% CH$_3$OH/CHCl$_3$). Elemental analysis: for C$_{30}$H$_{24}$N$_4$O$_3$, calculated % C, 73.76; % H, 4.95; % N, 11.47; % O, 9.82; found % C, 73.73; % H, 4.87; % N, 11.40; O % 9.65.

EXAMPLE 48

(R)-1,2,3,4-Tetrahydro-3-(3,4-methylenedioxyphenyl)-2-[5-(3-trifluoromethylphenyl)furo-2-yl]-9H-pyrrolo-[3,4-b]quinolin-9-one (#50)

To a solution of 5-(3-trifluoromethylphenyl)-2-furoic acid (504.4 mg, 1.97 mmol) in 1:1 DCM:THF (10 mL, anhydrous) was added oxalyl chloride (275 mg, 2.17 mmol), followed by two drops of DMF. The reaction mixture was stirred at room temperature for 2 h. To the reaction mixture were added triethylamine (1.1 mL), DMAP (trace), and a suspension of enantiomerically pure 1,2,3,4-tetrahydro-3-(3,4-methylenedioxyphenyl)-9H-pyrrolo-[3,4-b]quinolin-9-one (603 mg, 1.97 mmol) (prepared as in Example 5A), in 1:1 DCM:THF (10 mL). The resulting mixture was stirred at room temperature for 16 h. Ethyl acetate (100 mL) was added, and the solution was washed with aq. NaHCO$_3$, brine, 1N HCl, brine and then dried with MgSO$_4$. The reaction mixture solvent was evaporated and the residue triturated with ethyl acetate to yield the product as a white solid.

mp: 219–221° C.

MS (m/z): 545 (MH$^+$), 543 (M−1).

$^1$H-NMR (DMSO-d$_6$) δ 5.09 (d, J=13 Hz, 1H), 5.47 (d, J=13 Hz, 1H), 6.00 (s, 2H), 6.39 (s, 1H), 6.91 (d, J=8 Hz, 1H), 6.97 (d, J=8 Hz, 1H), 7.02 (s, 1H), 7.33 (d, J=7 Hz, 1H), 7.38 (d, J=4 Hz, 1H), 7.43 (d, J=4 Hz, 1H), 7.60 (m, J=8 Hz, 2H), 7.77 (d, J=5 Hz, 2H), 8.16 (d, J=5 Hz, 3H), 11.90 (s, 1H).

EXAMPLE 49

1-(2,3-Dihydrobenzofuranyl)-2-[5-(2-pyridinyl)-pyrimidin-2-yl]-2,3,4,9-tetrahydro-1H-β-carboline 1-(2,3-dihydrobenzofuranyl)-2,3,4,9-tetrahydro-1H-β-carboline (prepared according to the process as disclosed in WO97/43287, Intermediate 10, page 25) (1.35 g, 4.66 mmol), 2-chloro-5-(2-pyridinyl)-pyrimidine (893 mg, 4.66 mmol) and N,N-diisopropylethylamine (1.4 mL) were stirred in DMF (10 mL, anhydrous) at 120° C. for 16 h. The resulting mixture was quenched with 10% NaCl and extracted with ethyl acetate. The extracted organic layer was washed with 10% NaCl, brine and then dried with MgSO$_4$. The reaction mixture solvent was evaporated and the residue purified by column chromatography (silica gel, ethyl acetate:hexanes=4:6) to yield the product as a white solid.

mp: 170–171° C.

MS (m/z): 446 (MH$^+$), 444 (M−1).

$^1$H-NMR (DMSO-d$_6$) δ 2.85 (d, J=5 Hz, 2H), 3.12 (t, J=8.7 Hz, 2H), 3.27 (d, J=12.4 Hz, 1H), 4.96 (d, J=12.6 Hz, 1H), 6.72 (d, J=8.2 Hz, 1H), 6.99 (t, J=7.4 Hz, 1H), 7.07 (t, J=7.1 Hz, 2H), 7.21 (s, 2H), 7.31 (d, J=8.2 Hz, 2H), 7.47 (d J=7.6 Hz, 1H), 7.85 (d, J=7.8 Hz, 1H), 7.93 (d, J=8 Hz, 1H), 8.62 (d, J=4.5 Hz, 1H), 9.13 (s, 2H), 11.01 (s, 1H).

EXAMPLE 50

1,2,3,4-Tetrahydro-2-[5-(2-pyridinyl)-pyrimidin-2-yl]-3-(2,3-dihydrobenzofuranyl)-9H-pyrrolo-[3,4-b]quinolin-9-one (#61)

Sodium hydride (60% in mineral oil, 182 mg, 4.55 mmol) and 1-(2,3-dihydro-5-benzofuranyl)-2,3,4,9-tetrahydro-2-[5-(2-pyridinyl)-2-pyrimidinyl]-1H-β-carboline (16176–23) (882 mg, 1.98 mmol) (prepared as in Example 49) in DMF (30 mL, anhydrous) were stirred at room temperature for 30 min. Dry air then was bubbled through the reaction mixture for 16 h. Ethyl acetate (200 mL) was added, and the resulting mixture was washed with 10% NaCl solution, brine, and then dried with MgSO$_4$. The reaction mixture solvent was evaporated and the residue triturated with ethyl acetate to yield the product as a white solid.

mp: 201–203° C.

MS (m/z) 460 (MH$^+$); 458 (M−1).

$^1$H NMR (DMSO-d$_6$) δ 3.11 (t, J=8.5 Hz, 2H), 4.46 (t, J=8.5 Hz, 2H), 4.91 (m, 2H), 6.34 (s, 1H), 6.73 (d, J=8.1 Hz, 1H), 7.31 (m, 4H), 7.59 (t, J=8.6 Hz, 2H), 7.84 (d, J=7.1 Hz, 1H), 7.91 (d, J=7.7 Hz, 1H), 8.16 (d, J=7.9 Hz, 1H), 8.60 (d, J=4.5 Hz, 1H), 8.98 (s 1H), 9.12 (s, 2H), 11.90 (s, 1H).

EXAMPLE 50A (R)-1,2,3,4-Tetrahydro-2-[5-(2-pyridinyl)-pyrimidin-2-yl]-3-(2,3-dihydrobenzofuranyl)-9H-pyrrolo-[3,4-b]quinolin-9-one (#65)

A. 1-methyl-5-(2-pyridinyl)-2(1H)pyrimidone

A mixture of 2-(2-pyridinyl)malondialdehyde (5 g, 0.0335 mole), methyl urea (4.72 g, 0.0637 mole), and toluenesulfonic acid (450 mg) was refluxed in toluene (100 mL) in an apparatus fitted with a Dean-Stark water separator for 4 h. The mixture was cooled and the precipitate was filtered. The solid was triturated with water and recrystallized from ethanol to yield the product.

MS m/z (M+H) 188.

$^1$H NMR (DMSO-d$_6$) δ 7.48 (m, 1H), 7.98 (m, 1H), 8.18(d, J=8.0 Hz, 1H), 8.75 (s, 1H), 9.41 (s, 2H).

B. 2-chloro-5-(2-pyridinyl)pyrimidine

A mixture of 1-methyl-5-(2-pyridinyl)-2(1H)pyrimidone (8.994 g, 0.048 mole), phosphorus pentachloride (2.156 g, 0.0104 mole), and phosphorus oxychloride (24 mL) was refluxed at 120° C. for 8 h. POCl$_3$ was distilled out under reduced pressure. The residue was cooled to room temperature and ice-water was added. The mixture was extracted with EtOAc, the organic layer was washed with 15% NaCl solution, brine and dried over MgSO$_4$. Solvent was distilled out under reduced pressure to yield a solid. The water layer was adjusted to pH 6–7 by using saturated Na$_2$CO$_3$, then extracted with EtOAc. The organic layer was washed with 15% NaCl, brine, dried over MgSO$_4$. Solvent was distilled out under reduced pressure to give a solid. After trituration with MeOH, additional product was obtained.

MS m/z (M+H) 192.

$^1$H NMR (DMSO-d$_6$) δ 3.56 (s, 3H), 7.33 (m, 1H), 7.89 (d, J=8.8 Hz, 2H), 8.61 (d, J=4.7 Hz, 1H), 8.95 (s, 1H), 9.31 (s, 1H).

C. (R)-1,2,3,4-tetrahydro-2-[5-(2-pyridinyl)-pyrimidin-2-yl]-3-(3,4-dihydrobenzofuranyl)-9H-pyrrolo-[3,4-b]quinolin-9-one A mixture of (R)-1,2,3,4-Tetrahydro-3-(2,3-dihydrobenzofuran-5-yl)-9H-pyrrolo-[3,4-b]quinolin-9-one, hydrochloride salt (1.273 g, 0.00373 mole) (prepared in example 6A), 2-chloro-5-(2-pyridinyl)pyrimidine (0.714 g, 0.00373 mole), KF (0.216 g, 0.00373 mole), and diisopropylethylamine (2.27 mL) in DMF (45 mL) was heated at 55° C. for 4 h. EtOAc was added, and the mixture was washed with 0.5N citric acid, then with 15% NaCl, brine and dried over MgSO$_4$. Solvent was distilled out under reduced pressure to give a solid. The solid was dissolved in 10% methanol in dichloromethane and purified via column chromatography (EtOAc to 10% CH$_3$OH in EtOAc) to yield the title compound.

mp 231–233° C.

MS m/z (M+H) 460.

$^1$H NMR (DMSO-d$_6$) δ 3.11 (d, J=8.7 Hz, 2H), 4.46 (d, J=8.7 Hz, 2H), 4.92 (m, 2H), 6.34 (d, J=1.6 Hz, 1H), 6.73 (d, J=8.1 Hz, 1H), 7.28 (m, 4H), 7.59 (m, 2H), 7.82 (m, 1H), 7.91 (d, J=8.0, 1H), 8.16 (d, J=8.0, 1H), 8.60, J=4.5 Hz, 1H), 8.98 (s, 1H), 9.12 (s, 1H), 11.92 (s, 1H).

The title compound was dissolved in methanol, one equivalent of 0.02M methane sulfonic acid (in methanol) was added. Solvent was distilled out under reduced pressure to yield the methane sulfonic salt.

[α]=−236.2° (c=1.0333 g/dL, CH$_3$OH).

EXAMPLE 51

2-chloro-5-bromopyrimidine 2-chloro-5-bromopyrimidine was prepared from 2-hydroxypyrimidine (purchased from Frontier Scientific Inc.) according to the procedure disclosed in U.S. Pat. No. 5,693,611, Preparation 6, Column 17.

EXAMPLE 52

1-(3,4-Methylenedioxyphenyl)-2-(5-bromopyrimidin-2-yl)-2,3,4,9-tetrahydro-1H-β-carboline To the solution of 1-(3,4-methylenedioxyphenyl)-2,3,4,9-tetrahydro-1H-β-carboline (4.38 g, 15.0 mmol) (prepared according to the process as disclosed in WO97/43287, Intermediate 7, page 24) and 2-chloro-5-bromopyrimidine (2.90 g, 15.0 mmol) (prepared as in Example 51) in dry degassed DMF (30 ml) was added N,N-diisopropylethylamine (4.2 ml, 30 mmol). The mixture was heated at 120–130° C. overnight. The mixture was then cooled and diluted with ethyl acetate. The solution was washed with 0.5 N citric acid, water and brine, then dried over Na$_2$SO$_4$ and concentrated in vacuo. Purification by flash column (silical gel, hexane:ethyl acetate=6:1, v/v, followed by hexane:ethyl acetate=4:1, v/v) yielded the product as a white solid.

MS (m/z) 451 and 449 (MH$^+$), 447 and 449 (M−1).

$^1$H NMR (CDCl$_3$) δ 2.82–3.02 (m, 2H), 3.30–3.40 (m, 1H), 4.92 (dd, J=18.1 Hz, 1H), 5.92 (d, J=3.2 Hz, 2H), 6.72 (d, J=8.0 Hz, 1H), 6.85 (d, J=8.0 Hz, 1H), 6.95 (s, 1H), 7.02 (s, 1H), 7.13–7.21 (m, 2H), 7.30 (d, J=7.7 Hz, 1H), 7.55 (d, J=7.5 Hz, 1H), 7.73 (s, 1H), 8.34 (s, 2H).

EXAMPLE 53

1,2,3,4-Tetrahydro-2-(5-bromopyrimidin-2-yl)-3-(3,4-methylenedioxyphenyl)-9H-pyrrolo-[3,4-b]quinolin-9-one (#55)

Method A:

A solution of 1-(3,4-methylenedioxyphenyl)-2-(5-bromopyrimidin-2-yl)-2,3,4,9-tetrahydro-1H-β-carboline (1.0 g, 2.2 mmol) (prepared as in Example 52) in dry DMF (40 ml) was cooled in an ice bath. NaH (60% in mineral oil, 0.18 g, 4.4 mmol) was added and the mixture was stirred at 0° C. for 45 min. Dried air was bubbled through the solution and the mixture was allowed to warm to room temperature overnight. The reaction mixture was quenched with water and extracted with ethyl acetate. The organic phase was washed with brine and water, then dried over Na$_2$SO$_4$, concentrated and purified by flash column (silica gel, hexane:ethyl acetate=1:1, v/v, followed by neat ethyl acetate) to yield the product as a white solid.

MS (m/z) 465 and 463 (MH$^+$), 463 and 461 (M−1).

$^1$H NMR (DMSO-d$_6$) δ 4.80 (d, J=8.2 Hz, 1H), 4.89 (dd, J=6.8 Hz, 1H), 5.98 (s, 2H), 6.20 (s, 1H), 6.85–6.93 (m, 2H), 6.98 (s, 1H), 7.34 (t, J=7.3 Hz, 2H), 7.57–7.64 (m, 3H), 8.15 (d, J=8.0 Hz, 2H).

Method B:

To the solution of 1,2,3,4-tetrahydro-3-(3,4-methylenedioxyphenyl)-9H-pyrrolo-[3,4-b]quinolin-9-one (31 mg, 0.1 mmol) (prepared as in Example 5, free base) and 2-chloro-5-bromopyrimidine (19 mg, 0.1 mmol) (prepared as in Example 51) in dry degassed DMF (2 ml) was added N,N-diisopropylethylamine (28 μl, 0.2 mmol). The mixture was heated at 120–130° C. overnight. The solution was cooled, diluted with ethyl acetate and washed by 0.5N citric acid, water and brine, then dried over Na$_2$SO$_4$ and concentrated in vacuo. Purification by flash column (silica gel, hexane:ethyl acetate=1:1, v/v, followed by neat ethyl acetate) yielded the product as a white solid.

MS (m/z) 465 and 463 (MH$^+$), 463 and 461 (M−1).

$^1$H NMR (DMSO-d$_6$) δ 4.80 (d, J=8.2 Hz, 1H), 4.89 (dd, J=6.8 Hz, 1H), 5.98 (s, 2H), 6.20 (s, 1H), 6.85–6.93 (m, 2H), 6.98 (s, 1H), 7.34 (t, J=7.3 Hz, 2H), 7.57–7.64 (m, 3H), 8.15 (d, J=8.0 Hz, 2H).

EXAMPLE 54

1,2,3,4-Tetrahydro-2-[5-(3-pyridinyl)-pyrimidin-2-yl]-3-(3,4-methylenedioxyphenyl)-9H-pyrrolo-[3,4-b]quinolin-9-one (#56)

Method A:

A stirred mixture of palladium(II) acetate (0.8 mg, 3.6 μmol) and 1,1'-bis(diphenylphosphino)ferrocene (dppf) (2.4 mg, 4.3 μmol) in dry DMF (1.0 ml) was warmed to 50° C. for 15 min and then cooled. 1,2,3,4-tetrahydro-2-(5-bromopyrimidin-2-yl)-3-(3,4-methylenedioxyphenyl)-9H-pyrrolo-[3,4-b]quinolin-9-one (20 mg, 43 μmol) (prepared as in Example 53), pyridine-3-boronic acid (6.0 mg, 43 μmol) and triethylamine (8 μl, 60 μmol) were added to the solution and the mixture was heated to 90° C. for 16 h. The solution was diluted with ethyl acetate and filtered through filter paper. The organic phase was washed with brine and water, and then dried over Na$_2$SO$_4$. A small amount of silica gel was added into the solution and the solution was dried in vacuo. Purification by flash column (silica gel, 10% ammonium hydroxide in water:acetonitrile 1:10, v/v) yielded the product as a white solid.

MS (m/z) 460 (M−1).

$^1$H NMR (DMSO-d$_6$) δ 4.88 (d, J=4.1 Hz, 1H), 4.99 (d, J=4.1 Hz, 1H), 5.99 (s, 2H), 6.31 (s, 1H), 6.88 (d, J=7.9 Hz, 1H), 6.96 (d, J=8.1 Hz, 1H), 7.04 (s, 1H), 7.34 (t, J=6.9 Hz, 1H), 7.43–7.50 (m, 1H), 7.56–7.70 (m, 2H), 8.08 (d, J=8.0 Hz, 1H), 8.16 (d, J=7.9 Hz, 1H), 8.53 (d, J=4.1 Hz, 1H), 8.72–8.82 (broad, 1H), 8.89 (s, 2H), 11.87 (s, 1H).

Method B:

A solution of 1-(3,4-methylenedioxyphenyl)-2-[5-(3-pyridinyl)-pyrimidin-2-yl]-2,3,4,9-tetrahydro-1H-β-carboline (100 mg, 0.22 mmol) (prepared as in Example 55), in dry DMF (4.0 ml) was cooled in an ice bath. NaH (60% in mineral oil, 31 mg, 0.78 mmol) was added and the mixture was stirred at 0° C. for 45 min. Dried air was bubbled through the solution and the mixture was allowed to warm to room temperature overnight. The reaction was quenched by water and extracted by ethyl acetate. The organic phase was washed with brine and water, then dried over Na$_2$SO$_4$, concentrated and purified by flash column (silica gel, 10% ammonium hydroxide in water:actonitrile=1:10, v/v) to yield the product as a white solid.

MS (m/z) 460 (M−1).

$^1$H NMR (DMSO-d$_6$) δ 4.88 (d, J=4.1 Hz, 1H), 4.99 (d, J=4.1 Hz, 1H), 5.99 (s, 2H), 6.31 (s, 1H), 6.88 (d, J=7.9 Hz, 1H), 6.96 (d, J=8.1 Hz, 1H), 7.04 (s, 1H), 7.34 (t, J=6.9 Hz, 1H), 7.43–7.50 (m, 1H), 7.56–7.70 (m, 2H), 8.08 (d, J=8.0 Hz, 1H), 8.16 (d, J=7.9 Hz, 1H), 8.53 (d, J=4.1 Hz, 1H), 8.72–8.82 (br, 1H), 8.89 (s, 2H), 11.87 (s, 1H).

EXAMPLE 55

1-(3,4-Methylenedioxyphenyl)-2-[5-(3-pyridinyl)-pyrimidin-2-yl)-2,3,4,9-tetrahydro-1H-β-carboline A stirred mixture of palladium(II) acetate (27 mg, 0.12 mmol) and 1,1'-bis(diphenylphosphino)ferrocene (dppf) (83 mg, 0.15 mmol) in dry DMF (20 ml) was warmed to 50° C. for 15 min and then cooled. 1-(3,4-methylenedioxyphenyl)-2-(5-bromopyrimidin-2-yl)-2,3,4,9-tetrahydro-1H-β-carboline (674 mg, 1.5 mmol) (prepared as in Example 52), pyridine-3-boronic acid (203 mg, 1.7 mmol) and triethylamine (0.3 ml, 2.1 mmol) were added to the solution and the mixture heated to 90° C. for 16 h. The solution was diluted with ethyl acetate and filtered through filter paper. The organic phase was washed with brine and water, then dried over Na$_2$SO$_4$. A small amount of silica gel was added into the solution and the solution was dried in vacuo. Purification by flash column (silica gel, hexane:ethyl acetate=1:1, v/v, followed by hexane:ethyl acetate=1:2, v/v) yielded the product as a white solid.

MS (m/z) 448 (MH$^+$) and 446 (M−1).

$^1$H NMR (CDCl$_3$) δ 2.85–3.10 (m, 2H), 3.33–3.48 (m, 1H), 5.06 (dd, J=8.5 Hz, 1H), 5.94 (d, J=4.7, 2H), 6.73 (d, J=8.0, 1H), 6.90 (d, J=8.0, 1H), 7.02 (s, 1H), 7.13–7.23 (m, 2H), 7.32–7.42 (m, 2H), 7.56 (d, J=7.4 Hz, 1H) 7.79–7.84 (m, 2H), 8.58 (s, 1H), 8.60 (s, 2H) 8.77 (s, 1H).

EXAMPLE 56

1,2,3,4-Tetrahydro-2-[5-(4-pyridinyl)-pyrimidin-2-yl]-3-(3,4-methylenedioxyphenyl)-9H-pyrrolo-[3,4-b]quinolin-9-one (#57)

A stirred mixture of 1,2,3,4-tetrahydro-2-(5-bromopyrimidin-2-yl)-3-(3,4-methylenedioxyphenyl)-9H-pyrrolo-[3,4-b]quinolin-9-one (46 mg, 0.1 mmol) (prepared as in Example 53), (PPh$_3$)$_4$Pd (3.5 mg, 3.0 μmol) and 4-tri-n-butylstannylpyridine (37 mg, 0.1 mmol) in dry DMF (2.0 ml) was heated at 140° C. for 12 h. More catalyst (3.5 mg) was added and the mixture was refluxed for 4 h and then cooled. The solution was diluted with ethyl acetate and filtered through filter paper. The organic phase was washed with brine and water, then dried over Na$_2$SO$_4$. A small amount of silica gel was added into the solution and dried in vacuo. Purification by flash column (silica gel, neat acetonitrile followed by 10% ammonium hydroxide in water:actonitrile=1:10, v/v) yielded the product as a white solid.

MS (m/z) 460 (M−1).

$^1$H NMR (DMSO-d$_6$) δ 4.93 (d, J=4.2 Hz, 1H), 5.00 (d, J=4.2 Hz, 1H), 6.01 (s, 2H), 6.33 (s, 1H), 6.90 (d, J=8.0 Hz, 1H), 6.98 (d, J=8.0 Hz, 1H), 7.05 (s, 1H), 7.34 (broad, 1H), 7.62 (broad, 2H), 7.77 (d, 2H), 8.19 (d, J=7.9 Hz, 1H), 8.61 (broad, 2H), 8.78 (broad, 1H), 9.00 (broad, 1H).

EXAMPLE 57

1,2,3,4-Tetrahydro-3-(3,4-methylenedioxyphenyl)-2-(5-(2-bromo)-furoyl)-9H-pyrrolo[3,4-b]quinolin-9-one (#30)

5-Bromo-2-furoic acid (1.44 g, 7.54 mmol) in THF (20 mL) was stirred with oxalyl chloride (1.06 mL, 7.54 mmol) at room temperature. To the mixture was added 2 drops of DMF resulting in a vigorous reaction with evolution of gas. After the evolution of gas ceased, an additional quantity of oxalyl chloride (0.1 mL, 0.71 mmol) was introduced via syringe and the mixture was stirred at room temperature for 10 min and then stirred at 90° C. for 10 min. Solvent and excess oxalyl chloride were removed in vacuo, resulting in a pale yellow crystalline solid. To the solid was added THF (20 mL) and a solution of 3-(2,3-dihydro-5-benzofuran)-1,2,3,4-tetrahydro-9H-pyrrolo[3,4-b]quinolin-9-one (2.1 g) (prepared as in Example 6), in THF (20 mL). Et$_3$N (4.55 mL, 32.6 mmol) and a catalytic amount of DMAP (40 mg) were then added to the reaction mixture. A few drops of DMF were added, resulting in a clear reaction mixture. The reaction mixture was stirred at room temperature for 4 h. The reaction mixture solvent was evaporated resulting in a solid residue. The residue was re-dissolved in CHCl$_3$ (200 mL), washed with water (3×200 mL) and the organic layer dried over MgSO$_4$. The organic solvent was evaporated to yield the product as a off-white solid.

MS (m/z): 480, (MH$^+$), 478 (M−1).

$^1$H NMR CDCl$_3$ δ 5.03 (d, 1H, J=15.5 Hz), 5.23 (d, 1H, J=15.5 Hz), 5.85 (d, 2H, J=8.0 Hz), 6.40 (m, 2H), 6.56 (m, 1H), 6.81 (m, 2H), 7.00 (d, 1H, J=4.3 Hz), 7.32 (t, 1H, J=8.6 Hz), 7.53 (t, 1H, J=8.6 Hz), 7.65 (d, 1H, J=8.6 Hz), 8.38 (d, 1H, J=8.6 Hz), 12.8 (s, 1H).

EXAMPLE 58

4-(4-Methyl)-piperazinylcarbonyl benzeneboronic acid

4-Carboxybenzeneboronic acid (0.332 g, 2 mmol), 1-methylpiperazine (0.22 mL, 2 mmol) and PyBrOP (0.9334 g, 2 mmol) were stirred with DIPEA (0.696 mL, 4 mmol) in DMF (7 mL) at room temperature for 16 h. Preparatory TLC (10% MeOH/CHCl$_3$) yielded the product as white solid.

MS (m/z): 251 (MH$^+$), 249 (M−1).

$^1$H NMR CD$_3$OD δ 2.36 (s, 3H), 2.43 (s, 2H), 2.57 (s, 2H), 3.51 (s, 2H), 3.82 (s, 2H), 7.34 (s, 2H), 7.76 (s, 2H).

EXAMPLE 59

1,2,3,4-Tetrahydro-3-(3,4-methylenedioxyphenyl)-2-(5-(4-(1-(4-methyl)piperazinylcarbonyl)-phenyl)-furoyl)-9H-pyrrolo[3,4-b]quinolin-9-one (#44)

1,2,3,4-Tetrahydro-3-(3,4-methylenedixoyphenyl)-2-(5-(2-bromo-furoyl)-9H-pyrrolo[3,4-b]quinolin-9-one (59.6 mg, 0.12 mmol) (prepared as in Example 57), was stirred with Pd(PPh$_3$)$_4$ (7.37 mg, 0.0062 mmol) in dioxane (5.5 mL) with N$_2$ bubbling for 10 min. A solution of 4-(4-methyl)-piperazinylcarbonyl benzeneboronic acid (37.0 mg, 0.15 mmol) and K$_2$CO$_3$ (51.5 mg, 0.37 mmol) in H$_2$O (1.1 mL) was then added. The reaction mixture was stirred at 100° C. for 1 h. The solvent was evaporated, the residue purified by preparatory TLC (10% MeOH/CHCl$_3$) and then triturated with ether/MeOH (15 mL/1 mL), to yield the product as a pale yellow powder.

MS (m/z): 603 (MH$^+$), 601 (M−1).

$^1$H NMR CD$_3$OD δ 2.32 (s, 3H), 2.53~2.62 (m, 4H), 3.53 (broad s, 2H), 3.83 (broad s, 2H), 5.17 (d, 1H, J=15.5 Hz), 5.41 (d, 1H, J=15.5 Hz), 5.83 (s, 2H), 6.22 (s, 1H), 6.70 (m, 1H), 6.82 (m, 2H), 7.03 (m, 1H), 7.25~7.34 (m, 2H), 7.46~7.56 (m, 4H), 7.93 (d, 2H, J=8.6 Hz), 8.31 (d, 2H, J=8.6 Hz).

EXAMPLE 59A (R)-1,2,3,4-Tetrahydro-3-(3,4-methylenedioxyphenyl)-2-(5-(4-(1-(4-methyl)-piperazinylcarbonyl)-phenyl)-furoyl)-9H-pyrrolo[3,4-b]quinolin-9-one (#69)

A 5-(4-(4-methyl)-piperazinylcarbonyl phenyl)furoic acid, methyl ester

A mixture of 4-(4-methyl)-piperazinylcarbbnyl benzeneboronic acid (prepared as in Example 58) (1.31 g, 5.28 mmol), methyl bromofuroic ester (1.08 g, 5.28 mmol (prepared from 5-bromofuroic acid in HCl/MeOH for 5 h at room temperature) was degassed by $N_2$ bubbling in dioxane (45 mL) and $H_2O$ (9 mL) for 10 min. To this was added with $Pd(PPh_3)_4$ (0.627 g, 0.528 mmol) and $K_2CO_3$ (2.185 g, 15.84 mmol). The solution was stirred at 100° C. for 3 h. Solvent was evaporated and the residue was dissolved in $CH_2Cl_2$ (100 mL). This was washed with brine (3×100 mL), dried over $MgSO_4$, concentration under vacuum and the crude product purified by silica gel column (5% $CH_3OH/CHCl_3$) to yield the product as yellow solid.

MS (m/z): 315 (MH$^+$), 313 (M−1).

$^1$H NMR δ CDCl$_3$ 2.32~2.48 (m, 7H), 3.48 (s, 2H), 3.80 (s, 2H), 3.92 (s, 3H,), 6.81 (d, 1H, J=2.0 Hz), 7.24 (d, 1H, J=2.0 Hz), 7.49 (d, 2H, J=7.9 Hz), 7.83 (d, 2H, J=7.9 Hz). Rf=0.51 (10% $CH_3OH/CHCl_3$).

B. 5-(4-(4-methyl)-piperazinylcarbonyl phenyl)furoic acid

To the product from Step A above (5-(4-(4-methyl)-piperazinylcarbonyl phenyl)furoic acid, methyl ester) (1.08 g, 3.29 mmol), dissolved in THF (98.7 mL) was added LiOH (16.45 mL, 0.2 N in $H_2O$). The solution was stirred at room temperature for 3.5 h and was neutralized by HCl (3.29 mL, 1.0 M in ether). After concentration, the crude material was used without further purification.

MS (m/z): 329 (MH$^+$), 327 (M−1).

$^1$H NMR δ CD$_3$OD 2.35 (s, 3H), 2.36~2.58 (br s, 4H,), 3.48 (s, 2H), 3.85 (s, 2H), 6.90 (d, J=2.0 Hz), 7.02 (d, 1H, J=2.0 Hz), 7.46 (d, 2H, J=7.9 Hz), 7.95 (d, 2H, J=7.9 Hz).

C. (R)-1,2,3,4-Tetrahydro-3-(3,4-methylenedioxyphenyl)-2-{5-[4-(1-(4-methyl)-piperazinylcarbonyl)-phenyl]furoyl}-9H-pyrrolo[3,4-b]quinolin-9-one (#69)

A mixture of R-1,2,3,4-tetrahydro-3-(3,4-methylenedioxyphenyl)-9H-pyrrolo-[3,4-b]quinolin-9-one, hydrochloride salt (1.12 g, 3.29 mmol) (prepared as in Example 5A), and the product from Step B (1.034 g, 3.29 mmol) was stirred with PyBroP (1.535 g, 3.29 mmol) and diisopropyl ethyl amine (1.716 mL, 9.87 mmol) in DMF (30 mL) at room temperature for 12 h. The reaction mixture was diluted with $CH_2Cl_2$ (75 mL) and EtOAc (75 mL). This was purified on a silica gel column (neat $CH_2Cl_2$, to 2.5% $CH_3OH/CH_2Cl_2$) to yield the product as an off-white solid.

MS (m/z): 603 (MH$^+$), 601 (M−1).

$^1$H NMR δ CD$_3$OD δ 2.32 (s, 3H), 2.43~2.55 (m, 4H), 3.53 (br s, 2H), 3.83 (brs, 2H), 5.25 (d, 1H, J=15.5 Hz), 5.51 (d, 1H, J=15.5 Hz), 5.87 (s, 2H), 6.29 (s, 1H), 6.70 (m, 1H), 6.82 (m, 2H), 7.08 (m, 1H), 7.20~7.39 (m, 2H), 7.46~7.58 (m, 4H), 8.01 (d, 2H, J=8.6 Hz), 8.31 (d, 2H, J=8.6 Hz).

HPLC Chiralpak OD 4.6×250 mm, 1% DEA/MeOH, Tr=4.846 min).

EXAMPLE 60

1,2,3,4-Tetrahydro-3-(3,4-methylenedioxyphenyl)-2-(5-(2-(4-hydroxy)phenyl)-furoyl)-9H-pyrrolo[3,4-b]quinolin-9-one, sodium salt (Na salt of #22)

Following the procedure outlined in Example 59, with appropriate substitution of reagents, the product was obtained as a off-white solid.

MS (m/z): 493 (MH$^+$), 491 (M−1).

$^1$H NMR CDCl$_3$ δ 5.21 (d, 1H, J=15.6 Hz), 5.57 (d, 1H, J=15.6 Hz), 6.12 (s, 2H), 6.51 (s, 2H) 6.68 (d, 1H, J=4.1 Hz), 6.98~7.14 (m, 4H), 7.38 (s, 1H), 7.48 (t, 1H, J=8.6 Hz), 7.62~7.79 (m, 4H), 8.08 (s, 1H), 8.28 (d, 1H, J=8.6 Hz).

EXAMPLE 61

(4-(2-(1-Pyrrolidinyl)ethoxy)phenyl)boronic acid (Prepared According to the Procedure Described by Hoye, T. R. and Chen, M. in *J. Org. Chem.* 1996, 61, 7940.)

To a solution of 1-[2-(4-bromophenoxy)ethyl]-pyrrolidine (2.70 g, 10 mmol) in THF (40 mL) was added n-butyl lithium (6.9 mL 1.6 M in hexanes, 11 mmol) at −78° C. The reaction mixture was stirred at −78° C. for 15 min and then at 0° C. for 15 min. Trimethyl borate (2.5 mL, 22 mmol) was then added to the reaction mixture at 0° C. The mixture was gradually warmed to room temperature overnight. Methyl borate in the reaction mixture was hydrolyzed by reacting with saturated NH$_4$Cl aqueous solution (100 mL) at room temperature for 30 min. The upper organic layer was collected. The aqueous layer was extracted with CHCl$_3$ (2×100 mL). The organic layers were combined, washed with brine (2×100 mL) and dried with MgSO$_4$. The solvent was evaporated, resulting in a dense oil which was purified by column chromatograph (10% MeOH/CHCl$_3$ and 1% Et$_3$N) to yield the product as a white solid.

MS (m/z): 236, (MH$^+$), 234 (M−1).

$^1$H NMR CD$_3$OD δ 1.81 (m, 4H), 2.67 (m, 4H), 2.89 (t, 2H, J=6.0 Hz), 4.08 (t, 2H, J=6.0 Hz), 6.74 (d, 2H, J=8.6 Hz), 7.62 (d, 2H, J=8.6 Hz).

EXAMPLE 62

1,2,3,4-Tetrahydro-3-(3.4-methylenedioxyphenyl)-2-(5-(4-(2-(1-pyrrolidinyl)ethoxy)phenyl)-furoyl)-9H-pyrrolo[3,4-b]quinolin-9-one (#45)

Following the procedure outlined in Example 59, with appropriate substitution of reagents, the product was obtained as a off-white solid.

MS (m/z): 590, (MH$^+$), 588 (M−1).

$^1$H NMR CDCl$_3$ δ 2.18 (s, 4H), 2.55 (s, 4H), 2.75 (m, 2H), 2.90 (m, 2H), 4.67 (d, 1H, J=15.6 Hz), 4.82 (d, 1H, J=15.6 Hz), 5.18 (s, 2H), 5.81 (m, 1H), 6.08 (m, 1H), 6.21 (s, 2H), 6.35 (s, 1H), 6.60 (s, 1H), 6.82 (m, 3H), 6.92 (m, 1H), 7.04 (m, 1H), 7.21 (s, 2H), 7.62 (d, 1H, J=8.6 Hz).

EXAMPLE 63

3-(2,3-Dihydro-5-benzofuranyl)-1,2,3,4-tetrahydro-2-(benzyl)-9H-pyrrolo[3,4-b]quinolin-9-one (#60)

1-(2,3-Dihydro-5-benzofuranyl)-2-benzyl-2,3,4,9-tetrahydro-1H-β-carboline (prepared as in Example 2) (5.25 g, 13.81 mmol), potassium dioxide (3.92 g, 55.24 mmol) and 18-crown-6 (3.65 g, 13.81 mmol) were mixed with DMF (100 mL) in a 200 mL flask. The reaction mixture was maintained at room temperature overnight. The reaction mixture was slowly added into a separate 500 mL flask containing a mixture of EtOAc (172 mL), H$_2$O (172 mL) and 1N aqueous HCl (50 mL). The mixture was observed to produce tiny gas bubbles. The reaction mixture was stirred at 0° C. for 30 min, resulting in the formation of a precipitate at the surface of the two liquid layers. The precipitate was collected by filtration, washed with H$_2$O (20 mL) and then dried in a vacuum oven to yield the product as a off-white solid.

MS (m/z): 395, (MH$^+$), 393 (M−1).

$^1$H NMR CDCl3 d 3.12 (t, 2H, J=8.7 Hz), 3.50–3.65 (m, 2H), 3.99 (d, 1H, J=13.0 Hz), 4.22 (d, 1H, J=13.0 Hz), 4.55 (t, 2H, J=8.7 Hz), 4.91 (s, 1H), 6.74 (d, 1H, J=8.7 Hz), 7.11–7.32 (m, 9H), 7.48 (t, 1H, J=8.7 Hz), 8.30 (t, 1H, J=8.7 Hz).

EXAMPLE 64

3-(3,4-Methylenedioxyphenyl)-1,2,3,4-tetrahydro-2-[5-(3-trifluoromethyl)phenyl-2-furoyl]-9H-pyrrolo[3,4-b]quinolin-9-one (#13)

Following the procedure outlined in Example 63, with appropriate substitution of reagents, 1-(3,4-methylenedioxyphenyl)-2-benzyl-2,3,4,9-tetrahydro-1H-β-carboline (0.381 g, 0.719 mmol) was reacted to yield the product as a off-white solid. Note that for full formation of the precipitate, the two liquid reaction mixtures were maintained at room temperature for 48 h, rather than overnight.

MS (m/z): 545 (MH$^+$), 567 (M+23), 543 (M−1).

$^1$H-NMR (DMSO-d$_6$) δ 5.09 (d, J=14 Hz, 1H), 5.46 (d, J=14 Hz, 1H), 5.99 (s, 2H), 6.39 (s, 1H), 6.91 (d, J=8 Hz, 1H), 6.97 (d, J=9 Hz, 1H), 7.02 (s, 1H), 7.33 (d, J=8 Hz, 1H), 7.38 (d, J=4 Hz, 1H), 7.43 (d, J=4 Hz, 1H), 7.60 (m, J=8 Hz, 2H), 7.77 (d, J=5 Hz, 2H), 8.16 (d, J=4 Hz, 3H), 11.55 (s, 1H).

EXAMPLE 65

1-(3,4-Methylenedioxyphenyl)-2-[4-(4-methoxyphenyl)thiazol-2-yl]-2,3,4,9-tetrahydro-1H-β-carboline A. 1-(3,4-Methylenedioxyphenyl)-2-[3-(fluorenylmethyloxycarbonyl) thiocarbamoyl]-2,3,4,9-tetrahydro-1H-β-carboline A mixture of 1-(3,4-methylenedioxyphenyl)-2,3,4,9-tetrahydro-1H-β-carboline (2.66 g, 9.08 mmol) (prepared according to the process as disclosed in WO97/43287, Intermediate 7, page 24) and Fmoc-isothiocyanate (2.82 g, 10.14 mmol) was dissolved in dry dichloromethane (50 mL). The mixture was stirred for 16 hours at ambient temperature, and then concentrated in vacuo. Purification by flash chromatography (0–10% methanol in dichloromethane) yielded the protected thiourea as a pale yellow solid.

MS (m/z): 574 (MH$^+$).

$^1$H-NMR (CDCl$_3$) δ 2.86 (dd, J=12.9, 5.1 Hz, 1H), 3.09 (dt, J=17.1, 6.9 Hz, 1H), 3.56 (dt, J=12.9, 5.1 Hz, 1H), 4.19 (t, J=6.9 Hz, 1H), 4.43–4.53 (m, 2H), 5.91 (s, 2H), 6.70 (d, J=8 Hz, 1H), 6.90 (br d, J=7.6 Hz, 1H), 6.97 (br s, 1H), 7.11–7.78 (series of m, 17H).

B. 1-(3,4-Methylenedioxyphenyl)-2-(thiocarbamoyl)-2,3,4,9-tetrahydro-1H-β-carboline A solution of the protected thiourea from Part A (4.78 g, 8.33 mmol) in 20% (v/v) piperidine in methanol was heated to reflux for 5 h. The mixture was concentrated in vacuo to yield a crude residue which was purified by flash chromatography (SiO$_2$, 0–10% methanol in dichloromethane) to yield a yellow solid.

MS (m/z): 352 (MH$^+$).

$^1$H-NMR (CDCl$_3$) δ 2.69–2.87 (series of m, 2H), 3.10–3.19 (m, 1H), 4.24 (br s, 1H), 6.00 (d, J=3.3 Hz, 2H), 6.72 (d, J=8.0 Hz, 1H), 6.87 (d, J=8.0 Hz, 1H), 7.00–7.11 (series of m, 3H), 7.30 (d, J=8.0 Hz, 1H), 7.46 (d, J=7.7 Hz, 1H), 7.74 (br s, 3H), 11.06 (s, 1H).

C. 1-(3,4-Methylenedioxyphenyl)-2-[4-(4-methoxyphenyl)thiazol-2-yl]-2,3,4,9-tetrahydro-1H-β-carboline To a solution of the thiourea from Part B (223 mg, 0.63 mmol) in a 1:1 mixture of dioxane:ethanol (5 mL) was added 4-methoxyphenyl-2'-bromoacetophenone (175 mg, 0.76 mmol) and triethylamine (0.40 mL). The mixture was heated to 70° C. for 3 h, cooled to room temperature and concentrated in a rotary evaporator. The residue was purified by flash chromatography (SiO$_2$, 0–10% methanol in dichloromethane) to yield a colorless solid.

MS (m/z): 482 (MH$^+$).

$^1$H-NMR (CDCl$_3$) δ 2.86–2–3.07 (series of m, 2H), 3.61–3.71 (m, 1H), 3.78 (s, 3H), 3.91–4.02 (m, 1H), 5.99 (d, J=3.3 Hz, 2H), 6.58 (s, 1H), 6.80–7.11 (series of m, 8H), 7.31 (d, J=7.8 Hz, 1H), 7.48 (d, J=7.6 Hz, 1H), 7.82 (d, J=8.7 Hz, 2H), 10.93 (s, 1H).

EXAMPLE 66

1-(3,4-Methylenedioxyphenyl)-2-[4-phenylthiazol-2-yl]-2,3,4,9-tetrahydro-1H-β-carboline A. 1-(3,4-Methylenedioxyphenyl)-2-[3-(fluorenylmethyloxycarbonyl) thiocarbamoyl]-2,3,4,9-tetrahydro-1H-β-carboline A mixture of 1-(3,4-methylenedioxyphenyl)-2,3,4,9-tetrahydro-1H-β-carboline (2.66 g, 9.08 mmol) (prepared according to the process as disclosed in WO97/43287, Intermediate 7, page 24) and Fmoc-isothiocyanate (2.82 g, 10.14 mmol) was dissolved in dry dichloromethane (50 mL). The mixture was stirred for 16 hours at ambient temperature, and then concentrated in vacuo. Purification by flash chromatography (0–10% methanol in dichloromethane) yielded the protected thiourea as a pale yellow solid.

MS (m/z): 574 (MH$^+$).

$^1$H-NMR (CDCl$_3$) δ 2.86 (dd, J=12.9, 5.1 Hz, 1H), 3.09 (dt, J=17.1, 6.9 Hz, 1H), 3.56 (dt, J=12.9, 5.1 Hz, 1H), 4.19 (t, J=6.9 Hz, 1H), 4.43–4.53 (m, 2H), 5.91 (s, 2H), 6.70 (d, J=8 Hz, 1H), 6.90 (br d, J=7.6 Hz, 1H), 6.97 (br s, 1H), 7.11–7.78 (series of m, 17H).

B. 1-(3,4-Methylenedioxyphenyl)-2-(thiocarbamoyl)-2,3,4,9-tetrahydro-1H-β-carboline A solution of the protected thiourea from Part A (4.78 g, 8.33 mmol) in 20% (v/v) piperidine in methanol was heated to reflux for 5 h. The mixture was concentrated in vacuo to yield a crude residue which was purified by flash chromatography (SiO$_2$, 0–10% methanol in dichloromethane) to yield a yellow solid.

MS (m/z): 352 (MH$^+$).

$^1$H-NMR (CDCl$_3$) δ 2.69–2.87 (series of m, 2H), 3.10–3.19 (m, 1H), 4.24 (br s, 1H), 6.00 (d, J=3.3 Hz, 2H), 6.72 (d, J=8.0 Hz, 1H), 6.87 (d, J=8.0 Hz, 1H), 7.00–7.11 (series of m, 3H), 7.30 (d, J=8.0 Hz, 1H), 7.46 (d, J=7.7 Hz, 1H), 7.74 (brs, 3H), 11.06 (s, 1H).

C. 1-(3,4-Methylenedioxyphenyl)-2-[4-phenylthiazol-2yl]-2,3,4,9-tetrahydro-1H-β-carboline To a solution of the thiourea of Part B (227 mg, 0.65 mmol) was added β-bromoacetophenone (159 mg, 0.80 mmol) and triethylamine (0.40 mL). This mixture was heated to 70° C. for 3 h, cooled to room temperature and concentrated in a rotary evaporator. The residue was purified by flash chromatography (SiO$_2$, 0–10% methanol in dichloromethane) to yield a pale yellow solid.

MS (m/z): 452 (MH$^+$).

$^1$H-NMR (CDCl$_3$) δ 2.87–2–3.06 (series of m, 2H), 3.63–3.73 (m, 1H), 3.93–3.99 (m, 1H), 5.99 (d, J=3.3 Hz, 2H), 6.59 (s, 1H), 6.81–7.11 (series of m, 5H), 7.25–7.69 (series of m, 6H), 7.89 (d, J=7.4 Hz, 2H), 10.95 (s, 1H).

EXAMPLE 67

3-(2,3-Dihydro-benzofuran-5-yl)-1,2,3,4-tetrahydro-3R-9H-pyrrolo[3,4-b]quinolinone A: [2-(1H-Indol-3-yl)-ethyl]-(1-naphthalen-1-yl-ethyl)-amine was prepared according to the process described in Kawate, T.; Yamanaka, M.; Nakagawa, M. in *Heterocycles*, 1999, 50, 1033

B: R- and S-Diastereomers of 1-(-2,3-dihydro-benzofuran-5-yl)-2-(1R-1-naphthalen-1-yl-ethyl)-2,3,4,9-tetrahydro-1H-β-carboline

[2-(1H-Indol-3-yl)-ethyl]-(1-naphthalen-1-yl-ethyl)-amine (1.0 g, 3.18 mmol) and 2,3-dihydro-benzofuran-5-carbaldehyde (2.356 g, 15.92 mmol) were stirred in p-xylene (20 mL) at 165° C. for 7 h. To the reaction mixture was added silica gel (10 g) and hexane (200 mL). The reaction mixture was filtered and the colorless filtrate was discarded. The silica gel was washed with ethyl acetate (100 mL). The ethyl acetate solvent was evaporated, the concentrated crude material was dissolved in a small amount of $CH_2Cl_2$ and packed on a silica gel column. The column was eluted with 5% ethyl acetate/hexane to yield two diastereomers.

1-(-2,3-dihydro-benzofuran-5-yl)-2-(1R-1-naphthalen-1-yl-ethyl)-2,3,4,9-tetrahydro-1S-1H-β-carboline (the non-desired diastereomer A) (Rf=0.59 in 30% EtOAc/Hexane) was obtained as yellow solid.

$^1$H NMR 300 MHz (CDCl$_3$) δ 1.58, 1.62 (d, 3H, J=6.5 Hz), 2.61 (m, 1H), 2.91 (m, 1H), 3.05~3.20 (m, 4H), 4.51 (t, 2H, J=8.8 Hz), 4.72 (m, 1H), 4.81 (s, 1H), 6.68 (m, 1H), 6.92 (m, 4H), 7.05~7.65 (m, 5H), 7.70~7.95 (m, 4H).

MS (m/z) MH$^+$(445), MH$^-$(443).

1-(-2,3-dihydro-benzofuran-5-yl)-2-(1R-1-naphthalen-1-yl-ethyl)-2,3,4,9-tetrahydro-1 R-1H-β-carboline (the desired diastereomer B) (Rf=0.51 in 30% EtOAc/Hexane) was obtained as a yellow solid.

$^1$H NMR 300 MHz (CDCl$_3$) δ 1.58 (d, 3H, J=6.5 Hz), 2.65 (m, 1H), 2.91 (m, 2H), 3.05 (t, 2H, J=8.8 Hz), 3.15 (m, 1H), 4.51 (t, 2H, J=8.8 Hz), 4.65 (m, 1H), 5.10 (s, 1H), 6.68 (m, 1H), 6.85 (s, 2H), 7.11 (m, 2H), 7.20~7.50 (m, 5H), 7.68 (m, 2H), 7.81 (m, 1H), 8.21 (m, 1H).

MS (m/z) MH$^+$(445), MH$^-$(443).

C: Conversion of S-Diastereomer to R-Diastereomer 1-(-2,3-dihydro-benzofuran-5-yl)-2-(1R-1-naphthalen-1-yl-ethyl)-2,3,4,9-tetrahydro-1S-1H-β-carboline (the non-desired diastereomer A) (190 g, 0.428 mmol) was stirred in 1000 mL $CH_2Cl_2$ with TFA (52 mL, 701 mol) at room temperature overnight. The reaction was quenched with NaOH (35 g, 0.875 mol) in water (100 mL). The reaction mixture was mixed well and then let stand for 0.5 hours, during which time a precipitate formed. The precipitate was filtered, the solid washed with water and dried under high vacuum to yield the product as a solid.

$^1$H NMR was identical to that of 1-(-2,3-dihydro-benzofuran-5-yl)-2-(1R-1-naphthalen-1-yl-ethyl)-2,3,4,9-tetrahydro-1R-1H-β-carboline (the desired diastereomer).

D: 3-(2,3-Dihydro-benzofuran-5-yl)-2-(1 R-1-naphthalen-1-yl-ethyl)-1,2,3,4-tetrahydro-3R-9H-pyrrolo[3,4-b]quinolinone 1-(2,3-Dihydro-benzofuran-5-yl)-2-(1R-1-naphthalen-1-yl-ethyl)-2,3,4,9-tetrahydro-1R-1H-β-carboline (0.6469 g, 1.46 mmol) and potassium-t-butoxide (0.279 g, 2.48 mmol) were stirred in DMF (14 mL) at room temperature. O$_2$ gas was bubbled into the reaction mixture overnight. The reaction was quenched with HCl (2.48 mL, 1 N aqueous). Ethyl acetate (50 mL) and H$_2$O (50 mL) were then added. The organic layer was separated. The aqueous layer was extracted with ethyl acetate (50 mL) and $CH_2Cl_2$ (50 mL). The organic layers were washed with brine (3×50 mL) and dried over MgSO$_4$. The resulting product was concentrated and purified via silica gel (2% methanol/$CH_2Cl_2$) to yield the product as a yellow solid.

$^1$H NMR 300 MHz (CDCl$_3$) δ 1.65 (d, 3H, J=6.5 Hz), 3.05 (t, 2H, J=8.8 Hz), 4.01 (m, 2H), 4.51 (t, 2H, J=8.8 Hz), 4.68 (m, 1H), 5.31 (s, 1H), 6.62 (s, 1H), 6.88~7.89 (m, 12H), 8.25 (d, 1H).

MS (m/z) MH$^+$(459), MH$^-$(457).

E: 3-(2,3-Dihydro-benzofuran-5-yl)-1,2,3,4-tetrahydro-3R-9H-pyrrolo[3,4-b]quinolinone 3-(2,3-Dihydro-benzofuran-5-yl)-2-(1R-1-naphthalen-1-yl-ethyl)-1,2,3,4-tetrahydro-3R-9H-pyrrolo[3,4-b]quinolinone (24 mg, 0.0524 mmol) was dissolved in 5 mL ethanol. To the reaction mixture was added 10% Pd/C (50 mg) and HCl (1.0 M in diethyl ether (0.05 mL, 0.05 mL)). The reaction mixture was stirred under 35 psi of H$_2$ gas for 3 hours at room temperature. The catalyst was filtered away on a plug of Celite. The reaction mixture was concentrated to yield crude product. Purification by preparative TLC (5% MeOH/$CH_2Cl_2$) yielded the title product as yellowish solid.

$^1$H NMR 300 MHz (CDCl$_3$) δ 13.23 (d, 2H, J=8.8 Hz), 4.59 (t, 2H, J=8.8 Hz), 4.78 (m, 2H), 0.32 (s, 1H), 6.88 (m, 1H), 7.31 (m, 2H), 7.72 (m, 3H), 8.32 (m, 1H).

MS (m/z) MH$^+$ (305), MH$^-$ (303).

EXAMPLE 68

3-Benzo[1,3]dioxol-5-yl-2-(5-bromo-furan-2-carbonyl)-1,2,3,4-tetrahydro-pyrrolo[3,4-b]quinolin-9-one To a solution of 5-bromo-2-furoic acid (2.1 g, 6.856 mmol) in THF (20 mL) was added oxalyl chloride (0.66 mL, 7.541 mmol). 2 drops of DMF were then added to the reaction mixture, with bubbles of CO observed to come out vigorously. Oxalyl chloride ((COCl)$_2$) (0.1 mL) was then added. The reaction mixture was stirred at room temperature for 10 min and at 90° C. for 10 min. Solvent and excess (COCl)$_2$ were taken off under vacuum to yield 5-bromo-furan-2-carbonyl chloride as a pale yellow crystalline solid.

The solid 5-bromo-furan-2-carbonyl chloride was dissolved in THF (20 mL). A solution of 3-(2,3-dihydro-benzofuran-5-yl)-1,2,3,4-tetrahydro-9H-pyrrolo[3,4-b]quinolinone (2.1 g, 6.856 mmol) in THF (20 mL) was then added. Triethylamine (4.55 mL, 32.64 mmol) and DMAP (40 mg, 0.327 mmol) were then added in sequentially. A few drops of DMF were added to the reaction mixture to keep the solution clear. The reaction mixture was stirred at room temperature for 4 hours and then concentrated under vacuum. The residue was dissolved in CHCl$_3$ (200 mL) and washed with H$_2$O (3×200 mL). The organic layer was dried over MgSO$_4$ to yield the title product as an off-white solid. No further purification was necessary.

$^1$H NMR 300 MHz (CD$_3$OD) δ 4.87 (d, 1H, J=11.5 Hz), 5.19 (d, 1H, J=11.5 Hz), 5.78 (m, 2H), 6.24–7.60 (m, 8H), 8.39 (d, 1H, J=8.3 Hz).

MS (m/z): 479, 481 (MH$^+$), 479, 477 (MH$^-$).

EXAMPLE 69 THROUGH 79

General Procedure

3-Benzo[1,3]dioxol-5-yl-2-(5-bromo-furan-2-carbonyl)-1,2,3,4-tetrahydro-pyrrolo[3,4-b]quinolin-9-one (0.100 g, 0.2086 mmol) was stirred with a mixture of a suitably substituted boronic acid (0.2296 mmol, 1.1 eq), Pd(PPh$_3$)$_4$ (12.4 mg, 0.01043 mmol), K$_2$CO$_3$ (86.4 mg, 0.6258 mmol) in 1,4-dioxane (8 mL) and H$_2$O (2 mL) was degased under N$_2$ and then stirred at 100° C. for 1.5 hours. The crude reaction mixture was loaded onto a silica gel preparative TLC plate and eluted with 5% CH$_3$OH/CH$_2$CL$_2$ to yield the isolated product as a solid.

Compound #110 (Reacted with Phenyl Boronic Acid)

$^1$H NMR 300 MHz (CD$_3$OD) δ 5.19 (d, 1H, J=11.5 Hz), 5.42 (d, 1H, J=11.5 Hz), 5.93 (s, 2H), 6.38 (s, 1H), 6.74~8.31 (m, 14H).

MS (m/z): 477 (MH$^+$), 475 (MH$^-$).
Compound #111 (Reacted with 4-methylthiophenyl Boronic Acid)
$^1$H NMR 300 MHz (CD$_3$OD) δ 5.21 (d, 1H, J=11.5 Hz), 5.44 (d, 1H, J=11.5 Hz), 5.91 (s, 2H), 6.40 (s, 1H), 6.77 (d,1H, J=9.0 Hz), 6.98 (s, 2H), 7.21~7.81 (m, 11H), 8.31 (d, 1H, J=9.0 Hz).
MS (m/z): 523 (MH$^+$), 521 (MH$^-$).
Compound #112 (Reacted with 3-thienyl Boronic Acid)
$^1$H NMR 300 MHz (CD$_3$OD) δ 5.22 (d, 1H, J=11.5 Hz), 5.43 (d, 1H, J=11.5 Hz), 5.88 (s, 2H), 6.38 (s, 1H), 6.72~8.38 (m, 12H).
MS (m/z): 483 (MH$^+$), 481 (MH$^-$).
Compound #116 (Reacted with 4-methylphenyl Boronic Acid)
$^1$H NMR 300 MHz (CD$_3$OD) δ 2.25 (s, 3H), 5.21 (d, 1H, J=11.5 Hz), 5.42 (d, 1H, J=11.5 Hz), 5.80 (s, 2H), 6.38 (s, 1H), 6.74~8.31 (m, 13H).
MS (m/z): 491 (MH$^+$), 489(MH$^-$).
Compound #113 (Reacted with 2-nitrophenyl Boronic Acid)
$^1$H NMR 300 MHz (CD$_3$OD) δ 5.25 (d, 1H, J=11.5 Hz), 5.42 (d, 1H, J=11.5 Hz), 5.88 (s, 2H), 6.39 (s, 1H), 6.68~8.66 (m, 13H).
MS (m/z): 522 (MH$^+$), 520 (MH$^-$).
Compound #117 (Reacted with 2-thienyl Boronic Acid)
$^1$H NMR 300 MHz (CD$_3$OD) δ 5.19~5.42 (m, 2H), 5.93 (s, 2H), 6.40 (s, 1H), 6.74~8.35 (m, 11H).
MS (m/z): 467 (MH$^+$), 465 (MH$^-$).
Compound #118 (Reacted with 3,4-methylenedioxyphenyl Boronic Acid)
$^1$H NMR 300 MHz (CD$_3$OD) δ 5.19~5.42 (m, 2H), 5.93 (m, 4H), 6.38 (s, 1H), 6.74~8.31 (m, 12H).
MS (m/z): 521 (MH$^+$), 519 (MH$^-$).
Compound #119 (Reacted with 4-cyanophenyl Boronic Acid)
$^1$H NMR 300 MHz (CD$_3$OD) δ 5.21~5.42 (m, 2H), 5.70 (m, 2H), 6.18 (s, 1H), 6.60~8.51 (m, 13H).
MS (m/z): 502 (MH$^+$), 500 (MH$^-$).
Compound #120 (Reacted with 4-hydroxymethylphenyl Boronic Acid)
$^1$H NMR 300 MHz (CD$_3$OD) δ 4.79 (s, 2H), 5.25 (d, 1H, J=11.5 Hz), 5.52 (d, 1H, J=11.5 Hz), 5.89 (s, 2H), 6.48 (s, 1H), 6.70~8.31 (m, 13H).
MS (m/z): 507 (MH$^+$), 505 (MH$^-$).
Compound #121 (Reacted with 3-hydroxymethylphenyl Boronic Acid)
$^1$H NMR 300 MHz (CD$_3$OD) δ 4.79 (s, 2H), 5.21 (d, 1H, J=11.5 Hz), 5.48 (d, 1H, J=11.5 Hz), 5.89 (s, 2H), 6.31 (s, 1H), 6.62~8.31 (m, 13H).
MS (m/z): 507 (MH$^+$), 505 (MH$^-$).
Compound #122 (Reacted with 4-dimethylaminophenyl Boronic Acid)
$^1$H NMR 300 MHz (CD$_3$OD) δ 5.21~5.50 (d, 1H, J=11.5 Hz), 5.90 (s, 2H), 6.40 (d, 1H), 6.64~8.31 (m, 13H).
MS (m/z): 520 (MH$^+$), 518 (MH$^-$).

EXAMPLE 80

3-(2,3-Dihydro-benzofuran-5-yl)-2-pyrimidin-2-yl-1,2,3,4-tetrahydro-pyrrolo[3,4-b]quinolin-9-one (#123)

3-(2,3-Dihydro-benzofuran-5-yl)-1,2,3,4-tetrahydro-pyrrolo[3,4-b]quinolin-9-one.HCl salt (0.15 g, 0.440 mmol) was stirred with chloropyrimidine (60.5 mg, 0.528 mmol), KF (31 mg, 0.528 mmol) and DIEA (0.19 mL, 1.1 mmol) at 60° C. for 16 h. The reaction mixture was diluted with H$_2$O (20 mL). The solid was filtered and dried on a suction funnel under vacuum. After silica gel preparative TLC, the title product was isolated as a yellow solid.
$^1$H NMR 300 MHz (CDCl$_3$) δ 3.10 (t, 2H, J=8.8 Hz), 4.52 (t, 2H, J=8.8 Hz), 4.92 (m, 2H), 6.15~8.45 (m, 10H), 9.81 (br, s, 1H).
MS (m/z) 383(MH$^+$), 381 (MH$^-$).

EXAMPLE 81

3-Benzofuran-5-yl-2-(5-pyridin-2-yl-pyrimidin-2-yl)-1,2,3,4-tetrahydro-pyrrolo[3,4-b]quinolin-9-one (#126)

A: Benzofuran-5-carbaldehyde was prepared according to the process described by Hiroya, K.; Hashimura, K.; Ogasawara, K. in *Heterocycles*, 1994, Vol. 38, No. 11, 2463–72

B: 1-Benzofuran-5-yl-2,3,4,9-tetrahydro-1H-β-carboline was prepared according to the process outlined in Example 12,
$^1$H NMR 300 MHz (CDCl$_3$) δ 2.68~2.95 (m, 2H), 3.10 (m, 1H), 3.28 (m, 1H), 5.25 (s, 1H), 6.65 (s, 1H), 7.15 (m, 3H), 7.38 (m, 2H), 7.51 (m, 1H), 7.58 (s, 1H), 8.22 (s, 1H).
MS (m/z) MH$^+$ (289), MH$^-$ (287).

C: 1-Benzofuran-5-yl-2-(5-pyridin-2-yl-pyrimidin-2-yl)-2,3,4,9-tetrahydro-1H-β-carboline was prepared according to the process outlined in Example 12.
$^1$H NMR 300 MHz (CDCl$_3$) δ 3.00 (m, 2H), 3.40 (m, 1H), 5.11 (m, 1H), 6.65 (s, 1H), 7.15~8.00 (m, 12H), 8.61 (m, 1H), 8.91 (m, 1H), 8.22 (s, 2H).
MS (m/z) MH$^+$ (444), MH$^-$ (442).

D: 1-(5-benzofuryl)2,34,9-tetrahydro-2-[5-(2-pyridinyl)-2-pyrimidinyl]-1H-β-carboline (30 mg, 0.06764 mmol) and KOtBu (12.9 mg, 0.115 mmol) were stirred in DMF (1 mL) under O$_2$ gas for 10 hours at room temperature. Preparative TLC (5% methanol in CH$_2$Cl$_2$) yielded the title product as yellow solid.
$^1$H NMR 300 MHz (CD$_3$OD) δ 5.15 (m, 2H), 6.55 (s, 1H), 6.82~8.98 (m, 15H).
MS (m/z) 458, (MH$^+$), 456 (MH$^-$).

EXAMPLE 82

3-(2,3-Dihydro-benzofuran-5-yl)-2-[5-(1-oxy-pyridin-2-yl)-pyrimidin-2-yl]-1,2,3,4-tetrahydro-pyrrolo[3,4-b]quinolin-9-one (#125)

3-(2,3-dihydro-5-benzofuranyl)-1,2,3,4-tetrahydro-2-[5-(2-pyridinyl)-2-pyrimidinyl]-(3R)-9H-pyrrolo[3,4-b]quinolin-9-one (4.5 mg, 0.010 mmol) and mCPBA (1.73 mg, 0.010 mmol) were stirred in THF (2 mL). A few drops of DMF were added to make the solution clear. The reaction mixture was stirred at room temperature for 80 hours and then at 60° C. for 8 hours. Preparative TLC (10% MeOH in CH$_2$Cl$_2$) yielded the title product as off-white solid, with some recovered starting material.
$^1$H NMR 300 MHz (CD$_3$OD) δ 3.12 (t, 2H, J=8.8 Hz), 4.45 (t, 2H, J=8.8 Hz), 6.35 (s, 1H), 6.55 (d, 1H), 7.21~8.99 (m, 11H).
MS (m/z) 458, (MH$^+$), 456 (MH$^-$).

EXAMPLE 83 THROUGH 86

1-(2,3-Dihydro-benzofuran-5-yl)-2-[5-(2,3-dimethyl-3H-imidazol-4-yl)-pyrimidin-2-yl]-2,3,4,9-tetrahydro-1H-β-carboline 2-(5-bromo-2-pyrimidinyl)-1-(2,3-dihydro-5-benzofuranyl)-2,3,4,9-tetrahydro-1H-β-carboline (0.45 g, 1.00 mmol), 1,2-dimethyl-1H-imidazole (0.18 g, 1.87 mmol), Pd(OAc)$_2$ (12 mg, 0.05 mmol), PPh$_3$ (26 mg, 0.1 mmol) and K$_2$CO$_3$ (0.28 g, 2 mmol) were stirred in 3.5 mL DMF at 140° C. for 14 hours. The mixture was poured into aqueous 10% NaOH solution (50 mL). The resulting solution was extracted with CH$_2$Cl$_2$ (3×50 mL) and dried over Na$_2$SO$_4$. Purification by preparative TLC yielded the title product as yellow powder.

$^1$H NMR 300 MHz (CDCl$_3$) δ 2.21 (s, 3H), 2.35 (s, 3H), 2.90 (m, 2H), 3.10 (t, 2H, J=8.8 Hz), 3.35 (m, 1H), 4.52 (t, 2H, J=8.8 Hz), 4.91 (m, 1H), 6.68~7.61 (m, 10H).

MS (m/z) 463 (MH$^+$), 461 (MH$^-$).

The following compounds were similarly prepared according to the procedure described above with appropriate selection and substitution of suitably substituted reagents.

2-[5-(3-Benzyl-2-methyl-3H-imidazol-4-yl)-pyrimidin-2-yl]-1-(2,3-dihydro-benzofuran-5-yl)-2,3,4,9-tetrahydro-1H-β-carboline MS (m/z) 539, (MH$^+$), 537 (MH$^-$).

3-(2,3-Dihydro-benzofuran-5-yl)-2-[5-(2,3-dimethyl-3H-imidazol-4-yl)-pyrimidin-2-yl]-1,2,3,4-tetrahydro-pyrrolo[3,4-β]quinolin-9-one (#128)

$^1$H NMR 300 MHz (CD$_3$OD) δ 3.08 (t, 2H, J=9.5 Hz), 3.28 (s, 3H), 3.50 (s, 3H), 4.42 (t, 2H, J=9.5 Hz), 5.02 (br, s, 2H), 6.24 (s, 1H), 6.63 (m, 1H), 6.84 (s, 1H), 7.19 (m, 2H), 7.31 (m, 1H), 7.53 (s, 2H), 8.35 (m, 3H).

MS (m/z) 477, (MH$^+$), 475 (MH$^-$).

2-[5-(3-Benzyl-2-methyl-3H-imidazol-4-yl)-pyrimidin-2-yl]-3-(2,3-dihydro-benzofuran-5-yl)-1,2,3,4-tetrahydro-pyrrolo[3,4-b]quinolin-9-one (#127)

$^1$H NMR 300 MHz (CD$_3$OD) δ 1.90 (s, 3H), 2.21 (s, 2H), 3.12 (t, 2H, J=8.8 Hz), 4.48 (t, 2H, J=8.8 Hz), 5.12 (m, 2H), 6.15 (s, 1H), 6.61~8.85 (m, 15H).

MS (m/z) MH$^+$ (553), MH$^-$ (551).

EXAMPLE 87

3-(2,3-Dihydro-benzofuran-5-yl)-2-pyridin-2-yl-1,2,3,4-tetrahydro-pyrrolo[3,4-b]quinolin-9-one (#129)

3-(2,3-dihydro-5-benzofuranyl)-1,2,3,4-tetrahydro-9H-pyrrolo[3,4-b]quinolin-9-one HCl (0.30 g, 0.88 mmol) and 2-bromo-pyridine (2 mL), Pd$_2$dba$_3$ (0.23 g, 0.25 mmol), BINAP (0.47 g, 0.75 mmol) and NaOtBu (0.66 g, 6.87 mmol) were stirred in 1,4-dioxane (4 mL) at 90° C. for 1 hour. The resulting mixture was concentrated and then filtered on a plug of Celite with CH$_2$Cl$_2$. Purification by preparative TLC (5% CH$_3$OH/CH$_2$Cl$_2$) yielded the title product as a yellow solid.

$^1$H NMR 300 MHz (CD$_3$OD) δ 2.92 (t, 2H, J=9.5 Hz), 4.40 (t, 2H, J=9.5 Hz), 4.54 (d, 1H, J=22 Hz), 4.85 (d, 1H, J=22 Hz), 6.55 (m, 2H), 7.10 (m, 3H), 7.35 (m, 4H), 8.02 (m, 1H), 8.30 (d, 1H, J=9.3 Hz).

MS (m/z) 382, (MH$^+$), 380 (MH$^-$).

EXAMPLE 88

3-Benzo[1,3]dioxol-5-yl-2-(4-imidazol-1-yl-phenyl)-1,2,3,4-tetrahydro-pyrrolo[3,4-b]quinolin-9-one (#133)

3-(1,3-benzodioxol-5-yl)-1,2,3,4-tetrahydro-9H-pyrrolo[3,4-b]quinolin-9-one (30.6 mg, 0.1 mmol), 1-(4-bromo-phenyl)-1H-imidazole (22.3 mg, 0.1 mmol), Pd$_2$dba$_3$ (4.6 mg, 0.005 mmol), biphenyl-2-yl-di-tert-butyl-phosphane 3.0 mg, 0.01 mmol) and NaOtBu (14 mg, 0.14 mmol) were stirred in 1,4-dioxane (0.6 mL) at 89° C. for 17 hours. Purification by preparative TLC (5% CH$_3$OH/CH$_2$Cl$_2$) yielded the title product as yellow powder.

$^1$H NMR 300 MHz (CD$_3$OD) δ 4.70 (d, 1H), 5.02 (d, 1H), 5.48 (s, 2H), 5.88 (s, 2H), 6.75~8.32 (m, 14H).

MS (m/z) MH$^+$(449), MH$^-$(447).

EXAMPLE 89

2-[2,3']Bipyridinyl-6'-yl-3-(2,3-dihydro-benzofuran-5-yl)-1,2,3,4-tetrahydro-pyrrolo[3,4-b]quinolin-9-one (# 134)

A: 2-(5-Bromo-pyridin-2-yl)-1-(2,3-dihydro-benzofuran-5-yl)-2,3,4,9-tetrahydro-1H-β-carboline 1-(2,3-dihydro-5-benzofuranyl)-2,3,4,9-tetrahydro-1H-β-carboline (11.6 g, 40 mmol), 2,5-dibromopyridine (10.42 g, 44 mmol), Pd$_2$dba$_3$ (1.465 g, 1.6 mmol), dppp (1.32 g, 3.2 mmol) and NaOtBu (5.38 g, 56 mmol) were stirred in 60 mL DMF at 80° C. for 3 days. The reaction mixture was filtered through a plug of Celite with CH$_2$Cl$_2$. The reaction mixture was then concentrated, the crude mixture was then loaded on Foxy column (110 g silica gel) and eluted with ethyl acetate/hexane (3:7). The product crystallized out in test tubes. The product was concentrated and then recrystallized from THF to yield the product as yellow crystals.

$^1$H NMR 400 MHz (THF-d8) δ 0.91 (m, 1H), 1.15 (m, 1H), 1.25 (t, 2H, J=9.5 Hz), 1.60 (m, 1H), 2.31 (m, 1H), 2.60 (t, 2H, J=9.5 Hz), 4.75 (d, 1H, J=7.6H), 5.02 (d, 1H, J=7.6 Hz), 5.10~5.28 (m, 4H), 5.380 (m, 2H), 5.58 (m, 1H), 5.72 (m, 1H), 6.28 (s, 1H), 8.12 (s, 1H).

MS (m/z) 446, 448 (MH$^+$), 444, 446 (MH$^-$).

B: 2-[2,3']Bipyridinyl-6'-yl-1-(2,3-dihydro-benzofuran-5-yl)-2,3,4,9-tetrahydro-1H-β-carboline The product from step A above (0.4 g, 0.896 mmol), 2-tributylstannanyl-pyridine (0.8 g, 2.17 mmol) and Pd(PPh$_3$)$_4$ (0.12 g, 0.104 mmol) were stirred in 1,4-dioxane (5 mL) at 88° C. for 24 h. The reaction mixture was filtered through a plug of Celite with CH$_2$Cl$_2$ and then concentrated to a small volume. Preparative TLC (3:7 ethyl acetate/heaxne; then 5% CH$_3$OH/CH$_2$Cl$_2$) yielded the product as a yellow solid.

$^1$H NMR (CDCl$_3$) δ 2.82 (m, 1H), 3.10 (m, 3H), 3.58 (m, 1H), 4.31 (m, 1H), 4.53 (t, 2H, J=9.5 z), 6.71 (, d, 1H, J=7.6 Hz), 6.85 (d, 1H, J=7.6 Hz).

MS (m/z) 445, (MH$^+$), 443 (MH$^-$).

C: 2-[2,3']Bipyridinyl-6'-yl-3-(2,3-dihydro-benzofuran-5-yl)-1,2,3,4-tetrahydro-pyrrolo[3,4-b]quinolin-9-one (#134)

Following the procedure describe in Example 19 with appropriate selection and substitution of reagents, yielded the title product as a solid.

$^1$H NMR 300 MHz (CDCl$_3$) δ 3.16 (t, 2H, J=9.5 Hz), 4.43 (t, 2H, J=9.5 Hz), 4.98~5.20 (m, 2H), 6.12 (s, 1H), 6.60~8.70 (15H).

MS (m/z) 459 (MH$^+$), 457 (MH$^-$).

EXAMPLE 90

3-(2,3-Dihydro-benzofuran-5-yl)-2-[5-(3-methyl-3H-imidazol-4-yl)-pyridin-2-yl]-1,2,3,4-tetrahydro-pyrrolo[3,4-b]quinolin-9-one (#137)

A: 2-Chloro-5-(3-methyl-3H-imidazol-4-yl)-pyridine

2-Chloro-4-iodo-pyridine (0.239 g, 1 mmol), 1-methyl-1H-imidazole (0.41 g, 5 mmol), Pd(OAc)$_2$ (22.5 mg, 0.1 mmol), PPh$_3$ (53 mg, 0.2 mmol) and Cs$_2$CO$_3$ (0.326 g, 1 mmol) were stirred in DMF (3 mL) at 120° C., for 6 hours. Purification by preparative TLC yielded the product as an oil containing 1-methyl-1H-imidazole. The product was used for the next step without further purification.

$^1$H NMR (CDCl3) δ 3.68 (s, 3H), 7.19 (s, 1H), 7.27 (s, 1H), 7.56 (s, 1H), 7.68 (dd, 1H), 8.45 (d, 1H).

MS (m/z) MH$^+$ (194).

B: 3-(2,3-Dihydro-benzofuran-5-yl)-2-[5-(3-methyl-3H-imidazol-4-yl)-pyridin-2-yl]-1,2,3,4-tetrahydro-pyrrolo[3,4-b]quinolin-9-one (#137)

3-(2,3-dihydro-benzofuran-5-yl)-1,2,3,4-tetrahydro-pyrrolo[3,4-b]quinolin-9-one (0.127 g, 0.372 mmol), 2-chloro-5-(3-methyl-3H-imidazol-4-yl)-pyridine (0.06 g, 0.31 mmol), Pd(OAc)$_2$ (3.5 mg, 0.0155 mmol), biphenyl-2-yl-dicyclohexyl-phosphane (5.43 mg, 0.0155 mmol) and NaOtBu (0.104 g, 1.085 mmol) were stirred in 1,4-dioxane (0.6 mL) at 90° C. Purification by preparative TLC (5% MeOH in CH$_2$Cl$_2$) yielded the product as yellow solid.

$^1$H NMR 300 MHz (CDCl$_3$) δ 3.12 (t, 2H), 3.60 (s, 3H), 3.50 (t, 2H), 5.12 (m, 2H), 6.08 (s, 1H), 6.70 (m, 2H), 7.20~8.55 (m, 10H).

MS (m/z) MH$^+$ (462), MH$^-$ (460).

EXAMPLE 91

2-[5-(3-Benzyl-3H-imidazol-4-yl)-pyridin-2-yl]-3-(2,3-dihydro-benzofuran-5-yl)-1,2,3,4-tetrahydro-pyrrolo[3,4-b]quinolin-9-one (#138)

A: 5-(3-Benzyl-3H-imidazol-4-yl)-2-chloro-pyridine

Following the procedure described in Example 90, Step A, with appropriate selection and substitution of reagents, yielded the product as a solid.

$^1$H NMR (CDCl$_3$) δ 5.15 (s, 2H), 6.86~8.30 (m, 10H).

MS (m/z) MH$^+$ (270).

B: Following the procedure described in Example 90 Step B, with appropriate selection and substitution of reagents, yield the product as a solid.

$^1$H NMR 300 MHz (CD$_3$OD) δ 3.12 (t, 2H), 3.60 (m, 2H), 4.55 (t, 2H), 5.10 (m, 2H), 6.05 (s, 1H), 6.45~8.54 (m, 12H).

MS (m/z) MH$^+$ (538), MH$^-$ (536).

EXAMPLE 92

3-(2,3-Dihydro-benzofuran-5-yl)-2-pyridin-2-yl-1,2,3,4-tetrahydro-pyrrolo[3,4-b]quinolin-9-one (#136)

3-(2,3-dihydro-5-benzofuranyl)-1,2,3,4-tetrahydro-(3R)-9H-pyrrolo[3,4-b]quinolin-9-one HCl (0.0341 g, 0.1 mmol), 2-iodo-pyridine (0.0341 g, 0.2 mmol), Pd$_2$ dba$_3$ (22.9 mg, 0.025 mmol), BINAP (46.7 mg, 0.075 mmol) and NaOtBu (58 mg, 0.6 mmol) were stirred in 1,4-dioxane (0.8 mL) at 50° C. for 3 hours. Purification by preparative TLC (5% methanol/CH$_2$Cl$_2$) yielded the product as a yellow solid.

$^1$H NMR 300 MHz (CD$_3$OD) δ 2.92 (t, 2H, J=9.5 Hz), 4.40 (t, 2H, J=9.5 Hz), 4.54 (d, 1H, J=22 Hz), 4.85 (d, 1H, J=22 Hz), 6.55 (m, 2H), 7.10 (m, 3H), 7.35 (m, 4H), 8.02 (m, 1H), 8.30 (d, 1H, J=9.3 Hz).

MS (m/z) MH$^+$ (382), MH$^-$ (380).

HPLC trace: Chiral OD, methanol, 25° C., tr=5.201 min.

EXAMPLE 93

3-(2,3-dihydro-benzofurn-5-yl)-2-[5-(3H-imidazol-4-yl)-pyridin-2-yl]-1,2,3,4-tetrahydro-pyrrolo[3,4-b]quinolin-9-one A stirred solution of 2-[5-(3-Benzyl-3H-imidazol-4-yl)-pyridin-2-yl]-3-(2,3-dihydro-benzofuran-5-yl)-1,2,3,4-tetrahydro-pyrrolo[3,4-b]quinolin-9-one (0.005 mmol, 1 equivalent), prepared as in Example 91, and p-toluenesulfonyl hydrazide (0.25 mmol, 50 equivalents) in CH$_3$OH (3 mL) at about 80° C. is added to a solution of sodium acetate (0.5 mmol, 100 equiv.) in H$_2$O (2 mL) over about a 2 h period. The mixture is stirred for about another 3 h at about 80° C., then cooled to about 25° C., and the solvent evaporated. The residue is dissolved into CH$_2$Cl$_2$ (20 mL), washed with saturated aqueous NaCl (10 mL), dried (Na$_2$SO$_4$), and concentrated to yield the title product.

EXAMPLE 94

3-(2,3-Dihydro-benzofuran-5-yl)-2-[5-(2-methyl-3H-imidazol-4-yl)-pyrimidin-2-yl]-1,2,3,4-tetrahydro-pyrrolo[3,4-b]quinolin-9-one Following the procedure described in Example 93, 2-[5-(3-benzyl-2-methyl-3H-imidazol-4-yl)-pyrimidin-2-yl]-3-(2,3-dihydro-benzofuran-5-yl)-1,2,3,4-tetrahydro-pyrrolo[3,4-b]quinolin-9-one, prepared as in Example 86, is reacted to yield the title compound.

EXAMPLE 95

In Vitro Testing

Cyclic Nucleotide Phosphodiesterase (PDE) Assay
PDEV Isolation

PDEV was isolated from rabbit and human tissues according to the protocol described by Boolell et al. (Boolell, M., Allen, M. J., Ballard, S. A., Ge[o-Attee, S., Muirhead, G. J., Naylor, A. M., Osterloh, I. H., and Gingell, C) in *International Journal of Impotence Research* 1996 8, 47–52 with minor modifications.

Briefly, rabbit or human tissues were homogenized in an ice-cold buffer solution containing 20 mM HEPES (pH 7.2), 0.25M sucrose, 1 mM EDTA, and 1 mM phenylmethylsulphonyl fluoride (PMSF). The homogenates were centrifuged at 100,000 g for 60 minutes at 4° C. The supernatant was filtered through 0.2 μM filter and loaded on a Pharmacia Mono Q anion exchange column (1 ml bed volume) that was equilibrated with 20 mM HEPES, 1 mM EDTA and 0.5 mM PMSF. After washing out unbound proteins, the enzymes were eluted with a linear gradient of 100–600 mM NaCl in the same buffer (35 to 50 ml total, depending on the tissue. Enzymes from the skeletal muscle, corpus cavernosum, retina, heart and platelet were eluted with 35, 40, 45, 50, and 50 ml respectively.) The column was run at a flow rate of 1 ml/min and 1 ml fractions were collected. The fractions comprising various PDE activities were pooled separately and used in later studies.

Measurement of Inhibition of PDEV

The PDE assay was carried out as described by Thompson and Appleman in *Biochemistry* 1971 10, 311–316 with minor modifications, as noted below.

The assays were adapted to a 96-well format. The enzyme was assayed in 5 mM MgCl$_2$, 15 mM Tris HCl (pH 7.4), 0.5 mg/ml bovine serum albumin, 1 μM cGMP or cAMP, 0.1 μCi [$^3$H]-cGMP or [$^3$H]-cAMP, and 2–10 μl of column elution. The total volume of the assay was 100 μl. The reaction mixture was incubated at 30° C. for 30 minutes. The reaction was stopped by boiling for 1 minute and then cooled down on ice. The resulting [$^3$H]5'-mononucleotides were further converted to uncharged [$^3$H]-nucleosides by adding 25 μl 1 mg/ml snake venom (*Ophiophagus hannah*) and incubating at 30° C. for 10 minute. The reaction was stopped by the addition of 1 ml Bio-Rad AG1-X2 resin slurry (1:3).

All the charged nucleotides were bound by the resin and only uncharged [³H]-nucleosides remained in the supernatant after centrifuging. An aliquot of 200 μl was taken and counted by liquid scintillation. PDE activity was expressed as pmol cyclic nucleotide hydrolyzed/min/ml of enzyme preparation.

Inhibitor studies were carried out in assay buffer with a final concentration of 10% DMSO. Under these conditions, the hydrolysis of product increased with time and enzyme concentration in a linear fashion.

EXAMPLE 96

In Vitro Determination of $K_i$ for Phosphodiesterase Inhibitors

The assays were adapted to a 96-well format. Phosphodiesterase was assayed in 5 mM $MgCl_2$, 15 mM Tris HCl (pH 7.4), 0.5 mg/ml bovine serum albumin, 30 nM ³H-cGMP and test compound at various concentrations. The amount of enzyme used for each reaction was such that less than 15% of the initial substrate was converted during the assay period. For all measurements, the test compound was dissolved and diluted in 100% DMSO (2% DMSO in assay). The total volume of the assay was 100 μl. The reaction mixture was incubated at 30° C. for 90 minutes. The reaction was stopped by boiling for 1 minute and then immediately cooled by transfer to an ice bath. To each well was then added 25 μl 1 mg/ml snake venom (*Ophiophagus hannah*) and the reaction mixture incubating at 30° C. for 10 minute. The reaction was stopped by the addition of 1 ml Bio-Rad AG1-X2 resin slurry (1:3). An aliquot of 200 μl was taken and counted by liquid scintillation.

The % inhibition of the maximum substrate conversion (by the enzyme in the absence of inhibitor) was calculated for each test compound concentration. Using GraphPad Prism's nonlinear regression analysis (sigmoidal dose response), the % inhibition vs log of the test compound concentration was plotted to determine the $IC_{50}$. Under conditions where substrate concentration <<$K_m$ of the enzyme ($K_m$=substrate concentration at which half of the maximal velocity of the enzyme is achieved), $K_i$ is equivalent to the $IC_{50}$ value.

Following procedures as described herein, the compounds as listed in Tables 1–6 were prepared. PDEV inhibitory activities for these compounds are presented either as the $IC_{50}$ (μM), as a percent inhibition at a given concentration of test compound or as a Ki value in the Tables below. Unless otherwise noted, PDEV inhibitory activities were measured using human tissue. The abbreviation "stereo" refers to the stereogenic configuration, the abbreviation "Rac" shall denote a racemic mixture.

TABLE 1

| ID # | $R^2$ | Stereo | $IC_{50}$ (nM) |
|---|---|---|---|
| 4 | 3,4-methylenedioxyphenyl | Rac | 664 |
| 12 | 3,4-dimethoxyphenyl | Rac | 549[a] |
| 17 | 5-(2,3-dihydrobenzofuryl) | Rac | 65% Inh @ 10 μM |
| 48 | 3,4-methylenedioxyphenyl | R | |

TABLE 2

| ID # | $R^2$ | Stereo | $IC_{50}$ (nM) |
|---|---|---|---|
| 3 | 3,4-methylenedioxyphenyl | Rac | 340[a] |

TABLE 3

| ID # | $R^2$ | Stereo | C | $R^4$ | $IC_{50}$ (nM) |
|---|---|---|---|---|---|
| 1 | 3,4-methylene dioxyphenyl | Rac | 2-pyrimidinyl | 5-(3,4-dimethoxy phenyl) | 0.165 |

TABLE 3-continued

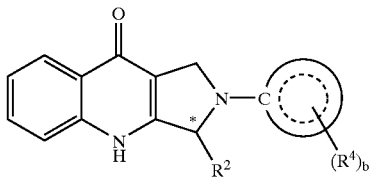

| ID # | R² | Stereo | C | R⁴ | IC₅₀ (nM) |
|---|---|---|---|---|---|
| 2 | 3,4-methylene dioxyphenyl | Rac | 2-pyrimidinyl | 5-(4-methoxy phenyl) | 0.191 |
| 7 | 3,4-methylene dioxyphenyl | Rac | 2-pyrimidinyl | 5-(4-methyl phenyl) | 0.325 |
| 11 | 3,4-methylene dioxyphenyl | Rac | 2-pyrimidinyl | absent | 3.73 |
| 35 | 3,4-methylene dioxyphenyl | S | 2-pyrimidinyl | 5-(3,4-dimethoxy phenyl) | 1.42[a] |
| 36 | 3,4-methylene dioxyphenyl | R | 2-pyrimidinyl | 5-(3,4-dimethoxy phenyl) | 0.075 |
| 55 | 3,4-methylene dioxyphenyl | Rac | 2-pyrimidinyl | 5-bromo | 4.48 |
| 56 | 3,4-methylene dioxyphenyl | Rac | 2-pyrimidinyl | 5-(3-pyridinyl) | 1.24 |
| 57 | 3,4-methylene dioxyphenyl | Rac | 2-pyrimidinyl | 5-(4-pyridinyl) | 0.84 |
| 15 | 3,4-dimethoxy phenyl | Rac | 2-pyrimidinyl | 5-(3,4-dimethoxy phenyl) | 1156 |
| 39 | 5-(2,3-dihydro-benzofuryl) | Rac | 2-pyrimidinyl | 5-(4-methoxy phenyl) | 0.47 |
| 66 | 5-(2,3-dihydro-benzofuryl) | R | 2-pyrimidinyl | 5-(4-methoxy phenyl) | 0.19 |
| 42 | 5-(2,3-dihydro-benzofuryl) | Rac | 2-pyrimidinyl | 5-(4-hydroxy phenyl) | 1.06 |
| 51 | 5-(2,3-dihydro-benzofuryl) | Rac | 2-pyrimidinyl | 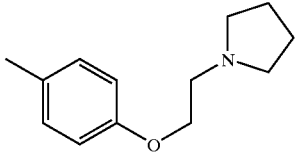 | 1.70[a] |
| 52 | 5-(2,3-dihydro-benzofuryl) | Rac | 2-pyrimidinyl | 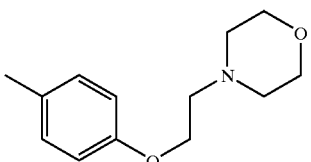 | 0.40[a] |
| 61 | 5-(2,3-dihydro-benzofuryl) | Rac | 2-pyrimidinyl | 5-(2-pyridinyl) | 1.03 |
| 65 | 5-(2,3-dihydro-benzofuryl) | R | 2-pyrimidinyl | 5-(2-pyridinyl) | 0.23 |
| 70 | 5-(2,3-dihydro-benzofuryl) | Rac | 2-pyrimidynyl | 5-(3-pyridinyl) | 2.10 |
| 73 | 5-(2,3-dihydro-benzofuryl) | R | 2-pyrimidynyl | 5-(4-methoxy phenyl) | 0.170 |
| 74 | 5-(2,3-dihydro-benzofuryl) | Rac | 2-pyrimidynyl | 5-bromo | 1.90 |
| 76 | 5-(2,3-dihydro-benzofuryl) | R | 2-pyrimidynyl | 5-(2-pyridinyl) | 0.230 |
| 81 | 5-(2,3-dihydro-benzofuryl) | R | 2-pyrimidynyl | 5-(3,4-dimethoxy phenyl) | 0.230 |
| 84 | 5-(2,3-dihydro-benzofuryl) | S | 2-pyrimidynyl | 5-(4-methoxy phenyl) | 2.42 |

TABLE 3-continued

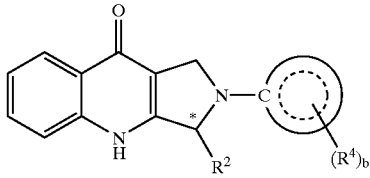

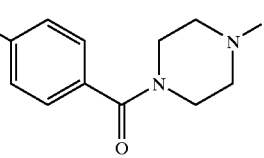

| ID # | R² | Stereo | C | R⁴ | IC₅₀ (nM) |
|---|---|---|---|---|---|
| 85 | 3,4-methylene dixoyphenyl | Rac | 2-pyrimidynyl | (structure: 4-(4-methylpiperazin-1-ylcarbonyl)phenyl) | 0.90 |
| 91 | 3,4-methylene dixoyphenyl | Rac | 2-thiazolyl | 3-(4-methoxy phenyl) | 0.410 |
| 96 | 3,4-dihydrobenzo-[1,4]-dioxin-6-yl | Rac | 2-pyrimidynyl | 5-(4-methoxy phenyl) | 0.520 |
| 99 | 3,4-methylene dixoyphenyl | Rac | 2-pyrimidynyl | 5-(4-pyridinyl) | 0.840 |
| 100 | 3,4-methylene dixoyphenyl | Rac | 2-pyrimidynyl | 5-(3-pyridinyl) | 0.520 |
| 114 | 5-indanyl | Rac | 2-pyrimidynyl | 5-(3,4,-methylene dioxyphenyl) | 1.14 |
| 123 | 5-(2,3-dihydro benzofuryl) | Rac | 2-pyrimidynyl | absent | 12.8 |
| 124 | 3-thienyl | Rac | 2-pyrimidynyl | 5-(3,4-dimethoxy phenyl) | 4.132 |
| 125 | 5-(2,3-dihydro benzofuryl) | Rac | 2-pyrimidynyl | N-oxo-2-pyridinyl | Ki = 0.144 |
| 126 | 5-benzofuryl | Rac | 2-pyrimidynyl | 5-(2-pyridinyl) | Ki = 0.138 |
| 127 | 5-(2,3-dihydro benzofuryl) | Rac | 2-pyrimidynyl | 5-(1-benzyl-2-methyl-imidazolyl) | Ki = 0.140 |
| 128 | 5-(2,3-dihydro benzofuryl) | Rac | 2-pyrimidynyl | 5-(1,2-dimethyl imidazolyl) | Ki = 0.300 |
| 129 | 5-(2,3-dihydro benzofuryl) | Rac | 2-pyridinyl | absent | Ki = 0.650 |
| 130 | 5-(2,3-dihydro benzofuryl) | Rac | 2-pyrimidynyl | 5-bromo | 1.9 |
| 131 | 5-(2,3-dihydro benzofuryl) | Rac | 2-pyridinyl | 5-bromo | Ki = 1.55 |
| 132 | 3,4-methylene dioxyphenyl | Rac | 2-pyridinyl | absent | |
| 133 | 3,4-methylene dioxyphenyl | Rac | phenyl | 4-(1-imidazolyl) | Ki = 1.75 |
| 134 | 5-(2,3-dihydro benzofuryl) | Rac | 2-pyridinyl | 5-(2-pyridinyl) | Ki = 1.10 |
| 136 | 5-(2,3-dihydro benzofuryl) | R | 2-pyridinyl | absent | Ki = 0.18 |
| 137 | 5-(2,3-dihydro benzofuryl) | Rac | 2-pyridinyl | 5-(5-(1-methyl)-imidazolyl) | |
| 138 | 5-(2,3-dihydro benzofuryl) | Rac | 2-pyridinyl | 5-(5-(1-benzyl)-imidazolyl) | |

TABLE 4

| ID # | R² | Stereo | Y | C | R⁴ | IC₅₀ (nM) |
|---|---|---|---|---|---|---|
| 5 | 3,4-methylene dioxyphenyl | Rac | CH₂ | 4-pyridinyl | absent | 688 |
| 6 | 3,4-methylene dioxyphenyl | Rac | C(O)CH=CH | phenyl | 4-methoxy carbonyl | 0.507 |
| 8 | 3,4-methylene dioxyphenyl | Rac | C(O)—CH=CH | phenyl | 4-carboxy | 0.828 |
| 9 | 3,4-methylene dioxyphenyl | Rac | C(O) | 2-benzo(b)furyl | 6-hydroxy | 0.460 |
| 13 | 3,4-methylene dioxyphenyl | Rac | C(O) | 2-furyl | 5-(3-tri fluoromethyl phenyl) | 0.227 |
| 16 | 3,4-methylene dioxyphenyl | Rac | C(O) | 2-furyl | 5-(4-nitro phenyl) | 0.390 |
| 18 | 3,4-methylene dioxyphenyl | Rac | C(S) | 1-imidazolyl | absent | 54% Inh @ 10 μM |
| 19 | 3,4-methylene dioxyphenyl | Rac | CH₂ | phenyl | absent | 234 |
| 21 | 3,4-methylene dioxyphenyl | Rac | C(O) | 2-furyl | 5-(4-methoxy phenyl) | 1.93 |
| 22 | 3,4-methylene dioxyphenyl | Rac | C(O) | 2-furyl | 5-(4-hydroxy phenyl) | 0.86 |
| 23 | 3,4-methylene dioxyphenyl | Rac | C(O) | 2-furyl | 5-(4-formyl phenyl) | 1.76 |
| 24 | 3,4-methylene dioxyphenyl | Rac | C(O) | 2-furyl | 5-(4-methoxy carbonyl phenyl) | 1.21 |
| 25 | 3,4-methylene dioxyphenyl | Rac | C(O) | 3-pyridinyl | 2-hydroxy | 1.57 |
| 26 | 3,4-methylene dioxyphenyl | Rac | C(O) | 2-furyl | 5-(4-amino phenyl) | 1.92 |
| 27 | 3,4-methylene dioxyphenyl | Rac | C(O)—O—CH₂ | phenyl | absent | 3.40[a] |
| 28 | 3,4-methylene dioxyphenyl | S | CH₂ | phenyl | absent | 6881[a] |
| 29 | 3,4-methylene dioxyphenyl | Rac | C(O) | 2-furyl | 5-(4-carboxy phenyl) | 1.05 |
| 30 | 3,4-methylene dioxyphenyl | Rac | C(O) | 2-furyl | 5-bromo | 5.20[a] |
| 31 | 3,4-methylene dioxyphenyl | Rac | C(O)—CH₂—CH₂ | phenyl | 4-methoxy carbonyl | 11.20 |

TABLE 4-continued

| ID # | R² | Stereo | Y | C (ring) | R⁴ | IC₅₀ (nM) |
|---|---|---|---|---|---|---|
| 32 | 3,4-methylene dioxyphenyl | Rac | C(O) | 2-benzo(b)furyl | (methoxyethyl diethylamine structure) | 3.40 |
| 33 | 3,4-methylene dioxyphenyl | Rac | C(O)—CH₂—CH₂ | phenyl | 4-carboxy | 3.40 |
| 34 | 3,4-methylene dioxyphenyl | Rac | C(O)—CH₂—CH₂ | phenyl | (acetyl-4-methylpiperazine structure) | 59.50[a] |
| 37 | 3,4-methylene dioxyphenyl | Rac | C(O)O—CH₂ | 4-pyridinyl | absent | 5.72 |
| 44 | 3,4-methylene dioxyphenyl | Rac | C(O) | 2-furyl | (4-methylpiperazinyl-carbonyl-tolyl structure) | 1.58 |
| 69 | 3,4-methylene dioxyphenyl | R | C(O) | 2-furyl | (4-methylpiperazinyl-carbonyl-tolyl structure) | 0.32 |
| 45 | 3,4-methylene dioxyphenyl | Rac | C(O) | 2-furyl | (pyrrolidinylethoxy-tolyl structure) | 1.33 |
| 47 | 3,4-methylene dioxyphenyl | R | CH₂ | phenyl | absent | — |
| 49 | 3,4-methylene dioxyphenyl | Rac | C(O) | 2-benzo(b)furyl | (methoxyethyl morpholine structure) | 1.127[a] |
| 50 | 3,4-methylene dioxyphenyl | R | C(O) | 2-furyl | 5-(3-trifluoromethyl phenyl) | 0.61[a] |
| 54 | 3,4-methylene dioxyphenyl | Rac | CH₂ | phenyl | absent | 234 |

TABLE 4-continued

| ID # | R² | Stereo | Y | C | R⁴ | IC₅₀ (nM) |
|---|---|---|---|---|---|---|
| 58 | 3,4-methylene dioxyphenyl | Rac | C(O) | 2-furyl | 5-(4-hydroxy phenyl) | 0.86 |
| 59 | 3,4-methylene dioxyphenyl | Rac | C(O) | 2-furyl | 5-(3-tri fluoromethyl phenyl) | 0.66 |
| 20 | 5-(2,3-dihydro-benzofuryl) | Rac | C(O)—CH=CH | phenyl | 4-methoxy carbonyl | 0.530 |
| 53 | 5-(2,3-dihydro-benzofuryl) | Rac | C(O)O—CH₂ | 4-pyridinyl | absent | 5.340[a] |
| 60 | 5-(2,3-dihydro-benzofuryl) | Rac | CH₂ | phenyl | absent |  |
| 75 | 3,4-methylene dioxyphenyl | Rac | C(O) | phenyl | absent | 51.51 |
| 77 | 5-(2,3-dihydro-benzofuryl) | R | CH₂ | phenyl | absent | 62.67 |
| 79 | 3,4-methylene dioxyphenyl | R | C(O)O—CH₂ | 4-pyridinyl | absent | 34.78 |
| 80 | 3,4-methylene dioxyphenyl | S | C(O)O—CH₂ | 4-pyridinyl | absent | 2.710 |
| 82 | 3,4-methylene dioxyphenyl | R | C(O) | 2-furyl | 4-(4-methylpiperazine-1-carbonyl)phenyl | 0.320 |
| 86 | 5-(2,3-dihydro-benzofuryl) | Rac | C(O)O—CH₂ | phenyl | 4-carboxy | 3.310 |
| 87 | 3,4-methylene dioxyphenyl | Rac | C(O)O—CH₂ | phenyl | 4-carboxy | 1.560 |
| 88 | 3,4-methylene dioxyphenyl | Rac | C(O) | 2-benzofuryl | 6-benzyloxy | 1.430 |
| 92 | 5-(2,3-dihydro-benzofuryl) | Rac | C(O)O—CH₂ | phenyl | 4-methoxy carbonyl | 2.880 |
| 97 | 3,4-methylene dioxyphenyl | Rac | C(O)O—CH₂ | phenyl | absent | 2.120 |
| 98 | 5-(2,3-dihydro-benzofuryl) | Rac | C(O) | 2-benzofuryl | absent | 1.020 |
| 101 | 3,4-methylene dioxyphenyl | Rac | C(O)—cyclopropyl | phenyl | absent | 2.90 |
| 102 | 3,4-methylene dioxyphenyl | Rac | C(O)CH₂ | 3-pyridinyl | absent | 95.10 |

TABLE 4-continued

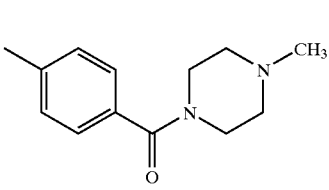

| ID # | R² | Stereo | Y | C | R⁴ | IC₅₀ (nM) |
|---|---|---|---|---|---|---|
| 103 | 3,4-methylene dioxyphenyl | Rac | C(O)—CH=CH | phenyl | absent | 0.540 |
| 104 | 3,4-methylene dioxyphenyl | Rac | C(O)—CH₂ | 4-pyridinyl | absent | 87.050 |
| 106 | 5-(2,3-dihydro-benzofuryl) | Rac | C(O) | 2-furyl | [4-methyl-phenyl-C(O)-piperazinyl-N-CH₃] | 1.30 |
| 107 | 3,4-methylene dioxyphenyl | Rac | C(O)—NH—CH₂ | 4-pyridinyl | absent | 40.550 |
| 110 | 3,4-methylene dioxyphenyl | Rac | C(O) | 2-furyl | 5-phenyl | 0.755 |
| 111 | 3,4-methylene dioxyphenyl | Rac | C(O) | 2-furyl | 5-(4-methyl thiophenyl) | 0.952 |
| 112 | 3,4-methylene dioxyphenyl | Rac | C(O) | 2-furyl | 5-(3-thienyl) | 0.699 |
| 113 | 3,4-methylene dioxyphenyl | Rac | C(O) | 2-furyl | 5-(3-nitrophenyl) | 0.812 |
| 115 | 5-(2,3-dihydro benzofuryl) | Rac | C(O) | 2-imidazolyl | absent | 14.3 |
| 116 | 3,4-methylene dioxyphenyl | Rac | C(O) | 2-furyl | 5-(4methyl phenyl) | 4.01 |
| 117 | 3,4-methylene dioxyphenyl | Rac | C(O) | 2-furyl | 5-(2-furyl) | 4.75 |
| 118 | 3,4-methylene dioxyphenyl | Rac | C(O) | 2-furyl | 5-(3,4-methylene dioxyphenyl | 1.97 |
| 119 | 3,4-methylene dioxyphenyl | Rac | C(O) | 2-furyl | 5-(4-cyano phenyl) | 1.19 |
| 120 | 3,4-methylene dioxyphenyl | Rac | C(O) | 2-furyl | 5-(4-hydroxy methyl phenyl) | 1.22 |
| 121 | 3,4-methylene dioxyphenyl | Rac | C(O) | 2-furyl | 5-(3-hydroxy methyl phenyl) | 0.56 |
| 122 | 3,4-methylene dioxyphenyl | Rac | C(O) | 2-furyl | 5-(4-dimethyl amino phenyl) | 2.05 |
| 135 | 5-(2,3-dihydro benzofuryl) | R | C(O) | S-2-oxa-bicyclo [2.2.1] | 3-oxo-4,7,7-trimethyl | Ki = 13.9 |

TABLE 4-continued

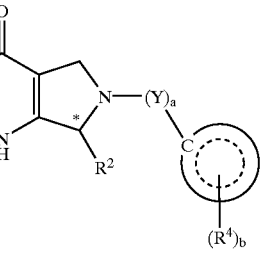

| ID # | R² | Stereo | Y | C (ring) | R⁴ | IC₅₀ (nM) |
|---|---|---|---|---|---|---|
| 139 | 5-(2,3-dihydrobenzofuryl) | R | C(O) | heptanyl R-2-oxa-bicyclo[2.2.1]heptanyl | 3-oxo-4,7,7-trimethyl | |

TABLE 5

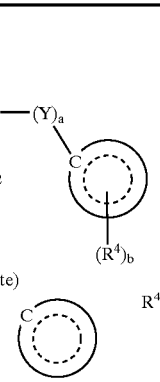

(As Racemate)

| ID # | R² | Y | R³ | C (ring) | R⁴ | IC₅₀ (nM) |
|---|---|---|---|---|---|---|
| 63 | 3,4-methylenedioxyphenyl | C(O)—CH=CH | methyl | phenyl | 4-methoxycarbonyl | 511[a] |

TABLE 6

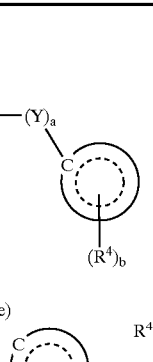

(As Racemate)
(As Racemate)

| ID # | R² | Y | R³ | C (ring) | R⁴ | IC₅₀ (nM) |
|---|---|---|---|---|---|---|
| 64 | 3,4-methylenedioxyphenyl | C(O)—CH=CH | methyl | phenyl | 4-methoxycarbonyl | 113[a] |

[a]Compounds tested using rabbit tissue.

EXAMPLE 97

In Vivo Testing

Following the procedure disclosed by Carter et al., (Carter, A. J., Ballard, S. A., and Naylor, A. M.) in The Journal of Urology 1998, 160, 242–246, the compounds as listed in Table 7 were tested for in vivo efficacy, with results as tabulated below.

TABLE 7

| ID # | Efficacy |
|---|---|
| 36 | Active |
| 37 | Active |
| 65 | Active |
| 66 | Active |

EXAMPLE 98

As a specific embodiment of an oral composition, 100 mg of the compound of Example 21 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound having the formula:

R-1,2,3,4-Tetrahydro-2-[5-(2-pyridinyl)-pyrimidin-2-yl]-3-(2,3-dihydrobenzofuranyl)-9H-pyrrolo-[3,4-b]quinolin-9-one.

2. A compound having the formula:

R-1,2,3,4-tetrahydro-2-(2-pyridinyl)-3-(2,3-dihydro-5-benzofuranyl)-9-H-pyrrolo[3,4-b]quinolin-9-one.

* * * * *